US011311230B2

(12) United States Patent
Sullivan et al.

(10) Patent No.: US 11,311,230 B2
(45) Date of Patent: Apr. 26, 2022

(54) MEDICAL PREMONITORY EVENT ESTIMATION

(71) Applicant: ZOLL Medical Corporation, Chelmsford, MA (US)

(72) Inventors: Adam Sullivan, Pittsburgh, PA (US); Francesco Nicolo, Oakmont, PA (US); Steve Szymkiewicz, Bethel Park, PA (US); Gary A. Freeman, Waltham, MA (US); Gregory R. Frank, Mt. Lebanon, PA (US); Jason T. Whiting, Gibsonia, PA (US); Steve Ringquist, Aspinwall, PA (US); Thomas E. Kaib, Irwin, PA (US); Binwei Weng, Andover, MA (US); Guy R. Johnson, Gloucester, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 110 days.

(21) Appl. No.: 16/359,159

(22) Filed: Mar. 20, 2019

(65) Prior Publication Data
US 2019/0216350 A1 Jul. 18, 2019

Related U.S. Application Data

(62) Division of application No. 14/941,302, filed on Nov. 13, 2015.
(Continued)

(51) Int. Cl.
A61B 7/00 (2006.01)
A61B 5/316 (2021.01)
(Continued)

(52) U.S. Cl.
CPC ............ A61B 5/316 (2021.01); A61B 5/0006 (2013.01); A61B 5/0059 (2013.01); A61B 5/021 (2013.01);
(Continued)

(58) Field of Classification Search
CPC ..... A61B 5/0402; A61B 5/0205; A61B 5/024; A61B 5/363; A61B 5/7275; A61B 5/316;
(Continued)

(56) References Cited

U.S. PATENT DOCUMENTS 5,437,285 A 8/1995 Verrier et al.
5,687,738 A 11/1997 Shapiro et al.
(Continued)

FOREIGN PATENT DOCUMENTS

WO 9835609 A1 8/1998
WO WO2011126823 10/2011
WO WO-2019046854 A1 * 3/2019 ............. G16H 20/10

OTHER PUBLICATIONS

Jessica Torres-Soto, Euan A. Ashley, Multi-task deep learning for cardiac rhythm detection in wearable devices, NPJ, Digital Medicine, Article No. 116, Sep. 2020 (Year: 2020).*
(Continued)

Primary Examiner — Rachelle L Reichert
Assistant Examiner — Teresa S Williams
(74) Attorney, Agent, or Firm — Mintz Levin Cohn Ferris Glovsky and Popeo, P.C.

(57) ABSTRACT

A system and method for medical premonitory event estimation includes one or more processors to perform operations comprising: acquiring a first set of physiological information of a subject, and a second set of physiological information of the subject received during a second period of time; calculating first and second risk scores associated with estimating a risk of a potential cardiac arrhythmia event
(Continued)

for the subject based on applying the first and second sets of physiological information to one or more machine learning classifier models, providing at least the first and second risk scores associated with the potential cardiac arrhythmia event as a time changing series of risk scores, and classifying the first and second risk scores associated with estimating the risk of the potential cardiac arrhythmia event for the subject based on the one or more thresholds.

43 Claims, 29 Drawing Sheets

Related U.S. Application Data

(60) Provisional application No. 62/235,911, filed on Oct. 1, 2015, provisional application No. 62/096,140, filed on Dec. 23, 2014, provisional application No. 62/080,083, filed on Nov. 14, 2014.

(51) Int. Cl.
| | |
|---|---|
| *A61N 1/39* | (2006.01) |
| *A61N 1/04* | (2006.01) |
| *A61N 1/372* | (2006.01) |
| *A61B 5/00* | (2006.01) |
| *G16H 50/30* | (2018.01) |
| *G16H 40/67* | (2018.01) |
| *A61B 5/349* | (2021.01) |
| *A61B 5/0205* | (2006.01) |
| *A61B 5/021* | (2006.01) |
| *A61B 5/0533* | (2021.01) |
| *A61B 5/085* | (2006.01) |
| *A61B 5/11* | (2006.01) |
| *A61B 5/1455* | (2006.01) |
| *A61B 7/04* | (2006.01) |
| *A61B 8/08* | (2006.01) |
| A61B 5/352 | (2021.01) |
| A61B 5/361 | (2021.01) |
| A61B 5/363 | (2021.01) |
| A61B 5/364 | (2021.01) |
| A61B 5/366 | (2021.01) |

(52) U.S. Cl.
CPC .......... *A61B 5/0205* (2013.01); *A61B 5/0533* (2013.01); *A61B 5/085* (2013.01); *A61B 5/1118* (2013.01); *A61B 5/14552* (2013.01); *A61B 5/349* (2021.01); *A61B 5/4803* (2013.01); *A61B 5/686* (2013.01); *A61B 5/7267* (2013.01); *A61B 5/7275* (2013.01); *A61B 7/00* (2013.01); *A61B 7/003* (2013.01); *A61B 7/04* (2013.01); *A61B 8/0883* (2013.01); *A61N 1/046* (2013.01); *A61N 1/0484* (2013.01); *A61N 1/37211* (2013.01); *A61N 1/3925* (2013.01); *A61N 1/3975* (2013.01); *G16H 40/67* (2018.01); *G16H 50/30* (2018.01); *A61B 5/352* (2021.01); *A61B 5/361* (2021.01); *A61B 5/363* (2021.01); *A61B 5/364* (2021.01); *A61B 5/366* (2021.01)

(58) Field of Classification Search
CPC ....... A61B 5/349; A61B 5/0006; A61B 5/021; A61B 5/1118; A61B 5/14542; A61B 5/364; A61B 5/366; A61B 7/00; A61B 5/0533; A61B 5/4803; A61B 40/67; G16H 10/60; G16H 50/30
USPC ...................................................... 600/301
See application file for complete search history.

(56) References Cited

U.S. PATENT DOCUMENTS

| | | | |
|---|---|---|---|
| 6,272,377 B1 | 8/2001 | Sweeney et al. | |
| 6,609,023 B1 | 8/2003 | Fischell et al. | |
| 6,658,287 B1 | 12/2003 | Litt et al. | |
| 7,142,922 B2* | 11/2006 | Spinelli | A61N 1/3627 607/27 |
| 7,194,300 B2 | 3/2007 | Korzinov | |
| 7,462,153 B2 | 12/2008 | Bostian | |
| 7,502,643 B2 | 3/2009 | Farringdon et al. | |
| 8,668,644 B2 | 3/2014 | Ong et al. | |
| 8,932,220 B2 | 1/2015 | Ong et al. | |
| 8,951,193 B2 | 2/2015 | Ong et al. | |
| 9,167,968 B2 | 10/2015 | Saeed | |
| 9,295,429 B2 | 3/2016 | Ong et al. | |
| 9,420,957 B2 | 8/2016 | Ong et al. | |
| 9,687,195 B2 | 6/2017 | Sims | |
| 10,055,549 B2 | 8/2018 | Chung | |
| 10,638,941 B2* | 5/2020 | Albert | G16H 40/63 |
| 2004/0064062 A1 | 4/2004 | Zhou et al. | |
| 2004/0215090 A1 | 10/2004 | Erkkila et al. | |
| 2004/0267570 A1 | 12/2004 | Becker | |
| 2005/0165321 A1 | 7/2005 | Fischell et al. | |
| 2005/0181386 A1* | 8/2005 | Diamond | G16B 20/00 435/6.11 |
| 2005/0234354 A1 | 10/2005 | Rowlandson et al. | |
| 2005/0234355 A1 | 10/2005 | Rowlandson et al. | |
| 2006/0084883 A1 | 4/2006 | Linker | |
| 2006/0234202 A1 | 10/2006 | Brown | |
| 2007/0208266 A1 | 9/2007 | Hadley | |
| 2008/0161712 A1 | 7/2008 | Leyde | |
| 2008/0167567 A1 | 7/2008 | Bashour et al. | |
| 2008/0188763 A1* | 8/2008 | John | A61B 5/349 600/516 |
| 2008/0221633 A1 | 9/2008 | Linker | |
| 2009/0054741 A1 | 2/2009 | McAleer | |
| 2009/0093686 A1 | 4/2009 | Hu et al. | |
| 2009/0228061 A1 | 9/2009 | Lian et al. | |
| 2009/0234410 A1 | 9/2009 | Libbus et al. | |
| 2009/0275848 A1* | 11/2009 | Brockway | A61B 5/7275 600/513 |
| 2010/0030034 A1 | 2/2010 | Schulhauser et al. | |
| 2010/0030293 A1 | 2/2010 | Sarkar et al. | |
| 2010/0204599 A1* | 8/2010 | Pu | A61B 5/0402 600/523 |
| 2010/0280335 A1 | 11/2010 | Carlson et al. | |
| 2011/0137131 A1 | 6/2011 | Adourian | |
| 2011/0184296 A1 | 7/2011 | Vajdic et al. | |
| 2011/0202486 A1 | 8/2011 | Fung | |
| 2012/0022336 A1 | 1/2012 | Teixeira | |
| 2013/0087609 A1 | 4/2013 | Nichol et al. | |
| 2013/0197924 A1 | 8/2013 | Kocis et al. | |
| 2013/0197942 A1 | 8/2013 | Chiu et al. | |
| 2013/0331719 A1 | 12/2013 | Freeman et al. | |
| 2014/0257122 A1 | 9/2014 | Ong et al. | |
| 2015/0018702 A1 | 1/2015 | Galloway et al. | |
| 2015/0088020 A1 | 3/2015 | Dreisbach et al. | |
| 2015/0094552 A1 | 4/2015 | Golda et al. | |
| 2015/0164349 A1 | 6/2015 | Gopalakrishnan et al. | |
| 2015/0342489 A1 | 12/2015 | Bhaumik et al. | |
| 2016/0093205 A1 | 3/2016 | Boyer | |
| 2016/0120430 A1 | 5/2016 | Bayasi et al. | |
| 2016/0135706 A1 | 5/2016 | Sullivan | |

OTHER PUBLICATIONS

International Search Report and Written Opinion, PCT/US2015/060730, dated Mar. 16, 2016, 24 pages.

Lewicke et al. (Jan. 1, 2008) "Sleep Versus Wake 1-15 Classification From Heart Rate Variability Using Computational Intelligence: Consideration of Rejection in Classification Models", IEEE Transactions on Biomedical Engineering, IEEE Service Center, 55(1):108-118.

Ong et al. (Jun. 21, 2012) "Prediction Of Cardiac Arrest In Critically Ill Patients Presenting To The Emergency Department Using A

(56) References Cited

OTHER PUBLICATIONS

Machine Learning Score Incorporating Heart Rate Variability Compared With The Modified Early Warning Score", Critical Care, 16(3):R108(12 pages).
Williamson et al. (Jun. 2, 2013) "Forecasting respiratory collapse: Theory and practice for averting life-threatening infant apneas", Respiratory Physiology and Neurobiology, 189(2):223-231.
Lian et al. (Jan. 1, 2008) "Efficient Similarity Search over Future Stream Time Series", IEEE Transactions on Knowledge and Data Engineering, 20(1):40-54.
Li et al. (Jan. 1, 2012) "An Algorithm Used for Ventricular Fibrillation Detection Without Interrupting Chest Compression", IEEE Transactions on Biomedical Engineering, IEEE Service Center, 59(1):78-86.

* cited by examiner

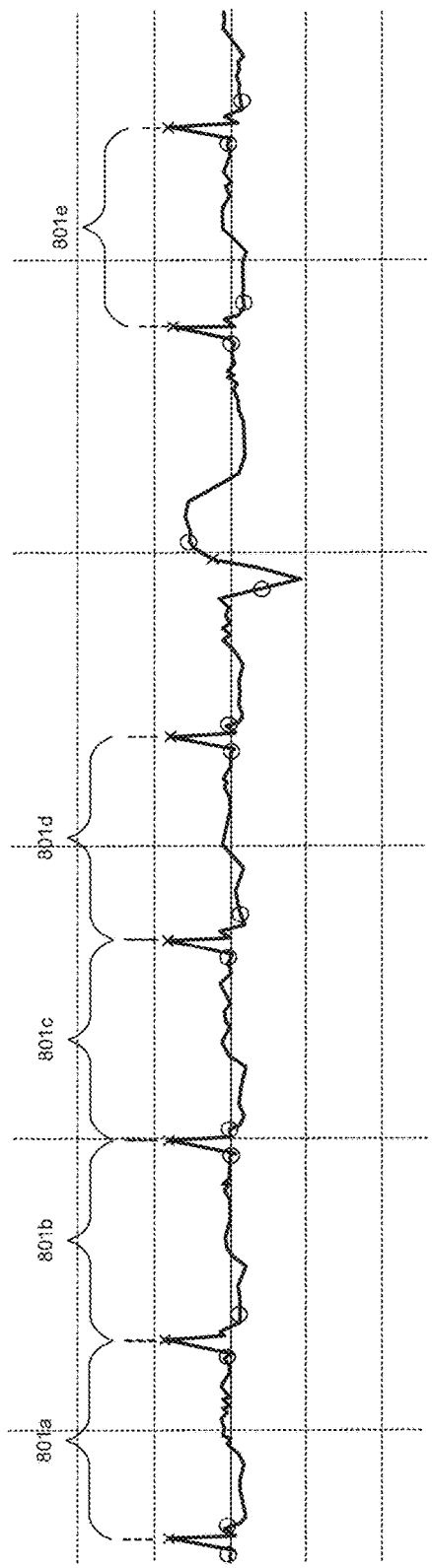
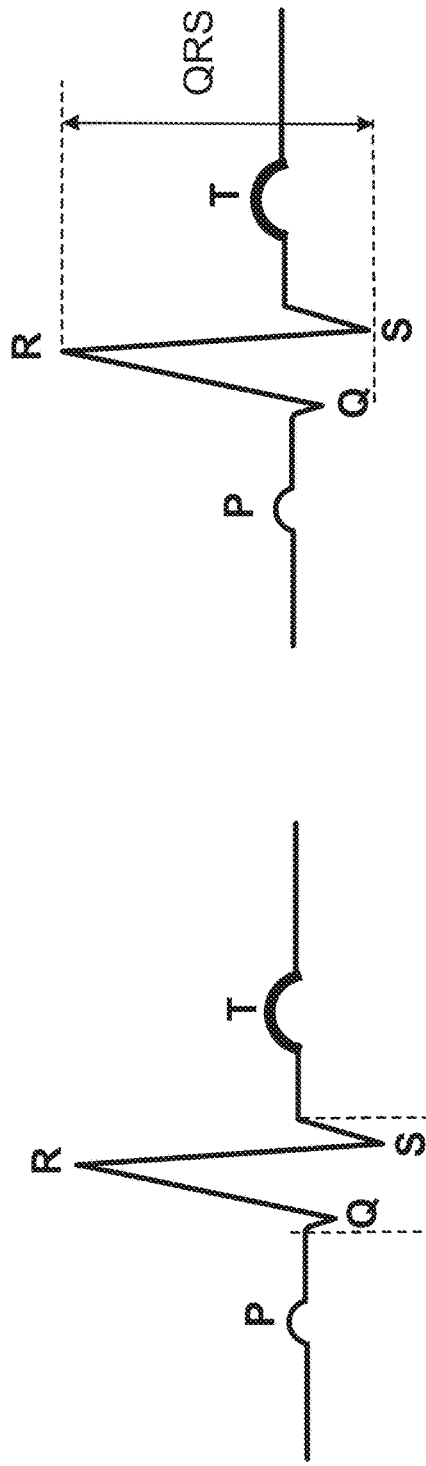
FIG. 8C
FIG. 8D
FIG. 8E

| Metric | Value |
|---|---|
| Training Set | 100 pts |
| Testing Set - Treated | 44 pts |
| Testing Set - Not Treated | 123 pts |
| Sensitivity - Last 4 hours | 60% |
| Specificity – All non treated regions | 98% |
| Specificity - Non-treated patients | 80% |
| Treated Patients with at least 1 warning | 82% |
| Non shock patients who receive a positive SCA prediction but have EOU reason as death | 35% |

Testing Set of 200 patients

FIG. 8L

| MEW Score | | | | | | |
|---|---|---|---|---|---|---|
| | 3 | 2 | 1 | 0 | 1 | 2 | 3 |
| Systolic Blood pressure (mmHg) | <70 | 71-80 | 81-100 | 101-199 | | ≥200 | |
| Heart rate (bpm) | | <40 | 41-50 | 51-100 | 101-110 | 111-129 | ≥130 |
| Respiratory rate (bpm) | | <9 | | 9-14 | 15-20 | 21-29 | ≥30 |
| Temperature (°C) | | <35 | | 35-38.4 | | ≥38.5 | |
| AVPU score | | | | Alert | Reacting to Voice | Reacting to Pain | Unresponsive |

Fig. 15

| GCS Score | 1 | 2 | 3 | 4 | 5 | 6 |
|---|---|---|---|---|---|---|
| Eye | Does not open eyes | Opens eyes in response to painful stimuli | Opens eyes in response to voice | Opens eyes spontaneously | NA | NA |
| Verbal | Makes no sounds | Incomprehensible sounds | Utters inappropriate words | Confused, disoriented | Oriented, converses normally | NA |
| Motor | Makes no movements | Extension to painful stimuli (decerebrate response) | Abnormal flexion to painful stimuli (decorticate response) | Flexion / Withdrawal to painful stimuli | Localizes painful stimuli | Obeys commands |

Fig. 16

MEDICAL PREMONITORY EVENT ESTIMATION

CROSS REFERENCE TO RELATED APPLICATIONS

This application is a divisional application of and claims priority under 35 U.S.C. § 121 to U.S. application Ser. No. 14/941,302, filed on Nov. 13, 2015, which claims priority under 35 U.S.C. § 119(e) to U.S. Provisional Application Ser. No. 62/080,083, entitled "MEDICAL PREMONITORY EVENT ESTIMATION", filed on Nov. 14, 2014; U.S. Provisional Application Ser. No. 62/096,140, entitled "MEDICAL PREMONITORY EVENT ESTIMATION", filed on Dec. 23, 2014; and U.S. Provisional Application Ser. No. 62/235,911, entitled "MEDICAL PREMONITORY EVENT ESTIMATION", filed on Oct. 1, 2015, the entire contents of all of which are incorporated herein by reference.

BACKGROUND

Technical Field

The present invention relates to medical premonitory event estimation and detection systems and methods and, in some embodiments, to systems and methods for calculating an event estimation of risk score associated with a potential medical event for a subject.

Description of Related Art

There are many patients at risk for sudden death as a result of cardiac tachyarrhythmia induced sudden cardiac arrest or asystole. For example, patients with reduced left ventricular ejection fraction and diagnoses of myocardial infarction, non-ischemic cardiomyopathy, dilated cardiomyopathy and congestive heart failure have been recognized as having elevated risk compared with the general population. Validated methods for determining gradation of risk within these populations that would lead to recognition of early warning signs prior to onset of sudden cardiac death are lacking. In the absence of reliable methods for classification of subjects for elevated risk, the treatment recommendations available for these patients frequently involve hospitalization and prescription of drug therapy followed by observation. Despite the availability of drug therapy the rate of sudden death has decreased only slightly, and once a subject experiences sudden cardiac arrest the only proven treatment is defibrillation. In fact, the chances that a subject will survive sudden cardiac arrest diminish at a rate of approximately 10% for each minute that defibrillation treatment is delayed. As a result, subjects would benefit from systems and methods for detecting early warning signs of elevated risk of sudden cardiac death that would enable proactive decisions such as the application of advanced medical intervention.

During the course of use, a medical device monitoring the physiologic status of a subject, such as a portable defibrillator monitor, a wearable defibrillator, a wearable insulin pump, a wearable ECG monitor or monitor of other physiologic parameters, etc., may issue audible alarms, voice prompts or messages, or visual messages to alert a subject or a bystander to a medical condition, to direct the subject or bystander to take some action to correct a problem, to call for assistance, to request information from the subject or the bystander, or to provide feedback to the device so that the device may continue to function properly. For example, if the medical device is a wearable defibrillator, the device may issue alarms and voice messages to provide instruction to the subject when the device determines that the subject is experiencing cardiac arrhythmia. Alarms and messages may also be directed to a bystander instructing the bystander to call for medical assistance, or to alert any bystanders that a defibrillating shock is about to be delivered and to stand clear of the subject.

SUMMARY

In some embodiments, a medical premonitory event estimation system is provided, the system comprising: a nontransitory computer-readable storage medium in communication with one or more processors and having instructions stored thereon which, when executed by the one or more processors, cause the one or more processors to perform operations comprising: for a plurality of time periods, calculating an event estimation of risk score associated with a potential medical event for a subject occurring within of the associated time period based at least partly on physiological parameter data of the subject.

Preferred and non-limiting embodiments or aspects of the present invention will now be described in the following numbered clauses:

Clause 1. A medical premonitory event estimation system, comprising: a nontransitory computer-readable storage medium in communication with one or more processors and having instructions stored thereon which, when executed by the one or more processors, cause the one or more processors to perform operations comprising: for a plurality of time periods, calculating an event estimation of risk score associated with a potential medical event for a subject occurring within the associated time period based at least partly on physiological parameter data of the subject.

Clause 2. The system of clause 1, wherein the physiological parameter data comprises ECG data.

Clause 3. The system of clause 1 or 2, wherein the physiological parameter data comprises at least one of blood pressure data, heart rate data, thoracic impedance data, pulse oxygen level data, respiration rate data, heart sound data, lung sound data, and activity level data.

Clause 4. The system of any of clauses 1-3, wherein the potential medical event comprises a cardiac event.

Clause 5. The system of clause 4, wherein the cardiac event comprises at least one of an ectopic beat, a run of ectopic beats, a ventricular tachycardia, a bradycardia, asystole, and a T-wave abnormality.

Clause 6. The system of any one of clauses 1-5, wherein the potential medical event comprises at least one of a plurality of medical events, an increase in a rate of medical events, and/or an increase in an intensity of medical events.

Clause 7. The system of any one of clauses 1-6, wherein the potential medical event is defined in a multidimensional parameter space comprising the physiological parameter data and at least one other type of physiological parameter data and/or demographic data of the subject.

Clause 8. The system of any one of clauses 1-7, wherein the one or more processors perform operations comprising: calculating a plurality of different event estimation of risk scores associated with the potential medical event for the subject within the associated time period based at least partly on the physiological parameter data.

Clause 9. The system of any one of clauses 1-8, wherein the one or more processors perform operations comprising: calculating a plurality of different event estimation of risk scores associated with a plurality of different potential medical events for the subject within the associated time period based at least partly on the physiological parameter data.

Clause 10. The system of any one of clauses 1-9, wherein the calculating the event estimation of risk score comprises calculating a criticality score indicating a significance of the potential medical event with respect to at least one other potential medical event.

Clause 11. The system of any one of clauses 1-10, wherein the calculating the event estimation of risk score comprises calculating a confidence score including a probability that the potential medical event occurs within the associated time period.

Clause 12. The system of any one of clauses 1-11, wherein the one or more processors perform operations comprising: determining that the event estimation of risk score satisfies one or more event estimation of risk thresholds for the associated time period; and determining a response to the potential medical event based at least partly on the one or more event estimation of risk thresholds determined to be satisfied.

Clause 13. The system of clause 12, wherein the determined response to the potential medical event includes at least one of informing the subject of advanced diagnostics, advising the subject against removal of equipment, advising the subject of a behavior modification, alerting a medical professional, and preparing a device for treatment.

Clause 14. The system of any one of clauses 12-13, wherein each of the one or more event estimation of risk thresholds include at least one confidence threshold including a required probability that the potential medical event occurs within the associated time period and at least one criticality threshold including a required significance of the potential medical event with respect to at least one other potential medical event.

Clause 15. The system of any one of clauses 12-14, wherein the one or more event estimation of risk thresholds comprise a plurality of different event estimation of risk thresholds for the associated time period.

Clause 16. The system of any of clauses 12-15, wherein the one or more event estimation of risk thresholds for a first time period are different than the one or more event estimation of risk thresholds for a second time period.

Clause 17. The system of any of clauses 12-16, wherein the determined response to the potential medical event for the subject occurring within a first associated time period is different that the determined response to the potential medical event for the subject occurring within a second associated time period.

Clause 18. The system of any of clauses 1-17, wherein the one or more processors perform operations comprising: determining that the event estimation of risk score fails to satisfies at least one event estimation of risk threshold for the associated time period; receiving additional data of the subject; and calculating an enhanced event estimation of risk score associated with the potential medical event for the subject occurring within the associated time period based at least partly on the physiological parameter data and the additional data.

Clause 19. The system of clause 18, wherein the additional data comprises at least one of image data of the subject, audio data including the voice of the subject, and data based on a galvanic skin response of the subject.

Clause 20. The system of any of clauses 18-19, wherein the one or more processors perform operations comprising: setting the one or more event estimation of risk thresholds based at least partly on historical patient data collected from a plurality of patients.

Clause 21. The system of any of clauses 18-20, wherein the one or more processors perform operations comprising: setting the one or more event estimation of risk thresholds based at least partly on input from a user.

Clause 22. The system of any of clauses 1-21, wherein the one or more processors perform operations comprising: calculating the event estimation of risk score at periodic time intervals.

Clause 23. The system of any of clauses 1-21, wherein the one or more processors perform operations comprising: calculating the event estimation of risk score is at dynamic time intervals, wherein a duration of the dynamic time intervals is based at least partly on the event estimation of risk score.

Clause 24. The system of any of clauses 1-21, wherein the one or more processors perform operations comprising: continuously calculating the event estimation of risk score is continuously calculated.

Clause 25. The system of any of clauses 1-24, wherein the calculating the event estimation of risk score comprises applying a logistic regression model to the physiological parameter data to determine the event estimation of risk score.

Clause 26. The system of any of clauses 1-24, wherein the calculating the event estimation of risk score comprises: generating at least two generally orthogonal vectors based at least partly on the physiological parameter data; processing the at least two generally orthogonal vectors to determine a loop trajectory of the physiological parameter data; identifying a trajectory bifurcation by: characterizing a group of control loop trajectories that includes one or more loop trajectories obtained during a first time period; characterizing a group of test loop trajectories that includes one or more loop trajectories obtained during a second time period that is subsequent to the first time period; comparing the characterization of the group of control loop trajectories to the characterization of the group of test loop trajectories; measuring a degree of trajectory bifurcation between the group of control loop trajectories and the group of test loop trajectories; and calculating the event estimation of risk score based at least in part on the measure of the degree of trajectory bifurcation.

Clause 27. The system of any of clauses 1-24, wherein the calculating the event estimation of risk score comprises: calculating a first event estimation of risk score including a first criticality score for a first potential medical event; calculating a second event estimation of risk score including a second criticality score for a second potential medical event based at least partly on the first event estimation of risk score, wherein the first criticality score indicates that a significance of the first potential medical event is different than a significance of the second potential medical event.

Clause 28. The system of any of clauses 1-24, wherein the calculating the event estimation of risk score comprises: calculating a first event estimation of risk score associated with the potential medical event for the subject occurring within of the associated time period based on a first shockable rhythm detection algorithm; and calculating a second event estimation of risk score associated with the potential medical event for the subject occurring within of the associated time period based on a second rhythm detection algorithm, wherein the second rhythm detection algorithm is tuned for a higher sensitivity on the physiological data than the first rhythm detection algorithm.

Clause 29. The system of any of clauses 1-24, wherein the calculating the event estimation of risk score comprises: applying at least two different rhythm detection algorithms to different time segments of the physiological data.

Clause 30. The system of any of clauses 1-24, wherein the calculating the event estimation of risk score comprises: receiving data indicating a viability of a patient; and determining a response to the potential medical event based at least partly on the viability of the patient.

Clause 31. The system of any of clauses 1-30, further comprising: a medical device comprising one or more sensors configured to sense the physiological parameter data of the subject.

Clause 32. The system of clause 1-31, wherein the medical device comprises a wearable medical device, wherein the one or more sensors comprise a plurality of ECG sensors, wherein the physiological parameter data of the subject comprises ECG data, and wherein the potential medical event comprises a cardiac event.

Clause 33. The system of any of clauses 31 and 32, further comprising: a communications network configured to communicate at least one of the physiological parameter data and the event estimation of risk score from the medical device to another computing device.

Clause 34. The system of any of clauses 1-33, further comprising: a display for displaying a time-based visual indicator of the event estimation of risk score for the plurality of time periods.

Clause 35. The system of any of clauses 1-34, wherein the one or more processors perform operations comprising: determining a response to the potential medical event based at least partly on the event estimation of risk score.

Clause 36. The system of any of clause 35, wherein the determined response to the potential medical event includes providing an instruction to the subject to contact a medical professional.

Clause 37. The system of any of clauses 35 and 36, further comprising: a wearable medical device, wherein the determined response to the potential medical event includes providing an instruction to the subject to check a battery of the wearable medical device.

Clause 38. The system of any of clauses 35-37, further comprising: a wearable medical device, wherein the determined response to the potential medical event includes charging a shocking mechanism of the wearable medical device.

Clause 39. The system of any of clauses 35-38, wherein the one or more processors perform operations comprising: determining the response to the potential medical event based at least partly on a sensitivity and a specificity of the event estimation of risk score.

Clause 40. The system of clause 35-39, wherein the determined response based on a first sensitivity and a first specificity is different than the determined response based on a second different sensitivity and second different specificity.

Clause 41. The system of any of clauses 35-40, wherein the determined response to the potential medical event includes at least one of informing the subject of advanced diagnostics, advising the subject against removal of equipment, advising the subject of a behavior modification, alerting a medical professional, and preparing a device for treatment.

Clause 42. The system of any of clauses 35-41, wherein the one or more processors perform operations comprising: modifying a sensitivity of an algorithm for determining the event estimation of risk score based on a risk level of the subject.

Clause 43. The system of any of clauses 1-42, wherein the plurality of time period comprise at least one time period of less than about ten minutes, at least one time period of less than about one hour, at least one time period of less than about three hours, at least one time period of less than about one day, at least one time period of less than about one week, and at least one time period of less than about one month.

Clause 44. The system of any of clauses 1-43, wherein the calculating the event estimation of risk score comprises calculating a confidence band of the event estimation of risk score Clause 45. The system of any of clauses 1-44, wherein the calculating the event estimation of risk score comprises calculating an error band of the event estimation of risk score.

Clause 46. The system of any of clauses 1-45, wherein the plurality of time periods comprise a plurality of time periods of less than four hours.

Clause 47. A method for medical premonitory event estimation, comprising: receiving, by one or more processors, physiological parameter data of a subject; and for a plurality of time periods, calculating, by the one or more processors, an event estimation of risk score associated with a potential medical event for the subject occurring within the associated time period based at least partly on the physiological parameter data of the subject.

Clause 48. The method of clause 47, wherein the physiological parameter data comprises ECG data.

Clause 49. The method of any of clauses 47 and 48, wherein the physiological parameter data comprises at least one of blood pressure data, heart rate data, thoracic impedance data, pulse oxygen level data, respiration rate data, heart sound data, lung sound data, and activity level data.

Clause 50. The method of any of clauses 47-49, wherein the potential medical event comprises a cardiac event.

Clause 51. The method of clause 50, wherein the cardiac event comprises at least one of an ectopic beat, a run of ectopic beats, a ventricular tachycardia, a bradycardia, asystole, and a T-wave abnormality.

Clause 52. The method of any of clauses 47-51, wherein the potential medical event comprises at least one of a plurality of medical events, an increase in a rate of medical events, and/or an increase in an intensity of medical events.

Clause 53. The method of any of clauses 47-52, wherein the potential medical event is defined in a multidimensional parameter space comprising the physiological parameter data and at least one other type of physiological parameter data and/or demographic data of the subject.

Clause 54. The method of any of clauses 47-53, further comprising: calculating, by the one or more processors, a plurality of different event estimation of risk scores associated with the potential medical event for the subject within the associated time period based at least partly on the physiological parameter data.

Clause 55. The method of any of clauses 47-54, further comprising: calculating, by the one or more processors, a plurality of different event estimation of risk scores associated with a plurality of different potential medical events for the subject within the associated time period based at least partly on the physiological parameter data.

Clause 56. The method of any of clauses 47-55, wherein the calculating the event estimation of risk score comprises calculating a criticality score indicating a significance of the potential medical event with respect to at least one other potential medical event.

Clause 57. The method of any of clauses 47-56, wherein the calculating the event estimation of risk score comprises calculating a confidence score including a probability that the potential medical event occurs within the associated time period.

Clause 58. The method of any of clauses 47-57, further comprising: determining, by the one or more processors, that the event estimation of risk score satisfies one or more event estimation of risk thresholds for the associated time period; and determining, by the one or more processors, a response to the potential medical event based at least partly on the one or more event estimation of risk thresholds determined to be satisfied.

Clause 59. The method of clause 58, wherein the determined response to the potential medical event includes at least one of informing the subject of advanced diagnostics, advising the subject against removal of equipment, advising the subject of a behavior modification, alerting a medical professional, and preparing a device for treatment.

Clause 60. The method of any of clauses 58 and 59, wherein each of the one or more event estimation of risk thresholds include at least one confidence threshold including a required probability that the potential medical event occurs within the associated time period and at least one criticality threshold including a required significance of the potential medical event with respect to at least one other potential medical event.

Clause 61. The method of any of clauses 58-60, wherein the one or more event estimation of risk thresholds comprise a plurality of different event estimation of risk thresholds for the associated time period.

Clause 62. The method of any of clauses 58-61, wherein the one or more event estimation of risk thresholds for a first time period are different than the one or more event estimation of risk thresholds for a second time period.

Clause 63. The method of any one of clauses 58-62, wherein the determined response to the potential medical event for the subject occurring within a first associated time period is different that the determined response to the potential medical event for the subject occurring within a second associated time period.

Clause 64. The method of any of clauses 47-63, further comprising: determining, by the one or more processors, that the event estimation of risk score fails to satisfies at least one event estimation of risk threshold for the associated time period; receiving, by the one or more processors, additional data of the subject; and calculating, by the one or more processors, an enhanced event estimation of risk score associated with the potential medical event for the subject occurring within the associated time period based at least partly on the physiological parameter data and the additional data.

Clause 65. The method of clause 64, wherein the additional data comprises at least one of image data of the subject, audio data including the voice of the subject, and data based on a galvanic skin response of the subject.

Clause 66. The method of any of clause 58-65, further comprising: setting, by the one or more processors, the one or more event estimation of risk thresholds based at least partly on historical patient data collected from a plurality of patients.

Clause 67. The method of any of clauses 58-66, further comprising setting, by the one or more processors, the one or more event estimation of risk thresholds based at least partly on input from a user.

Clause 68. The method of any of clauses 47-67, further comprising: calculating, by the one or more processors, the event estimation of risk score at periodic time intervals.

Clause 69. The method of any of clauses 47-67, further comprising: calculating, by the one or more processors, the event estimation of risk score at dynamic time intervals, wherein a duration of the dynamic time intervals is based at least partly on the event estimation of risk score.

Clause 70. The method of any of clauses 47-67, further comprising: continuously calculating, by the one or more processors, the event estimation of risk score.

Clause 71. The method of any of clauses 47-70, wherein the calculating the event estimation of risk score comprises applying a logistic regression model to the physiological parameter data to determine the event estimation of risk score.

Clause 72. The method of any of clauses 47-70, wherein the calculating the event estimation of risk score comprises: generating at least two generally orthogonal vectors based at least partly on the physiological parameter data; processing the at least two generally orthogonal vectors to determine a loop trajectory of the physiological parameter data; identifying a trajectory bifurcation by: characterizing a group of control loop trajectories that includes one or more loop trajectories obtained during a first time period; characterizing a group of test loop trajectories that includes one or more loop trajectories obtained during a second time period that is subsequent to the first time period; comparing the characterization of the group of control loop trajectories to the characterization of the group of test loop trajectories; measuring a degree of trajectory bifurcation between the group of control loop trajectories and the group of test loop trajectories; and calculating the event estimation of risk score based at least in part on the measure of the degree of trajectory bifurcation.

Clause 73. The method of any of clauses 47-70, wherein the calculating the event estimation of risk score comprises: calculating a first event estimation of risk score including a first criticality score for a first potential medical event; calculating a second event estimation of risk score including a second criticality score for a second potential medical event based at least partly on the first event estimation of risk score, wherein the first criticality score indicates that a significance of the first potential medical event is different than a significance of the second potential medical event.

Clause 74. The method of any of clauses 47-70, wherein the calculating the event estimation of risk score comprises: calculating a first event estimation of risk score associated with the potential medical event for the subject occurring within of the associated time period based on a first shockable rhythm detection algorithm; and calculating a second event estimation of risk score associated with the potential medical event for the subject occurring within of the associated time period based on a second rhythm detection algorithm, wherein the second rhythm detection algorithm is tuned for a higher sensitivity on the physiological data than the first rhythm detection algorithm.

Clause 75. The method of any of clauses 47-70, wherein the calculating the event estimation of risk score comprises: applying at least two different rhythm detection algorithms to different time segments of the physiological data.

Clause 76. The method of any of clauses 47-70, wherein the calculating the event estimation of risk score comprises: receiving data indicating a viability of a patient; and determining a response to the potential medical event based at least partly on the viability of the patient.

Clause 77. The method of any of clauses 47-70, further comprising: sensing, by a medical device comprising one or more sensors, the physiological parameter data of the subject.

Clause 78. The method of clause 77, wherein the medical devices comprises a wearable medical device, wherein the one or more sensors comprise a plurality of ECG sensors, wherein the physiological parameter data of the subject comprises ECG data, and wherein the potential medical event comprises a cardiac event.

Clause 79. The method of any of clauses 47-78, further comprising: communicating, by a communications network, at least one of the physiological parameter data and the event estimation of risk score from the medical device to another computing device.

Clause 80. The method of any of clauses 47-79, further comprising: displaying, by a display controlled by the one or more processors, a time-based visual indicator of the event estimation of risk score for the plurality of time periods.

Clause 81. The method of any of clauses 47-80, wherein the plurality of time periods comprise a plurality of time periods of less than four hours.

Clause 82. The method of any of clauses 47-80, wherein the plurality of time period comprise at least one time period of less than about ten minutes, at least one time period of less than about one hour, at least one time period of less than about three hours, at least one time period of less than about one day, at least one time period of less than about one week, and at least one time period of less than about one month.

Clause 83. The method of any of clauses 47-80, wherein the calculating the event estimation of risk score comprises calculating a confidence band of the event estimation of risk score.

Clause 84. The method of any of clauses 47-80, wherein the calculating the event estimation of risk score comprises calculating an error band of the event estimation of risk score.

Clause 85. The method of any of clauses 47-84, further comprising: determining a response to the potential medical event based at least partly on the event estimation of risk score.

Clause 86. The method of clause 85, wherein the determined response to the potential medical event includes providing an instruction to the subject to contact a medical professional.

Clause 87. The system of any of clauses 85 and 86, wherein the determined response to the potential medical event includes providing an instruction to the subject to check a battery of a wearable medical device.

Clause 88. The system of any of clauses 85-87, wherein the determined response to the potential medical event includes charging a shocking mechanism of a wearable medical device.

Clause 89. The system of any of clauses 85-88, further comprising: determining the response to the potential medical event based at least partly on a sensitivity and a specificity of the event estimation of risk score.

Clause 90. The system of clause 89, wherein the determined response based on a first sensitivity and a first specificity is different than the determined response based on a second different sensitivity and second different specificity.

Clause 91. The system of any of clauses 85-90, wherein the determined response to the potential medical event includes at least one of informing the subject of advanced diagnostics, advising the subject against removal of equipment, advising the subject of a behavior modification, alerting a medical professional, and preparing a device for treatment.

Clause 92. The system of any of clauses 85-91, further comprising: modifying a sensitivity of an algorithm for determining the event estimation of risk score based on a risk level of the subject.

Clause 93. A medical event estimation system, comprising: at least one non-transitory computer-readable storage medium in communication with at least one processor and having instructions stored thereon which, when executed by the at least one processor, cause the at least one processor to perform operations comprising: receiving at least one signal comprising physiological parameter data of a subject; and calculating estimation of time to potential events associated with at least two different potential medical events for the subject based at least partly on the physiological parameter data.

Clause 94. A medical event estimation system, comprising: at least one non-transitory computer-readable storage medium in communication with at least one processor and having instructions stored thereon which, when executed by the at least one processor, cause the at least one processor to perform operations comprising: receiving at least one signal comprising physiological parameter data of a subject; and calculating risk scores based upon estimation of time to potential events associated with at least two different potential medical events for the subject based at least partly on the physiological parameter data.

Clause 95. A medical event estimation system, comprising: a medical device configured to measure physiological parameter data of a subject, transmit a signal comprising the physiological parameter data of the subject, and perform a plurality of different actions in response to a plurality of different medical events; and at least one non-transitory computer readable storage medium in communication with at least one processor and having instructions stored thereon which, when executed by the at least one processor, cause the at least one processor to perform operations comprising: receiving the at least one signal comprising the physiological parameter data of the subject; calculating risk scores based upon estimation of time to potential events associated with at least two different potential medical events for the subject based at least partly on the physiological parameter data; and controlling the medical device to perform at least one action of the plurality of different actions based at least partly on at least one of the calculated risk scores.

Clause 96. A method for medical event estimation, comprising: measuring, by a medical device, physiological parameter data of a subject; transmitting, by the medical device, a signal comprising the physiological parameter data of the subject; receiving, by one or more processors, the at least one signal comprising the physiological parameter data of the subject; calculating, by the one or more processors, risk scores based upon estimation of time to potential events associated with at least two different potential medical events for the subject based at least partly on the physiological parameter data; and performing, by the medical device, at least one action of a plurality of different actions based at least partly on at least one of the calculated risk scores.

Clause 97. A medical premonitory event estimation system, comprising: a nontransitory computer-readable storage medium in communication with one or more processors and having instructions stored thereon which, when executed by the one or more processors, cause the one or more processors to perform operations comprising: calculating an event estimation of risk score associated with a potential medical event for a subject occurring within an associated time period based at least partly on a physiological parameter signal of the subject, wherein the calculating the event estimation of risk score comprises: extracting a plurality of physiological measurements from the physiological parameter signal of the subject; combining at least a portion of the plurality of physiological measurements in a multivariate parameter signal; applying a change point analysis to the multivariate parameter signal to determine at least one change point; determining a distance of the at least one change point from a baseline; applying an anomaly detection to the multivariate parameter signal to determine at least one anomaly score; and determining the event estimation of risk score based at least partly on the at least one distance and the at least one anomaly score.

Clause 98. The system of clause 97, wherein the physiological parameter signal comprises an ECG signal of the subject.

Clause 99. The system of any of clauses 97 and 98, wherein the plurality of physiological measurements extracted from the ECG signal include at least one of heart rate, heart rate variability, PVC burden or counts, activity, noise quantifications, atrial fibrillation, momentary pauses, heart rate turbulence, QRS height, QRS width, changes in the size or shape of the morphology, cosine R-T, artificial pacing, corrected QT interval, QT variability, T wave width, T wave alternans, T-wave variability, ST segment changes, early repolarization, late potentials, fractionated QRS/HF content, and fractionated T wave/HF content.

Clause 100. The system of any of clauses 97-99, wherein the physiological parameter signal further comprises an accelerometer signal.

Clause 101. The system of clause 100, wherein the calculating the event estimation of risk scores further comprises: removing one or more ECG signal artifacts from the ECG signal based at least partly on the accelerometer signal.

Clause 102. The system of any of clauses 97-101, wherein the calculating the event estimation of risk score further comprises: calculating a statistical value of the multivariate parameter signal for at least one interval of the multivariate parameter signal associated with the at least one change point; and determining a difference between the at least one statistical value and a corresponding statistical value of the baseline.

Clause 103. The system of any of clauses 97-102, wherein the applying the anomaly detection further comprises determining a plurality of raw single-parameter outputs corresponding to the plurality of physiological parameter measurements.

Clause 104. The system of any of clauses 97-103, wherein the anomaly detection comprises a neural network, and wherein the neural network is trained on the baseline of the multivariate parameter signal.

Clause 105. The system of any of clauses 97-104, wherein the determining the event estimation of risk score based at least partly on the at least one distance and the at least one anomaly score comprises classifying the at least one distance and the at least one anomaly score using one or more machine learning processes.

Clause 106. The system of any of clauses 97-105, wherein the calculating the event estimation of risk score further comprises: applying a change point analysis to the multivariate parameter signal to determine a plurality of change points; determining a plurality of distances of the plurality of change points from a baseline; applying an anomaly detection to the multivariate parameter signal to determine a plurality of anomaly scores corresponding to the plurality of change points; and determining the event estimation of risk score for the plurality of change points based the plurality of distances and the plurality of anomaly scores.

Clause 107. The system of any of clauses 97-106, further comprising a wearable medical device.

Clause 108. A method for medical premonitory event estimation, the method comprising: calculating, by one or more processors, an event estimation of risk score associated with a potential medical event for a subject occurring within an associated time period based at least partly on a physiological parameter signal of the subject, wherein the calculating the event estimation of risk score comprises: extracting a plurality of physiological measurements from the physiological parameter signal of the subject; combining at least a portion of the plurality of physiological measurements in a multivariate parameter signal; applying a change point analysis to the multivariate parameter signal to determine at least one change point; determining a distance of the at least one change point from a baseline; applying an anomaly detection to the multivariate parameter signal to determine at least one anomaly score; and determining the event estimation of risk score based at least partly on the at least one distance and the at least one anomaly score.

Clause 109. The method of clause 108, wherein the physiological parameter signal comprises an ECG signal of the subject.

Clause 110. The method of any of clauses 108 and 109, wherein the plurality of physiological measurements extracted from the ECG signal include at least one of heart rate, heart rate variability, PVC burden or counts, activity, noise quantifications, atrial fibrillation, momentary pauses, heart rate turbulence, QRS height, QRS width, changes in the size or shape of the morphology, cosine R-T, artificial pacing, corrected QT interval, QT variability, T wave width, T wave alternans, T-wave variability, ST segment changes, early repolarization, late potentials, fractionated QRS/HF content, and fractionated T wave/HF content.

Clause 111. The method of any of clauses 108-110, wherein the physiological parameter signal further comprises an accelerometer signal.

Clause 112. The method of clause 111, wherein the calculating the event estimation of risk scores further comprises: removing one or more ECG signal artifacts from the ECG signal based at least partly on the accelerometer signal.

Clause 113. The method of any of clauses 108-112, wherein the calculating the event estimation of risk score further comprises: calculating a statistical value of the multivariate parameter signal for at least one interval of the multivariate parameter signal associated with the at least one change point; and determining a difference between the at least one statistical value and a corresponding statistical value of the baseline.

Clause 114. The method of any of clauses 108-113, wherein the applying the anomaly detection further comprises determining a plurality of raw single-parameter outputs corresponding to the plurality of physiological parameter measurements.

Clause 115. The method of any of clauses 108-114, wherein the anomaly detection comprises a neural network, and wherein the neural network is trained on the baseline of the multivariate parameter signal.

Clause 116. The method of any of clauses 108-115, wherein the determining the event estimation of risk score based at least partly on the at least one distance and the at least one anomaly score comprises classifying the at least one distance and the at least one anomaly score using one or more machine learning processes.

Clause 117. The method of any of clauses 108-116, wherein the calculating the event estimation of risk score further comprises: applying a change point analysis to the multivariate parameter signal to determine a plurality of change points; determining a plurality of distances of the plurality of change points from a baseline; applying an anomaly detection to the multivariate parameter signal to determine a plurality of anomaly scores corresponding to the plurality of change points; and determining the event estimation of risk score for the plurality of change points based the plurality of distances and the plurality of anomaly scores.

Clause 118. A wearable medical device configured to perform the method of any of clauses 108-117.

Clause 119. A medical premonitory event estimation system, comprising: a nontransitory computer-readable storage medium in communication with one or more processors and having instructions stored thereon which, when executed by the one or more processors, cause the one or more processors to perform operations comprising: acquiring a first set of physiological information of a subject received during a first period of time and based at least in part on a first ECG signal of the subject, and a second set of physiological information of the subject received during a second period of time; calculating first and second risk scores associated with estimating a risk of a potential cardiac arrhythmia event for the subject based on applying the first and second sets of physiological information to one or more machine learning classifier models trained on training metrics comprising at least one of i) cardiac electrophysiology metrics of a first plurality of subjects, and ii) at least one of demographic metrics and medical history metrics of the first plurality of subjects, wherein the one or more machine learning classifier models is validated on validation metrics of a second plurality of subjects, and wherein one or more thresholds of the one or more machine learning classifier models is set based on the validation; providing at least the first and second risk scores associated with the potential cardiac arrhythmia event as a time changing series of risk scores; and classifying the first and second risk scores associated with estimating the risk of the potential cardiac arrhythmia event for the subject based on the one or more thresholds.

Clause 120. The system of clause 119, wherein the one or more thresholds comprise at least an elevated risk threshold and an immediate risk threshold, and wherein the classifying comprises for each of the first and second risk scores classifying the risk of the potential cardiac arrhythmia event for the subject as an elevated risk based on the first or second risk score transgressing the elevated risk threshold; and classifying the risk of the potential cardiac arrhythmia event for the subject as an immediate risk based on the first or second risk score transgressing the immediate risk threshold.

Clause 121. The system of clause 119 or clause 120, wherein the classifying comprises a time changing classification of the risk of the potential cardiac arrhythmia event for the subject based on the time changing series of risk scores.

Clause 122. The system of any of clauses 119-121, wherein the classifying comprises adjusting an underlying specificity of the one or more machine learning classifier models to reduce type 1 errors (false positives) in the underlying classification of the risk of the potential cardiac arrhythmia event for the subject.

Clause 123. The system of any of clauses 119-122, wherein the validation metrics comprises a plurality of one or more of cardiac electrophysiology metrics, demographic metrics, and medical history metrics of the second plurality of subjects.

Clause 124. The system of any of clauses 119-123, wherein the one or more processors perform operations comprising: updating the validation metrics by at least one of 1) adjusting one or more of the metrics in the validation metrics, and 2) expanding the validation metrics based on appending additional one or more subjects to the second plurality of subjects; and refining the one or more thresholds based on the updated validation metrics.

Clause 125. The system of any of clauses 119-124, wherein the one or more processors perform operations comprising: updating the training metrics by at least one of 1) adjusting one or more of the metrics in the training metrics, and 2) expanding the training metrics based on appending additional one or more subjects to the first plurality of subjects; and retraining the one or more machine learning classifier models based on the updated training metrics.

Clause 126. The system of any of clauses 119-125, wherein the validation metrics of the second plurality of subjects is independent from the training metrics of the first plurality of subjects.

Clause 127. The system of any of clauses 119-126, wherein the one or more machine learning classifier models are validated on the validation metrics, and wherein the validation metrics comprises an indication of the presence or absence of ectopic beats in an underlying one or more of the validation metrics.

Clause 128. The system of any of clauses 119-127, wherein the one or more processors perform operations comprising: discriminating between normal and ectopic beats in the first set of physiological information of the subject received during the first period of time and based at least in part on the first ECG signal.

Clause 129. The system of any of clauses 119-128, wherein at least one of the training metrics and the validation metrics comprises metrics based on at least one of heart rate, heart rate variability, non-sustained ventricular tachycardia (VT) episodes count, and premature ventricular contraction (PVC) count.

Clause 130. The system of any of clauses 119-129, wherein at least one of the training metrics and the validation metrics comprises metrics based on heart rate variability, and wherein the metrics comprise a standard deviation over time of normal-to-normal intervals.

Clause 131. The system of any of clauses 119-130, wherein at least one of the training metrics and the validation metrics comprises metrics based on at least one of QRS width, QRS height, single lead QRS morphology, and dual lead QRS morphology.

Clause 132. The system of any of clauses 119-131, wherein at least one of the training metrics and the validation metrics comprises metrics based on single lead QRS morphology, and wherein the metrics comprise an average over time of similarity scores respectively on side-to-side (SS) and front-to-back (FB) channels.

Clause 133. The system of any of clauses 119-132, wherein at least one of the training metrics and the validation metrics comprises metrics based on QRS width, and wherein the metrics comprise at least one of a standard deviation over time of an estimated width of QRS complexes and a mean over time of the estimated width of QRS complexes.

Clause 134. The system of any of clauses 119-133, wherein at least one of the training metrics and the validation metrics comprises metrics based on QRS height, and wherein the metrics comprise a standard deviation over time of an estimated height of QRS complexes.

Clause 135. The system of any of clauses 119-134, wherein at least one of the training metrics and the validation metrics comprises metrics based on at least one of QT variability, ST depression, elevation, and/or slope, T-wave alternant, T-wave variability, and dual lead T-wave morphology.

Clause 136. The system of any of clauses 119-135, wherein at least one of the training metrics and the validation metrics comprises heart sounds metrics.

Clause 137. The system of clause 136, wherein the heart sounds metrics comprise S3 and S4 heart sound metrics.

Clause 138. The system of any of clauses 119-137, wherein at least one of the training metrics and the validation metrics comprises electromechanical activation time metrics describing an interval from a first predetermined fiducial timepoint in the electrocardiograph (ECG) to a second predetermined fiducial timepoint in a subsequent mechanical activity of the heart.

Clause 139. The system of any of clauses 119-138, wherein the first predetermined fiducial timepoint in the ECG comprises an onset of P-wave and QRS complexes, wherein the onset of the P-wave and QRS complexes comprises timepoints relating to at least one of a) a Pwave, b) a Q-wave, c) an R-wave, and d) an S-wave.

Clause 140. The system of any of clauses 119-139, wherein the subsequent mechanical activity of the heart comprises left ventricular wall motion.

Clause 141. The system of any of clauses 119-140, wherein the second predetermined fiducial timepoint in the subsequent mechanical activity of the heart comprises at least one of a) a timepoint of maximal left ventricular wall motion, and b) a state of a relaxation of the left ventricular wall motion.

Clause 142. The system of any of clauses 119-141, wherein the second predetermined fiducial timepoint in the subsequent mechanical activity of the heart comprises a timepoint of peak intensity of the S1 heart sound.

Clause 143. The system of any of clauses 119-142, wherein the second predetermined fiducial timepoint in the subsequent mechanical activity of the heart is based on ultrasound measurements of the heart.

Clause 144. The system of any of clauses 119-143, wherein the electromechanical activation time metrics comprises a percent electromechanical activation time metric.

Clause 145. The system of any of clauses 119-144, wherein the classifying comprises calculating at least one of an area under a plotted curve of the time changing series of risk scores and a mean of the time changing series of risk scores.

Clause 146. The system of any of clauses 119-145, wherein the first and second risk scores are classified based on an amount that the first and second risk scores transgress the one or more thresholds.

Clause 147. The system of any of clauses 119-146, wherein the first and second risk scores are classified based on a number of times that the time changing series of risk scores transgress the one or more thresholds.

Clause 148. The system of any of clauses 119-147, wherein the one or more processors perform operations comprising: notifying at least one of the subject and a third party based on the classification of the first and second risk scores.

Clause 149. The system of any of clauses 119-148, wherein the classification of the first and second risk scores indicates at least one of an elevated risk and an immediate risk.

Clause 150. The system of any of clauses 119-149, wherein the notifying comprises sending a notification to at least one member of a medical team of the subject.

Clause 151. The system of any of clauses 119-150, wherein the one or more processors perform operations comprising: adjusting a time interval between detection of a cardiac event and a treatment for the cardiac event based on the classification of the first and second risk scores.

Clause 152. An external medical device comprising the medical premonitory event estimation system of any of clauses 119-151, wherein the external medical device is configured to monitor a cardiac condition of the subject.

Clause 153. The external medical device of clause 152, wherein the external medical device comprises a wearable medical device.

Clause 154. The external medical device of clause 152 or 153, wherein the one or more processors perform operations comprising: modifying one or more functions or features of a user interface of the external medical device based on the classification of the first and second risk scores.

Clause 155. A medical premonitory event estimation system, comprising: a nontransitory computer-readable storage medium in communication with one or more processors and having instructions stored thereon which, when executed by the one or more processors, cause the one or more processors to perform operations comprising: calculating an event estimation of risk score associated with a potential medical event for a subject, wherein the event estimation of risk score is calculated based on a machine learning classifier, wherein the machine learning classifier is trained on training metrics comprising at least one of i) cardiac electrophysiology metrics of a plurality of subjects and ii) at least one of demographic metrics and medical history metrics of the plurality of subjects.

Clause 156. The system of clause 155, wherein the machine learning classifier is validated based on a validation metrics independent from the training metrics, and wherein at least one threshold of the machine learning classifier is set based on the validation.

Clause 157. The system of clause 155 or 156, wherein the one or more processors perform operations comprising: classifying the event estimation of risk score based on at least one threshold.

Clause 158. The system of any of clauses 155-157, wherein the at least one threshold is substantially continuously refined based on a substantially continuously updated registry of metrics.

Clause 159. The system of any of clauses 155-158, wherein the one or more processors perform operations comprising: calculating a plurality of event estimation of risk scores associated with the potential medical event for the subject over a time series; and analyzing the plurality of event estimation of risk scores to determine at least one trend associated with the potential medical event for the subject over the time series.

Clause 160. The system of any of clauses 155-159, wherein at least one of the training metrics and the validation metrics comprises heart sounds metrics.

Clause 161. The system of any of clauses 155-160, wherein the heart sounds metrics comprise S3 and S4 heart sound metrics.

Clause 162. The system of any of clauses 155-161, wherein at least one of the training metrics and the validation metrics comprises electromechanical activation time metrics describing an interval from a first predetermined fiducial timepoint in the electrocardiograph (ECG) to a second predetermined fiducial timepoint in a subsequent mechanical activity of the heart.

Clause 163. The system of any of clauses 155-162, wherein the first predetermined fiducial timepoint in the ECG comprises an onset of P-wave and QRS complexes, wherein the onset of the P-wave and QRS complexes comprises timepoints relating to at least one of a) a Pwave, b) a Q-wave, c) an R-wave, and d) an S-wave.

Clause 164. The system of any of clauses 155-163, wherein the subsequent mechanical activity of the heart comprises left ventricular wall motion.

Clause 165. The system of any of clauses 155-164, wherein the second predetermined fiducial timepoint in the subsequent mechanical activity of the heart comprises at least one of a) a timepoint of maximal left ventricular wall motion, and b) a state of a relaxation of the left ventricular wall motion.

Clause 166. The system of any of clauses 155-165, wherein the second predetermined fiducial timepoint in the subsequent mechanical activity of the heart comprises a timepoint of peak intensity of the S1 heart sound Clause 167. The system of any of clauses 155-166, wherein the second predetermined fiducial timepoint in the subsequent mechanical activity of the heart is based on ultrasound measurements of the heart.

Clause 168. The system of any of clauses 155-167, wherein the electromechanical activation time metrics comprises a percent electromechanical activation time metric.

Clause 169. A medical premonitory event estimation method, comprising: acquiring a first set of physiological information of a subject received during a first period of time and based at least in part on a first ECG signal of the subject, and a second set of physiological information of the subject received during a second period of time; calculating first and second risk scores associated with estimating a risk of a potential cardiac arrhythmia event for the subject based on applying the first and second sets of physiological information to one or more machine learning classifier models trained on training metrics comprising at least one of i) cardiac electrophysiology metrics of a first plurality of subjects, and ii) at least one of demographic metrics and medical history metrics of the first plurality of subjects, wherein the one or more machine learning classifier models is validated on a validation metrics of a second plurality of subjects, and wherein one or more thresholds of the one or more machine learning classifier models is set based on the validation; providing at least the first and second risk scores associated with the potential cardiac arrhythmia event as a time changing series of risk scores; and classifying the first and second risk scores associated with estimating the risk of the potential cardiac arrhythmia event for the subject based on the one or more thresholds.

Clause 170. The method of clause 169, wherein the one or more thresholds comprise at least an elevated risk threshold and an immediate risk threshold, and wherein the classifying comprises for each of the first and second risk scores classifying the risk of the potential cardiac arrhythmia event for the subject as an elevated risk based on the first or second risk score transgressing the elevated risk threshold; and classifying the risk of the potential cardiac arrhythmia event for the subject as an immediate risk based on the first or second risk score transgressing the immediate risk threshold.

Clause 171. The method of clause 169 or 170, wherein the classifying comprises a time changing classification of the risk of the potential cardiac arrhythmia event for the subject based on the time changing series of risk scores.

Clause 172. The method of any of clauses 169-171, wherein the classifying comprises adjusting an underlying specificity of the one or more machine learning classifier models to reduce type 1 errors (false positives) in the underlying classification of the risk of the potential cardiac arrhythmia event for the subject.

Clause 173. The method of any of clauses 169-172, wherein the validation metrics comprises a plurality of one or more of cardiac electrophysiology metrics, demographic metrics, and medical history metrics of the second plurality of subjects.

Clause 174. The method of any of clauses 169-173, wherein at least one of the training metrics and the validation metrics comprises heart sounds metrics.

Clause 175. The method of any of clauses 169-164, wherein the heart sounds metrics comprise S3 and S4 heart sound metrics.

BRIEF DESCRIPTION OF THE DRAWINGS

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Further features and other objects and advantages will become apparent from the following detailed description made with reference to the drawings in which:

FIG. 8C illustrates an example ECG signal for determining a heart rate variability metric;

FIG. 8D illustrates an example of QRS width;

FIG. 8E illustrates an example of QRS height;

FIG. 8L shows state change results including sensitivity and specificity percentages for predicting medical premonitory events from an example testing set of two hundred patients;

FIG. 15 shows example physiological parameters that can be considered by the CAP application in computing a Modified Early Warning (MEW) score;

FIG. 16 shows example patient characteristics that can be considered in computing a Glasgow Coma Scale (GCS) score.

DETAILED DESCRIPTION

Figure 1:
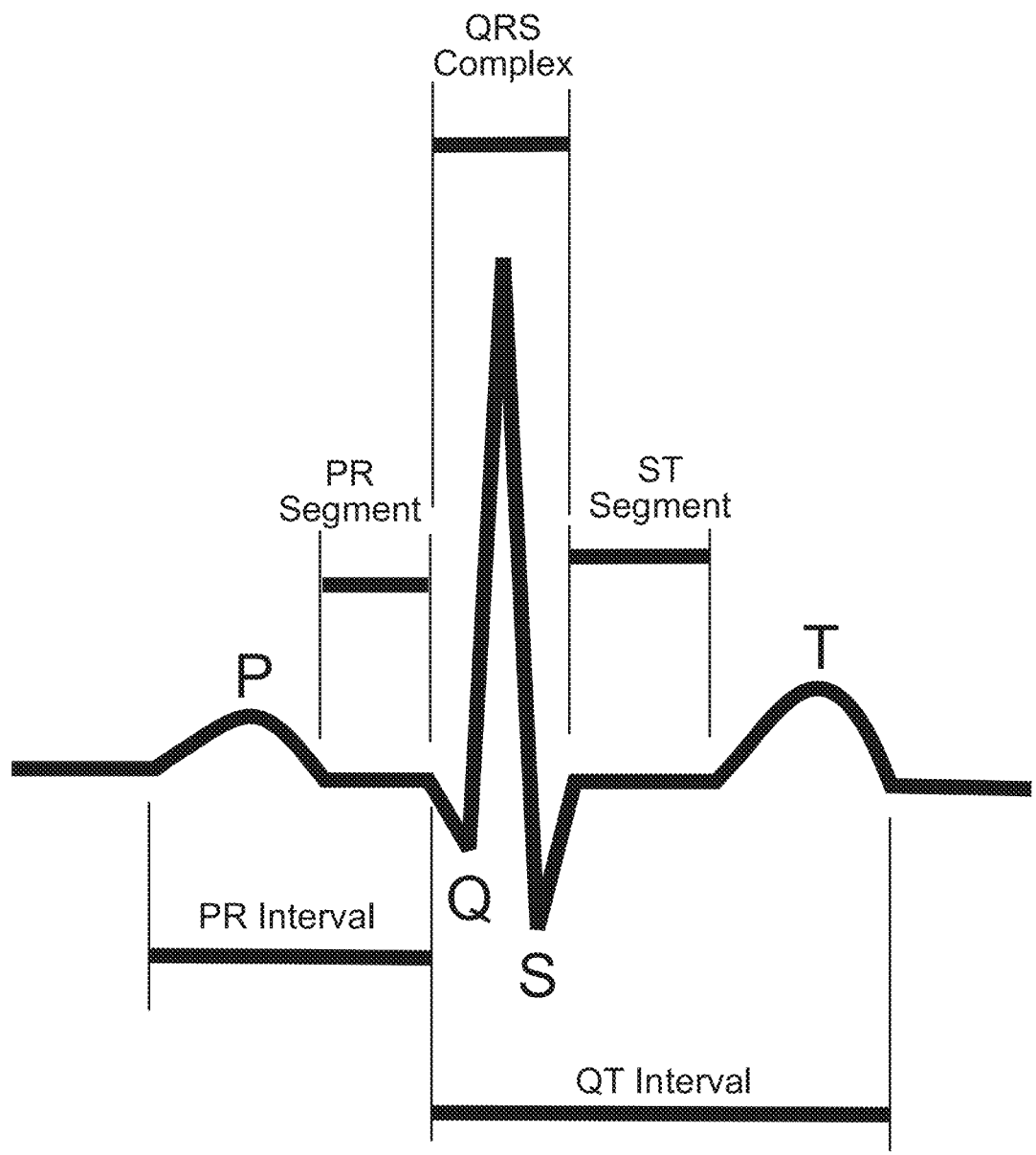
FIG. 1 is a graph of an example cardiac sinus rhythm electrocardiogram (ECG) signal.

Provided herein are improved systems and methods for automatically analyzing subject data to predict conditions including medical events, for example, adverse cardiac events, that may occur for a subject. One or more event estimation of risk scores can be generated that are based on an anticipated time of occurrence of the event. For example, for a plurality of time periods, an event estimation of risk score can be calculated (e.g., such that each time period has its own respective event estimation of risk score). In this way, multiple different event estimation of risk scores can be calculated for multiple different time periods, (e.g., less than about ten minutes, less than about one hour, less than about three hours, less than about one day, less than about one week, and/or less than about one month, etc.). The event estimation of risk scores provide a measure of the likelihood or probability of one or more medical event(s) occurring within the associated time period.

Event estimation of risk scores for one or more time periods can be compared to stored event estimation of risk thresholds associated with the corresponding time periods to determine a plan of action or response to the event. The plan of action or response may vary based on the predicted time to the event and/or the event estimation of risk score. Accordingly, a determined plan of action or a response for an event that is likely to occur in the more distant future may differ from a determined plan of action or a response for an event that is likely to occur in the more immediate future.

As used herein, the singular form of "a", "an", and "the" include plural referents unless the context clearly dictates otherwise.

As used herein, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention can assume various alternative orientations and, accordingly, such terms are not to be considered as limiting. Also, it is to be understood that the invention may assume various alternative variations and stage sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This may refer to a direct or indirect connection that may be wired and/or wireless in nature. Additionally, two units or components may be in communication with each other even though the data transmitted may be modified, processed, routed, and the like, between the first and second unit or component. For example, a first unit may be in communication with a second unit even though the first unit passively receives data, and does not actively transmit data to the second unit. As another example, a first unit may be in communication with a second unit if an intermediary unit processes data from one unit and transmits processed data to the second unit. It will be appreciated that numerous other arrangements are possible.

Generally, provided are systems and methods for automatically analyzing subject data to predict conditions including medical events, for example, adverse cardiac events. In some embodiments, systems and methods are provided for generating one or more event estimation of risk scores that are based on an anticipated time of the event. Event estimation of risk scores are sometimes referred to as cardiac arrest prediction (CAP) scores herein. In some embodiments, systems and methods are provided in which multiple different event estimation of risk scores are calculated for multiple different time periods, (e.g., less than about ten minutes, less than about one hour, less than about three hours, less than about one day, less than about one week, and/or less than about one month, etc.). The event estimation of risk scores provide a measure of the likelihood or probability of one or more medical event(s) occurring within the associated time period.

Systems and methods according to some embodiments may compare different event estimation of risk scores for the time periods to stored event estimation of risk thresholds associated with the time periods to determine a plan of action or response to the event that varies based on the predicted time to the event and/or the event estimation of risk score. Accordingly, a determined plan of action or a response for an event that is likely to occur in the more distant future may differ from a determined plan of action or a response for an event that is likely to occur in the more immediate future.

Non-limiting example methodologies for generally predicting patient outcomes based on various vital signs are described in U.S. Pat. No. 8,668,644, entitled "METHOD OF PREDICTING ACUTE CARDIOPULMONARY EVENTS AND SURVIVABILITY OF A PATIENT", filed Apr. 23, 2013; U.S. Pat. No. 8,932,220, entitled "METHOD OF PREDICTING ACUTE CARDIOPULMONARY EVENTS AND SURVIVABILITY OF A PATIENT", filed Mar. 6, 2014; U.S. Pat. No. 8,951,193, entitled "METHOD OF PREDICTING ACUTE CARDIOPULMONARY EVENTS AND SURVIVABILITY OF A PATIENT", filed Mar. 6, 2014; United States Patent Publication No. 2015/0223759, entitled "PREDICTING ACUTE CARDIOPULMONARY EVENTS AND SURVIVABILITY OF A PATIENT", filed Dec. 12, 2014; and PCT Patent Publication No. WO2011/115576, entitled "Method of predicting the survivability of a patient", filed Mar. 14, 2011; the entirety of all of which are incorporated by reference herein.

A time period may include any duration of time. For example, a time period may include a period of time from a current time to a future point of time, a period of time between two future points of time, an instant in time, and/or any combination thereof.

Systems and methods for detection and estimation of medical premonitory events based on various time periods are described herein. Systems and methods according to some embodiments provide varying suggested plans of action or responses based on the detection and estimation of medical premonitory events. A system for estimation and detection of medical premonitory events may be referred to herein as an "early warning system".

The Oxford English Dictionary defines "premonition" as "a strong feeling of something about to happen, esp. something unpleasant." The Latin roots of "premonition" are prae, before+monere, warn. As used herein, "premonitory" means an indication that something has a likelihood or probability of occurring, and a "medical premonitory event" means a medical event that has a likelihood or probability of occurring for a subject. The detection and estimation of medical premonitory events may thus be used as an early warning system to provide an individual and/or a medical professional time to prepare for a medical event, for example, to prepare for a potentially adverse or fatal degradation in the medical condition of a subject or patient, to potentially mitigate or avoid the adverse effects of the degradation, or even potentially completely avoid the degradation or event by timely, appropriate treatment.

Non-limiting examples of such medical events may include a cardiac event, such as a myocardial infarction or cardiac arrest, profound bradycardia due to acute decompensated heart failure, acute coronary syndrome, etc. Non-limiting examples of degradation in medical condition may include inception of a disease state, progression or worsening of a disease state, and/or an adverse medical event, such as arrhythmia, heart attack, a subject suffering from traumatic injury that undergoes a potentially fatal, rapid loss in blood pressure due to hard-to-detect internal bleeding. Other possible medical events or degradations in the medical condition of a subject may be due to physical injury, diabetes, septic shock, seizure or epilepsy, for example.

Non-limiting examples of cardiac premonitory events may include tangible events that are viewable by a trained clinician, such as ectopic beats, runs of ectopic beats, ventricular tachycardia, bradycardias, and/or irregularities or abnormalities in P wave, QRS complex, Twave and U wave. For example, irregularities or abnormalities in electrical activity of the heart can include flattened T waves, inverted T waves, hyper-acute T waves or peaked T waves, beatto-beat T wave variability, shortened QT interval, prolonged QT interval, wide QRS, prominent U waves, etc. Alternatively or additionally, medical premonitory events may include intermediate level events, such as the detection of clusters of events, accelerations of event rates, an increase in intensity or criticality of events, etc. Alternatively or additionally, medical premonitory events may include higher order events that may, for example, be defined in a multidimensional parameter space, e.g., the parameters comprising electrocardiogram ("ECG") data and/or other relevant physiologic parameters and/or subject demographics and other health history. Non-limiting examples of premonitory events are discussed in further detail below.

Systems and methods are detailed herein and often described with respect to subjects who may be at risk of a cardiac event; however, disclosed embodiments are not limited only to cardiac events. Systems and methods described herein may be used for detection and estimation of any medical premonitory event based on any monitored physiological parameter of a subject.

Subjects who may be at risk of a cardiac event, for example, cardiac arrest, ventricular tachycardia ("VT"), ventricular fibrillation ("VF"), pulseless electrical activity ("PEA"), asystole, etc. may be monitored for indications of an oncoming cardiac event so that actions may be taken to reduce the probability of the occurrence of the cardiac event and/or mitigate harm to the subject due to the cardiac event. An event estimation of risk score can be determined for any combination of such cardiac events. The subjects to be monitored may include subjects that have experienced a cardiac event in the past, subjects that are recovering from cardiac or other surgery, and/or subjects that have indicated other signs of possible cardiac dysfunction, for example, an otherwise unexplained loss of consciousness, rapid heartbeat, or chest pain.

An external medical device as described herein can include but is not limited to one or more cardiac sensing electrodes, a controller, and a user interface. The cardiac sensing electrode monitors cardiac electrophysiology and can be used to obtain electrocardiogram records such as the p, q, r, s, t, and u waves as well as premature ventricular contraction, tachyarrhythmia and changes to heart wave morphology. These electrocardiogram records along with related information derived from the heart rhythm data can be used alone or in combination with demographic and medical history to classify a subject for elevated risk of sudden cardiac death which may result from sudden cardiac arrest or asystole. The controller can be adjusted to analyze a combination of cardiac electrophysiology and subject data, including information garnered from electrocardiogram recordings of several hours to as little as 45 seconds or less. Electrocardiogram recordings can be obtained once per subject or multiple times during the course of a subject's wearing the device. For example, in implementations involving multiple recordings, a time dependent measure of changes to risk classification of sudden cardiac death can be obtained. The user interface can provide a visual display screen with audio and vibrational components, as well as cellular and wireless internet connectivity, any or all of which can be used as a means to provide a summary of risk information to the subject, first responder, or medical professional.

In an implementation, systems, methods, and devices as described herein can be used for classifying subjects by risk for sudden cardiac death, e.g., based on event estimation of risk scores. For example, the principles described herein may be implemented in cardiac monitoring and/or therapeutic devices. For instance, at least one embodiment relates generally to a cardiac monitoring device used, for example, in mobile cardiac telemetry (MCT) and/or continuous event monitoring (CEM) applications.

In some implementations, at least one embodiment relates generally to a wearable therapeutic device, and more specifically to a wearable therapeutic device configured to monitor a subject's cardiac electrophysiology. An embodiment incorporates the subject's electrocardiogram along with demographic information and medical history (such as gender, age, left ventricular ejection fraction, co-morbidities and cardiac indications leading to prescription of the wearable therapeutic device). In some embodiments, the likelihood that a subject will retain, for a prolonged period of time from months to years, one or more risk metrics associated with sudden cardiac death is evaluated. For example, the subject may be evaluated for the long term risk of retaining reduced left ventricular ejection fraction (e.g., 5%) or the likelihood that he or she will continue to exhibit premature ventricular contractions, tachyarrhythmia or variable heart wave morphology.

Parameters or metrics of a subject that may be monitored include various parameters of the subject's ECG. ECG parameters may include, for example, changes to the T-wave such as T-wave alternans or T-wave lability (e.g., morphological changes in the T-wave not limited to alternating beats, but occurring every, e.g., third, fourth, fifth, etc. beat), PR interval, QT interval, QRS complex, heart rate variability (HRV), and/or other parameters of the ECG of a subject. Portions of an ECG signal corresponding to these parameters or metrics are illustrated in, for example, FIGS. 1 and 8B-E, and may be monitored non-invasively, such as by an ECG monitor or an automated external defibrillator (AED) when an ECG monitor or device of similar function is included.

A non-exhaustive list of other measurable parameters or metrics of a subject that may be predictive of an impending cardiac event may include a low and decreasing heart rate, (i.e., bradycardia, commonly referred to as "Bradying down"), increased heart rate, blood pressure, tidal $CO_2$, (i.e., the concentration or partial pressure of carbon dioxide in the respiratory gases of the subject), $SpO_2$, (i.e., a measure of blood oxygen saturation), $SMO_2$, (i.e., a measure of muscle oxygen saturation), cerebral blood flow, electroencephalography (EEG) signals, electromechanical activation time (EMAT) (as described in further detail below), heart sounds (e.g., S3 and S4 sounds), brain oxygen level, (i.e., cerebral oximetry), tissue pH, ultrasound images of the subject's heart, and a reaction of the subject's heart rate to tilting of the subject.

Parameters of a subject that may be monitored for an indication of an oncoming cardiac event may be monitored invasively or non-invasively, and many parameters of the subject may be monitored using optical techniques. For example, sublingual $CO_2$, brain oxygen level and tissue pH may be measured optically.

Measurable parameters or metrics based on heart sounds may include acoustic cardiographic metrics derived from acquisition and quantitative measurements of combined ECG and cardiac acoustical data. Such metrics can include those that identify and quantify normal and abnormal heart sounds, e.g., related to the left ventricle, and indicate the timing of those heart sounds in every cardiac cycle versus the onset of the P wave and QRS complexes in a substantially simultaneously recorded ECG. For example, such metrics may indicate the presence and strength of heart sounds (such as the S3 and S4) and the duration of systolic time intervals.

In some examples, such acoustic and/or combined acoustic and ECG metrics can include electromechanical activation time (EMAT) metrics. For example, EMAT metrics as used herein describe an interval from some fiducial timepoint in the electrocardiograph (ECG) to some fiducial timepoint in a subsequent mechanical activity of the heart. One example of a fiducial timepoint in the ECG is an onset of the P-wave and QRS complexes such as the P-wave, Q-wave, R-wave, or S-wave.

An example of a mechanical activity of the heart may be a valve closure, e.g., the closure of the aortic valve. In some examples, the mechanical activity may be left ventricular wall motion, and the fiducial timepoint may be the timepoint of maximal left ventricular wall motion, or the fiducial timepoint might be the start of relaxation. The fiducial timepoint in a subsequent mechanical activity of the heart may be measured by heart sounds, as exemplified by AUDICOR® Technology from Inovise Medical of Beaverton, Oreg., or using ultrasound measurements of ventricular or valvular motion. In some implementations, an example of the fiducial timepoint in a subsequent mechanical activity of the heart may be the timepoint of peak intensity of the S1 heart sound.

For example, such EMAT metrics can provide a measure of an amount of time that the left ventricle may need to generate sufficient force to close the mitral valve. In cases involving systolic heart failure, for example, an EMAT measure may be prolonged.

For example, one EMAT metric includes percent EMAT (% EMAT), which may be computed as the EMAT time measure divided by a measure of a dominant RR interval. The % EMAT metric relates to an efficiency of the cardiac pump function. For example, in some cases, % EMAT>15% may be predictive of a patient's likelihood for developing heart failure related complications (e.g., re-hospitalization may be needed), as described in Chao T et al. EMAT in the Prediction of Discharge Outcomes in Patients Hospitalized with AHFS. Internal Med. 2010, 49: 2031-2037.

Further, a shortened EMAT measure may correlate with an increased contractility and short electromechanical delays as described in Efstratiadis S et al. Computerized Acoustic Cardiographic Electromechanical Activation Time Correlates with Invasive and Echocardiogrpahic Parameters of LV Contractility. J of Card. Failure. 2008, 14(7):577-582. As described above, S3 and S4 heart sounds metrics may be used in certain predictive models described herein, e.g., for estimating risks scores associated with certain outcomes. For example, S3 and S4 heart sound metrics may be predictive of worsening heart failure. Accordingly, S3 and S4 metrics may be included along with other metrics input into the predictive models described herein. In accordance with the principles described herein, S3 and/or S4 may be predictive of a need for increasing medicine or preparing for hospitalization relating to myocardial infarction and/or heart failure complications.

For example, in adults (e.g., of about age 40 or above), S3 metrics may be used to indicate a correlation with dysfunction or volume overload of the ventricles. Examples of related conditions include valvular regurgitation, high-output states, left-to-right intracardiac shunts, complete A-V block, renal failure, and volume overload from excessive fluids or blood transfusion. In an implementation, S3 may indicate congestive heart failure caused by volume overload (excessive fluids). For example, an S3 sound can be detected when volume overload is severe. In some implementations, the presence of S3 may be predictive of increased risk for sudden death due to, e.g., cardiac muscular stretch. In some situations involving high risk scores and the presence of S3, for example, a caregiver may wish to respond by adding or increasing diuretics.

S4 metrics can indicate an increase in heart filling pressure, e.g., an increased resistance to filling of the left or right ventricle because of a reduction in ventricular wall compliance, and it can be accompanied by a disproportionate rise in ventricular end-diastolic pressure. For example, S4 in individuals of about age 50 or more may be predictive of patients with or worsening systemic hypertension, aortic stenosis, hypertrophic cardiomyopathy and coronary heart disease.

For example, S4 may become evident, or its intensity may be augmented, during episodes of angina pectoris. For example, the presence of S4 may indicate early stages of acute myocardial infarction, which may occur with or without signs of heart failure. In situations involving high risk scores and presence of S4, for example, a caregiver may wish to respond by treating angina (ischemia) with increasing daily medicine or episodic medicine (e.g., nitrates).

In some implementations, the predictive models described herein can use heart sound metrics, e.g., for estimating risks scores associated with certain outcomes, by comparing a patient's heart sounds to a baseline model. For example, if the patient's heart sounds deviate from the baseline model, the predictive models may determine that the heart sounds are abnormal and thus may be predictive of an adverse event (e.g., predictive of a shock being delivered). The degree by which the patient's heart sounds deviate from the baseline model may correspond to the effect on the patient's risk scores. For example, heart scores that drastically deviate from the baseline model may have a relatively larger effect on the patient's risk scores than heart scores that minimally deviate from the baseline model.

In some implementations, heart sounds may be sampled as ten second snapshots. The ten second snapshot can be sampled every five minutes during a four hour period. For example, the ten second snapshots can be sampled every five minutes during night time hours (e.g., from midnight until 4 AM) everyday, totaling 48 snapshots that are collected per day. A snapshot can include side-to-side (SS) and front-to-back (FB) ECG signals. In some implementations, a snapshot can also include x-, y-, and z-accelerometer signals.

Templates (e.g., generic representations of sampled data) can be built from the snapshots measured on a first day of use of the medical devices described herein. The baseline model may be based on patient heart sounds (e.g., patient heart sounds that are measured on a first day of use of the medical device). For example, the baseline model may include a subset of the templates that are built. A template can be built from each of the snapshots; 48 templates can be built from the 48 snapshots. An algorithm can be used (e.g., a heart sound templating algorithm) to build the templates based on the snapshots. The heart sound templating algorithm can build the templates by considering the heart sound samples, SS and FB ECG signals, and the accelerometer signals. The heart sound templating algorithm can also calculate a similarity from one template to another template, which may be represented as a scalar value between 0 and 1, as describe in more detail below. In some implementations, a subset of templates (e.g., representative templates) can be chosen from the 48 templates such that the representative templates make up the baseline model.

Figure 13:
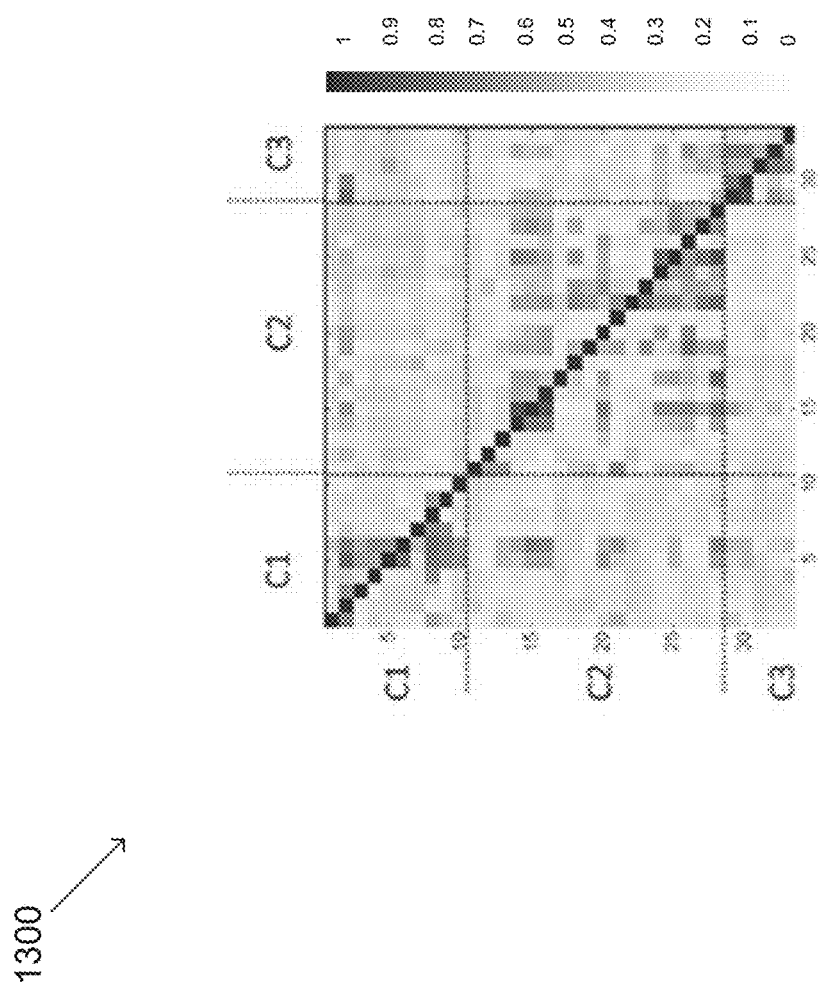
FIG. 13 shows an example of a similarity matrix illustrating K-means clustering performed over accelerometer signals.

In some implementations, the representative templates can be chosen from the 48 templates based on a signal-to-noise ratio (SNR) of the templates. For example, templates having a low SNR may be discarded. The remaining templates can then be separated into multiple clusters. For example, the remaining templates may be separated into three clusters, with each cluster corresponding to a body position (e.g., supine, lying on left side, lying on right side). The body position may be determined based on the x-, y-, and z-accelerometer signals. For example, referring to FIG. 13, K-means clustering can be performed over accelerometer signals corresponding to each template to separate the templates into three clusters (e.g., $C_1$, $C_2$, and $C_3$). The similarity matrix 1300 of FIG. 13 shows the three clusters $C_1$, $C_2$, $C_3$ represented by groups of rows and columns. The numerical identifiers of the rows and columns each identify a possible template that is composed of a plurality of samples. The similarity between the various possible templates is represented as a scalar value between 0 and 1 and expressed as a color in the similarity matrix 1300, such that relatively darker colors in the similar matrix 1300 correspond to templates that have a relatively high degree of similarity. Each possible template can be compared to the samples that make up each other template. For example, when the template having a numerical identifier of "1" on the x-axis is compared to the samples of the template having a numerical identifier of "33" on the y-axis, the degree of similarity is relatively low (e.g., the corresponding color is light gray). On the other hand, when the template having a numerical identifier of "1" on the x-axis is compared to the samples of the template having a numerical identifier of "2" on the y-axis, the degree of similarity is relatively high (e.g., the corresponding color is dark gray). When the template having a numerical identifier of "1" on the x-axis is compared to the samples of the template having a numerical identifier of "1" on the y-axis (e.g., when a template is compared to the same samples that make up the template), the degree of similarity has the highest possible value (e.g., the corresponding color is black).

A representative template can be chosen for each of the clusters. In some implementations, a template that has the largest mean similarity with the other templates in the cluster can be chosen as the representative template for that cluster. For example, for clusters $C_i$ (i=1, 2, 3), the representative templates $M=\{\tau_1', \tau_2', \tau_3'\}$ can be chosen according to the following Equations (1), (2), and (3):

$$\tau'_i = \underset{\tau \in C_i}{\mathrm{argmax}}\, Q(C_i \mid \tau) \qquad (1)$$

$$Q(C_i \mid \tau) = \frac{1}{|C_i|-1} \sum_{v \in C_i - \tau} g(v \mid \tau) \qquad (2)$$

$$g(v \mid \tau): \text{similarity function} \qquad (3)$$

In some implementations, once the baseline model is established, an abnormality metric can be determined for each of the snapshots (e.g., the 48 snapshots) that are collected per day. In some implementations, snapshots that have a low SNR are discarded, and thus fewer than 48 abnormality metrics may be determined. For each snapshot, the abnormality metric may be determined based on a degree of similarity between a templates derived from the snapshot and the baseline model (e.g., the corresponding representative template).

A snapshot can be identified as being low SNR (and, e.g., can be accordingly discarded) if the SNR is less than 3 dB. The SNR of a snapshot can be determined based on an algorithm (e.g., a heart sound templating algorithm).

Figure 2:
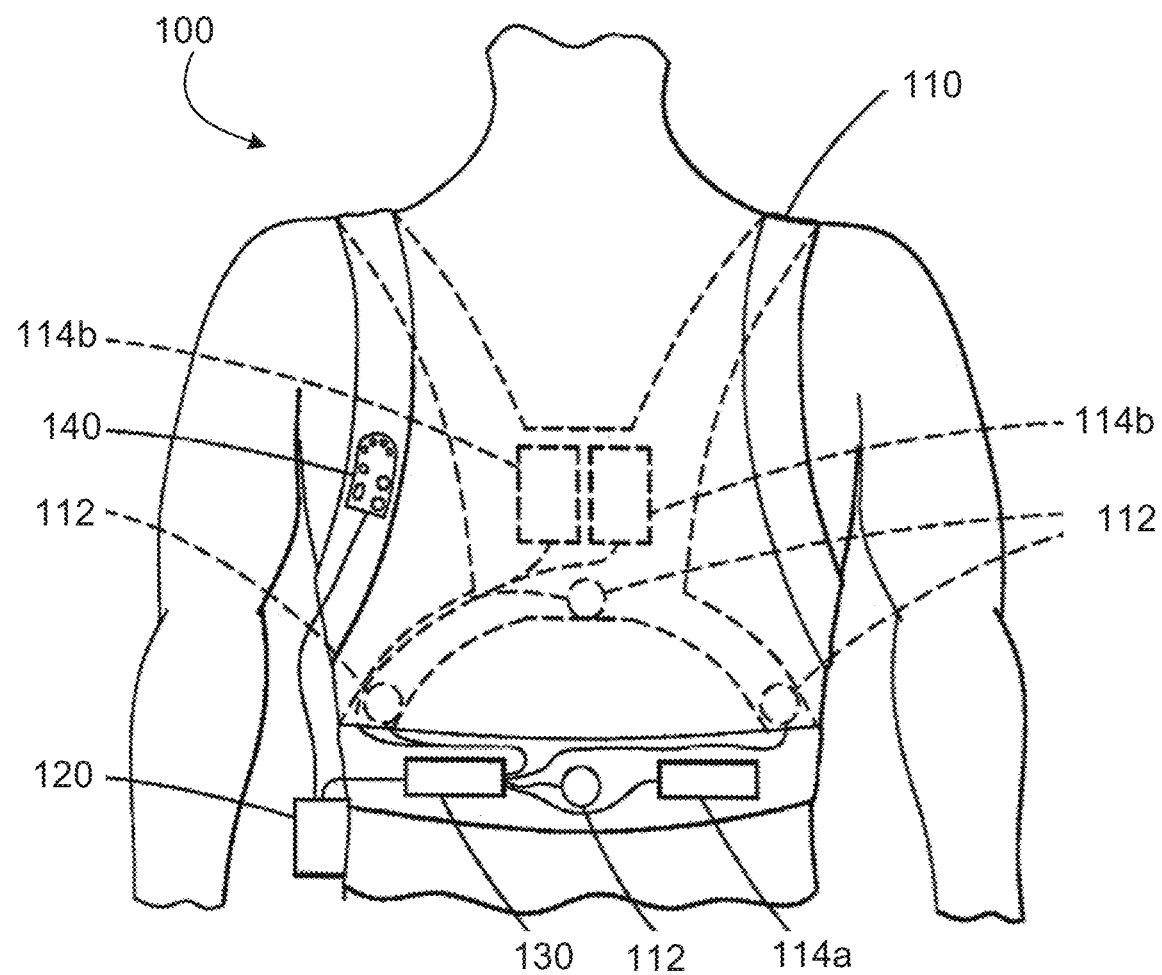
FIG. 2 shows a wearable medical device.

Sensors for monitoring any one or more of the parameters of a subject listed herein, which may provide an indication of an oncoming cardiac event, may be included in a medical device, for example, a wearable medical device or as part of an AED or other form of monitoring or life support device. The medical device may be portable or wearable by a subject, or stationary or affixed to a support. FIG. 2 illustrates a wearable medical device according to one non-limiting embodiment, which is similar to a LifeVest® wearable cardioverter defibrillator available from ZOLL Medical Corporation of Chelmsford, Mass., and which may include sensors for monitoring parameters of a subject which may be predictive of an oncoming cardiac event. Non-limiting examples of suitable wearable defibrillators are disclosed in U.S. Pat. Nos. 4,928,690; 5,078,134; 5,741,306; 5,944,669; 6,065,154; 6,253,099; 6,280,461; 6,681,003; 8,271,082; and 8,369,944; the entirety of all of which are incorporated by reference herein. Disclosed embodiments, however, are not limited to wearable medical devices, and a medical device for monitoring any one or more of the parameters of a subject listed herein may include an implantable medical device, a stationary device, such as those that are used in a hospital or bedside setting, such as a defibrillator or monitor, a portable medical device, such as an automated external defibrillator or mobile cardiac outpatient telemetry ("MCOT") device or other monitor of physiological parameters of a subject.

As shown in FIG. 2, in some embodiments the wearable medical device 100 includes a harness 110 having a pair of shoulder straps and a belt that is worn about the torso of a subject. The wearable medical device 100 includes a plurality of ECG sensing electrodes 112 that are attached to the harness 110 at various positions about the subject's body during use and electrically coupled to a control unit 120 via a connection pod 130. The plurality of ECG sensing electrodes 112, which may be dry-sensing capacitance electrodes, are used by the control unit 120 to monitor the cardiac function of the subject and may include a front/back pair of ECG sensing electrodes and a side/side pair of ECG sensing electrodes. Additional ECG sensing electrodes and/or other sensors may be provided, and the plurality of ECG sensing electrodes 112 may be disposed at varying locations about the subject's body.

The wearable medical device 100 includes a plurality of therapy electrodes 114a, 114b that are electrically coupled to the control unit 120 via the connection pod 130 and which are capable of delivering one or more therapeutic defibrillating shocks to the body of the subject, if it is determined that such treatment is warranted. The plurality of therapy electrodes 114a, 114b may include a first therapy electrode 114a that is disposed on the front of the subject's torso and a second therapy electrode 114b that is disposed on the back of the subject's torso. The second therapy electrode 114b includes a pair of therapy electrodes that are electrically coupled together and act as the second therapy electrode 114b. The use of two therapy electrodes 114a, 114b permits a biphasic shock to be delivered to the body of the subject, such that a first of the two therapy electrodes may deliver a first phase of the biphasic shock with the other therapy electrode acting as a return, and the other therapy electrode may deliver the second phase of the biphasic shock with the first therapy electrode acting as the return. The connection pod 130 electrically couples the plurality of ECG sensing electrodes 112 and the plurality of therapy electrodes 114a, 114b to the control unit 120, and may include various electronic circuitry. For example, the connection pod 130 may include signal acquisition circuitry, such as a plurality of differential amplifiers to receive ECG signals from different ones of the plurality of ECG sensing electrodes 112 and to provide a differential ECG signal to the control unit 120 based on the difference therebetween. The connection pod 130 may include other electronic circuitry, such as a motion sensor (e.g., an accelerometer and/or a gyroscope) by which subject activity may be monitored.

As shown in FIG. 2, the wearable medical device 100 includes a user interface pod 140 that is electrically coupled to the control unit 120. The user interface pod 140 may be attached to the subject's clothing or to the harness 110, for example, via a clip (not shown) that is attached to a portion of the interface pod 140. Alternatively, the user interface pod 140 may simply be held in a hand of the subject or other person. The user interface pod 140 may communicate wirelessly with the control unit 120, for example, using a Bluetooth®, Wireless USB, ZigBee, Wireless Ethernet, GSM, or other type of communication interface. The user interface pod 140 typically includes a number of buttons or a touch screen by which the subject or a bystander may communicate with the control unit 120, and a speaker and/or a display by which the control unit 120 may communicate with the subject or the bystander. For example, if the control unit 120 determines that the subject is experiencing a cardiac arrhythmia, the control unit 120 may issue an audible alarm via a loudspeaker (not shown) on the control unit 120 and/or the user interface pod 140 alerting the subject and any bystanders to the subject's medical condition. The control unit 120 may also instruct the subject to press and hold one or more buttons on the control unit 120 or on the user interface pod 140 to indicate that the subject is conscious, thereby instructing the control unit 120 to withhold the delivery of one or more therapeutic defibrillating shocks. If the subject does not respond, the device may presume that the subject is unconscious, and proceed with the treatment sequence, culminating in the delivery of one or more defibrillating shocks to the body of the subject. In some embodiments, functionality of the user interface pod 140 may be integrated into the control unit 120.

The control unit 120 includes at least one processor, microprocessor, or controller, such as a processor commercially available from companies such as Texas Instruments, Intel, AMD, Sun, IBM, Motorola, Freescale and ARM Holdings. The at least one processor of the control unit 120 is configured to monitor the subject's medical condition, to perform medical data logging and storage, and to provide medical treatment to the subject in response to a detected medical event, such as a cardiac arrhythmia.

Although not shown, the wearable medical device 100 may include additional sensors, other than the ECG sensing electrodes 112, capable of monitoring the physiological condition or activity of the subject. For example, sensors capable of measuring blood pressure, heart rate, thoracic impedance, pulse oxygen level, respiration rate, heart sounds, lung sounds, tidal $CO_2$, $SMO_2$, cerebral blood flow, EEG signals, brain oxygen level, tissue pH, ultrasound images of the subject's heart, and the activity level of the subject may also be provided.

The wearable medical device 100 may include functionality to administer treatments or interventions in addition to or as an alternative to defibrillation. The additional or alternative treatments or interventions may include pacing of a subject's heart, automated administration of chest compression with an apparatus similar to the AutoPulse® non-invasive cardiac support pump available from ZOLL Medical Corporation of Chelmsford, Mass., and/or automated drug delivery. The portion of the wearable medical device 100 that provides defibrillation or other therapy may be detachable from the control unit 120. By making the control and therapy units modular, the wearable medical device 100 may be worn without the defibrillation portion attached, thus making the wearable medical device 100 smaller, lighter and more comfortable for the subject. A subject who is wearing the wearable medical device 100 without the defibrillator portion, for example, when they are in the shower or swimming, may attach the defibrillator portion when instructed by the wearable medical device 100. A wearable medical device 100 that does not include the defibrillator portion is sometimes referred to as a monitoring device.

Figure 3:
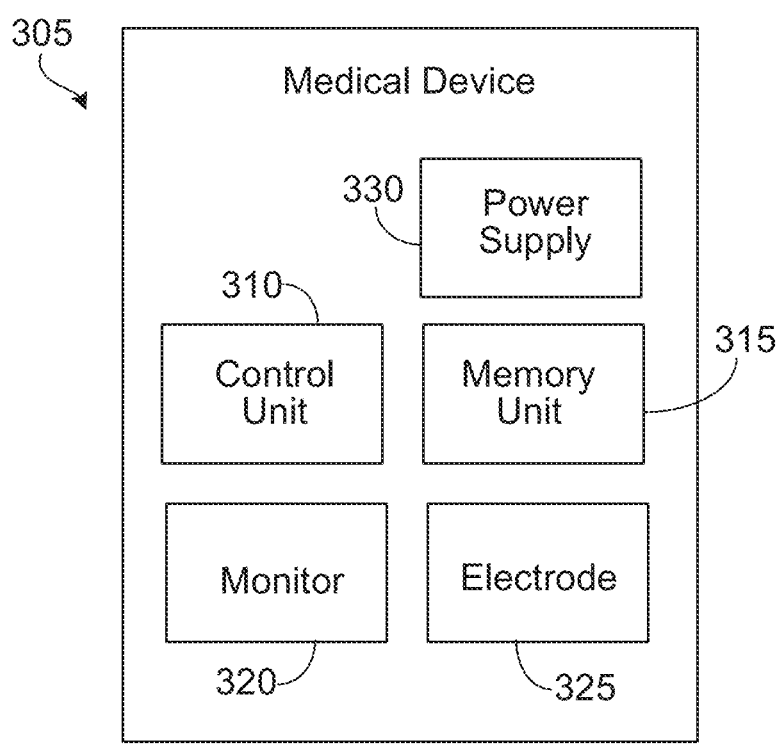
FIG. 3 is a block diagram of a medical device.

FIG. 3 is a block diagram of a medical support device 305 which may include sensors for monitoring parameters of a subject to estimate the risk of a medical event occurring. The medical support device 305 may include a life support device, for example, at least one Basic Life Support (BLS) device or Advanced Life Support (ALS) device such as a defibrillator or an AED. The life support device 305 may be part of an external defibrillator or pacing device such as the AED Pro or AED Plus defibrillator, LifeVest®, ProPack M.D., X Series defibrillators, M Series defibrillators, R Series defibrillator BLS, or E Series defibrillator manufactured by the ZOLL Medical Corporation of Chelmsford Mass. The medical support device 305 need not be a wearable defibrillator or other therapeutic device, but may be an Automated External Defibrillator (AED).

The medical support device 305 may be designed to be operated by a person with little or no medical training, prompt a user with a series of instructions to treat a subject, and prevent the user from deviating from the instructions. For example, the medical support device 305 may determine a power level of a defibrillation shock to be applied to the subject, and prevent the user from adjusting the power of the defibrillation shock. The user can follow instructions to couple the medical support device 305 to the subject, for example, by placing electrodes as instructed on the subject or by turning on the medical support device 305, and the medical support device 305 can automatically determine a treatment to be applied to the subject. In some embodiments, the medical support device 305 may include functionality adapted for use by a user with specialized medical training, such as an ALS provider, a doctor, or an emergency medical technician. For example, the medical support device 305 may be responsive to user input. The user may override treatment suggested by the medical support device 305, or modify a power level, pulse width, pulse type, (e.g., monophasic or biphasic), or other parameter of the defibrillation shock or intervention to be applied to the subject.

The medical support device 305 may include a pacing unit or a monitoring device that records health related information from a subject, such as information about the subject's respiration rate or heart activity. The medical support device 305 may include an electrocardiograph that displays a subject's ECG. The medical support device 305 may be carried by paramedics, emergency health care providers, or first responders, such as police or firemen, or may be the type of life support device that is provided by a business or common carrier, e.g., an airline or bus, for use in an emergency situation. These or other users can couple the medical support device 305 with a subject to monitor the subject to diagnose a condition, e.g., cardiac arrest, arrhythmia, etc., or to apply treatment to the subject, e.g., defibrillation therapy, pacing therapy, etc.

The medical support device 305 includes at least one control unit 310 including one or more processors that controls operation of the medical support device 305. For example, the control unit 310 may direct the medical support device 305 to monitor the medical status of a subject or apply treatment to the subject. The medical support device 305 may include at least one memory unit 315. The memory unit 315 may be coupled to the control unit 310 and can store monitored information of the subject, such as ECG data or the subject's respiration rate. The memory unit 315 may store current and/or historical information about the subject, information about the subject's age, weight, health, or gender, and/or information about past treatment applied by the medical support device 305 to the subject. The stored information may include the date and time at which treatment was applied to the subject and the nature of the treatment, e.g., the pulse width, amplitude, energy level of the treatment, whether monophasic or biphasic pulses were delivered, etc.

The medical support device 305 may include at least one display monitor 320. The monitor 320 may be coupled to the control unit 310 and the memory unit 315 and display information about the subject, such as the subject's ECG, heart rate, and/or respiration rate. The monitor 320 may display other information about the subject, e.g., age, weight, etc., and indicate treatments that have been applied to the subject and times at which the treatments were applied. The monitor 320 may indicate that treatment is being applied to the subject during the application of the treatment by the medical support device 305. For example, the monitor 320 may display a warning that an electric shock is about to be applied or is being applied to the subject by medical support device 305. The warning may be a visual, audio, and/or tactile warning. The monitor 320 may include a user interface that a user, e.g., the subject or a first responder, of the medical support device 305, may use to input information, such as information about the subject's health, appearance, age, weight, and/or gender. The user input information may be stored in the memory unit 315.

The medical support device 305 includes at least one electrode 325. The at least one electrode 325 may include one or more sensing electrodes that can monitor the subject and detect ECG information, respiration information, and/or other information about the subject's condition. The at least one electrode 325 may include one or more therapy electrodes that apply treatment to the subject, such as to administer pacing signals or a defibrillation shock. The at least one electrode 325 may include sensing electrodes and therapy electrodes as discrete electrodes, or combined into an integrated sensing/therapy electrode assembly. The at least one electrode 325 may be an external electrode that may be placed on a subject's body.

The medical support device 305 includes at least one power supply 330. The at least one power supply 330 may include batteries or other power supplies, including AC power supplies and uninterruptible power supplies. The at least one power supply 330 provides power to the medical support device 305, including the control unit 310, the memory unit 315, the monitor 320, and the at least one electrode 325.

Although not shown, the medical support device 305 may include additional sensors, other than the electrode 325, which are capable of monitoring the physiological condition or activity of the subject. For example, sensors capable of measuring blood pressure, heart rate, thoracic impedance, pulse oxygen level, respiration rate, heart sounds, lung sounds, tidal $CO_2$, $SMO_2$, cerebral blood flow, EEG signals, brain oxygen level, tissue pH, ultrasound images of the subject's heart, and the activity level of the subject may be provided.

The medical support device 305 may include functionality to administer treatments or interventions in addition to or as an alternative to defibrillation. These additional or alternative treatments or interventions may include, for example, pacing of a subject's heart, automated administration of chest compression, and/or automated drug delivery.

The medical support device 305 may include functionality to determine a type of cardiac event that a subject is experiencing or a type of cardiac event that may be imminent. The medical support device 305 may determine an appropriate treatment or intervention for the type of cardiac event and may automatically administer the appropriate treatment or intervention to the subject. If the medical support device 305 is used in combination with another type of life support device, such as an electromechanical chest compression device, e.g., a ZOLL AutoPulse® cardiac support pump, the medical support device 305 may communicate the recommended intervention to the other life support device.

If the cardiac event is one for which the wearable medical device 100 or the medical support device 305 determines that it is incapable of administering an appropriate treatment or intervention, or if the cardiac event is one for which no treatment or intervention may be effective in treating, the wearable medical device 100 or the medical support device 305 may call for assistance, for example, by emitting an audio or visual indication of a need for assistance and/or by placing a call over a cellular network to, for example, a physician or emergency medical response system. The wearable medical device 100 or the medical support device 305 may provide an indication of the appropriate treatment or intervention to a responder, for example, visually via a display on the user interface 140 or monitor 320, and/or audibly via a speaker on the control unit 120 or control unit 310, if the wearable medical device 100 or the medical support device 305 determines that it is incapable of administering the appropriate treatment or intervention itself.

Various parameters of a subject may be predictive of various cardiac events and may provide various amounts of time prior to the predicted cardiac event during which a treatment provider, such as rescuer or physician, may take action or provide treatment to reduce the probability of the occurrence of the cardiac event and/or mitigate harm to the subject by the cardiac event or other medical event. For example, if it is observed that the QRS complex of a subject's ECG is widening or that the heart rate of the subject is decreasing, there may be a relatively long precursor time prior to a predicted cardiac event during which a rescuer may take action. In another example, changes to the T-wave of a subject's ECG may occur between about 15 and about 30 seconds prior to the onset of VF. T-wave alternans (a periodic beat-to-beat variation in the amplitude or shape of the T-wave) may be indicative of impending VT or cardiac arrhythmia. Alternative measures, estimation and detection methods, as described herein, may also be employed by the medical support device 305 to predict and respond to different cardiac events.

Various parameters of a subject which may be predictive of an impending or occurring cardiac event may call for various actions or responses to be taken by the wearable medical device 100 or the medical support device 305, the subject, and/or a bystander or medical professional. For example, if the tidal $CO_2$ or cerebral blood flow of a subject fails to satisfy a threshold level, or if analysis of a subject's EEG by the control unit 120 or control unit 310 indicates that the subject's brain is not receiving adequate oxygen, it may be indicative that the subject's heart is pumping but cannot deliver enough blood to itself and/or other portions of the subject's body. If left untreated, a subject showing a drop in tidal $CO_2$ or cerebral blood flow may exhibit a reduction in heart rate. An appropriate response to a drop in tidal $CO_2$ or cerebral blood flow of a subject may be to initiate CPR. If a subject exhibits changes to the ECG T-wave, it may be appropriate to initiate chest compressions. If a subject exhibits heart rhythm but no pulse, for example, pulseless electrical activity (PEA), administration of CPR and/or drugs until the subject exhibits return of spontaneous circulation (ROSC) may be appropriate.

If action is not taken quickly enough or if the action taken in response to a parameter indicating a probability of an impending cardiac event is not effective, the subject may experience the cardiac event. Some types of cardiac events, for example, early stage VF and some types of VT are appropriately treatable by electrical shock (defibrillation). Other types of cardiac events, for example late stage VF (VF that has been occurring for more than about four or five minutes) may be appropriately treated by CPR, possibly followed by defibrillation, but may not be appropriately treated initially by defibrillation. Other types of cardiac events, for example, acute myocardial infarction may be appropriately treated by administration of a thrombolytic agent or other type of drug, accompanied by CPR. Some types of cardiac events, for example, asystole may simply be untreatable. Thus, upon the occurrence of a cardiac event, it may be desirable for the control unit 120 or control unit 310 to identify the type of cardiac event and to determine what type of action or treatment would be most effective prior to initiating action in response to the occurrence of the cardiac event.

Emergency medical technicians may be trained to immediately transport a subject experiencing a cardiac event to a hospital; however, this may not always be the best course of action for the subject. For example, a subject may benefit from the administration of treatment that results in ROSC prior to being moved. Upon determination of the type of cardiac event being experienced by a subject, defibrillation may be applied to the subject or CPR and/or drug therapy may be administered, if appropriate, by the wearable medical device 100 or the medical support device 305 and/or the subject or a medical professional. If CPR and/or drug therapy is administered, parameters of the subject's ECG, for example, ASA, AMSA, and/or PSA may be monitored (as described in U.S. Patent Application Publication No. 2013/0331719, hereby incorporated by reference in its entirety) by the wearable medical device 100 or the control unit 120 or medical device 305 until the wearable medical device 100 or the medical device 305 determines that it is appropriate to administer defibrillation to the subject. If defibrillation is determined to be appropriate, defibrillation is applied by the medical device 305 and, if ROSC is observed in the subject, and/or if an improvement in $SpO_2$ or tidal $CO_2$ is observed, the medical device 305 may indicate that the subject may be transported to a hospital for further treatment or monitoring. In another example, if a subject's heart rate is decreasing (i.e., Bradying down), the subject may benefit from chest compressions prior to transport, which may be indicated by the medical device 305 to a medical professional at the scene.

An event estimation of risk score may be calculated by the control unit 120 or control unit 310 for a subject at risk of experiencing a cardiac event and/or for a subject that is experiencing a cardiac event. The event estimation of risk score may be calculated based on one or more measured physiological parameters of the subject, for example, one or more parameters associated with the subject's ECG or EEG, blood pressure, heart rate or change in heart rate, tidal $CO_2$, $SpO_2$, $SMO_2$, cerebral blood flow, brain oxygen level, tissue pH, reaction of the subject's heart to tilting of the subject, and/or ultrasound images of the subject's heart. If the event estimation of risk score satisfies a threshold value and/or indicates that the subject's condition is improving, the wearable medical device 100 or the medical support device 305 may advise transporting the subject to a hospital for further treatment and/or monitoring. If the event estimation of risk score does not satisfy a threshold value and/or indicates that the subject's condition is not improving or is worsening, the wearable medical device 100 or the medical support device 305 may advise treating or continuing treatment of the subject prior to transport. If a subject exhibits a poor or worsening event estimation of risk score, the wearable medical device 100 or the medical device 305 may advise administering an intervention, for example, to apply chest compressions, either manually or with an automated chest compression apparatus, until the subject's event estimation of risk improves to a level indicating that the subject is stable enough for transport. Calculation and analysis of event estimation of risk scores is discussed in more detail below.

In addition to, or as an alternative to, the application of chest compressions, the wearable medical device 100 or the medical support device 305 may advise that the subject be administered epinephrine, norepinephrine, beta blockers, nitrates, blood vessel dilators, or other drugs and/or be supplied with oxygen until the event estimation of risk score improves to a level that indicates to the wearable medical device 100 or the medical support device 305 that the subject is stable enough for transport. For example, to improve the event estimation of risk score, the wearable medical device 100 or the medical support device 305 may advise that the subject be provided with controlled blood vessel dilation. Nitrates, for example, nitroglycerine or nitrous oxide may be administered to the subject while chest compressions are performed. The chest compressions may be synchronized to the subject's cardiac cycle if the subject has a detectable pulse. Tissue or blood oxygen levels may be monitored by the wearable medical device 100 or the medical support device 305 to determine if an appropriate amount of nitrates or other blood vessel dilators have been administered to the subject. The administration of chest compressions and/or blood vessel dilators may be terminated if the wearable medical device 100 or the medical support device 305 determines that the subject exhibits ROSC or the event estimation of risk improves to a level that indicates that the subject is stable enough for transport.

Once the subject has achieved ROSC, the subject may be transported to the hospital to stabilize the subject medically as well as treat the subject for the underlying condition which caused the cardiac arrest, e.g. a heart attack. In some examples, 15% to 20% of subjects who achieve ROSC and are being transported to the hospital experience another cardiac arrest while being transported to the hospital. If the event estimation of risk score satisfies a threshold for a ROSC subject during transport, the ambulance or other transport driver or attendant who is riding with the subject in the vehicle may be notified by the wearable medical device 100 or the medical support device 305 with an alarm or other communication of the elevated risk so that the attendant may intervene by direct treatment of the subject or driving to get to the hospital more quickly.

Measurements of ECG as a predictor of a potential oncoming cardiac event or as a measure of the state of a subject's myocardium during a cardiac event and/or during the administration of treatment may be facilitated by the use of a motion sensor such as an accelerometer. An accelerometer built into the wearable medical device 100 or the medical support device 305, or a CPR assistance device, for example, a PocketCPR® real-time CPR feedback device or an AutoPulse® cardiac support pump, both available from ZOLL Medical Corporation of Chelmsford, Mass., may provide a signal regarding movement of the subject due to chest compressions or other movement of the subject which may be utilized to remove ECG signal artifacts due to the movement of the subject from a monitored ECG signal of the subject. The accelerometer may be a 3-axis accelerometer which may be used to correlate orientation, for example, a degree of tilt of a supine subject with changes in the ECG of the subject. For example, if a supine subject is tilted, e.g., by about 10 degrees or more, and a change occurs in the ECG signal of the subject, it may be an indication that the subject should not be immediately transported. Treatment, for example, chest compressions, drug therapy, or other intervention, may be performed until the subject can be tilted without a significant or a detectable change in the subject's ECG signal occurring, at which point it may be recommended to transport the subject to a hospital for further treatment and/or monitoring.

In some embodiments, an accelerometer may be utilized to monitor movement of a subject during transport, for example, due to travel of an ambulance over rough road, and the movement of the subject can be correlated with changes in the subject's ECG. If changes in the subject's ECG are correlated with movement of the subject, the wearable medical device 100 or the medical support device 305 may provide a recommendation to slow down the ambulance and/or to take a longer, but smoother route.

Figure 4:
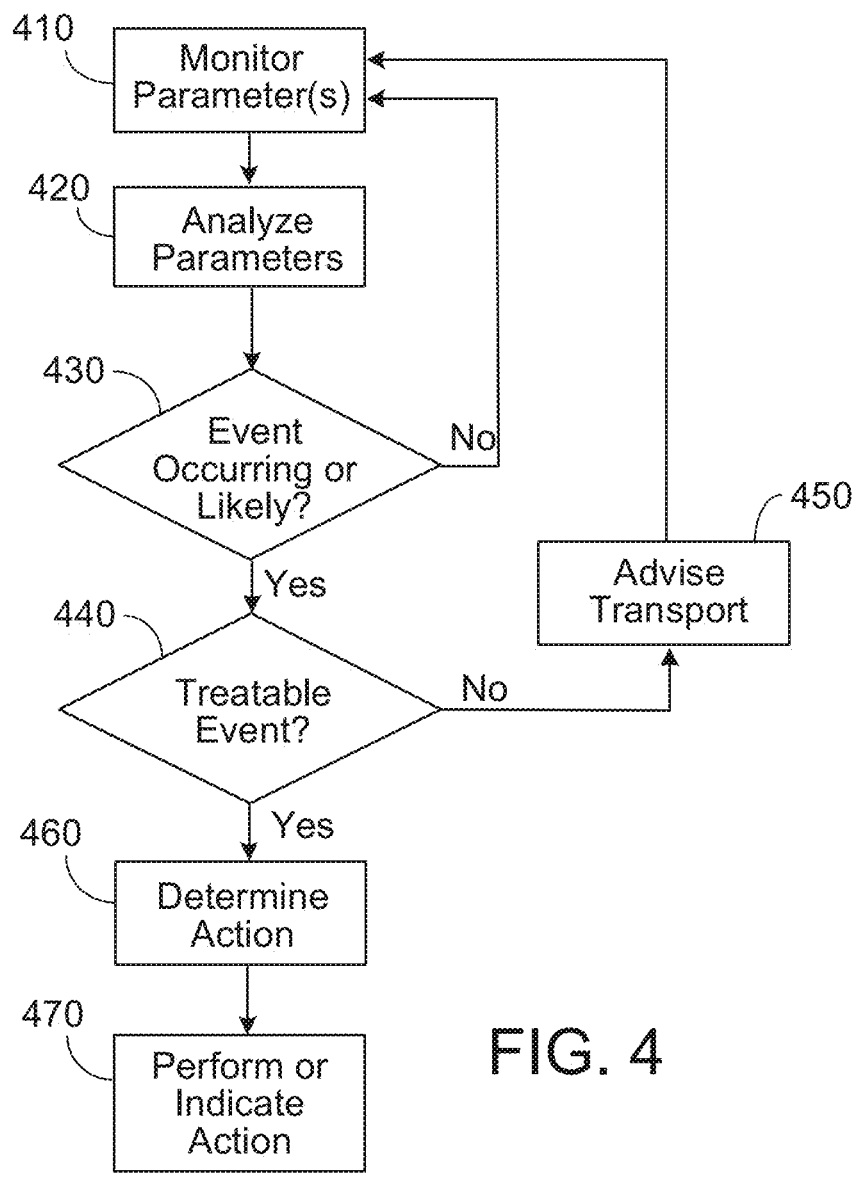
FIG. 4 is a flow chart of a medical premonitory event estimation and detection method.

FIG. 4 is a flow chart of a method that may be implemented by the wearable medical device 100 or the medical support device 305, for example, an ECG monitor/defibrillator, AED, or a wearable medical device, such as a Life-Vest® wearable cardioverter defibrillator. In stage 410, the wearable medical device 100 or the medical support device 305 monitors one or more parameters of a subject. The one or more parameters may be predictive of an oncoming cardiac event and/or may be used to calculate an event estimation of risk score for a medical event of the subject. The one or more parameters may include one or more parameters associated with the subject's ECG or electroencephalography ("EEG"), the heart rate or change in heart rate of the subject, blood pressure of the subject, tidal $CO_2$, $SpO_2$, $SMO_2$, cerebral blood flow, brain oxygen level, tissue pH, reaction of the subject's heart to tilting of the subject, and/or ultrasound images of the subject's heart. In stage 420, the parameters are analyzed by the control unit 120 or control unit 310 of the medical support device 305, for example, to calculate an event estimation of risk score or to determine if there is a high likelihood of an impending cardiac event and/or if a cardiac event is occurring. If the control unit 120 or control unit 310 determines in stage 430 that there is no cardiac event occurring and that there is not a high likelihood of an impending cardiac event, e.g., the event estimation of risk score is below a threshold, the device returns to stage 410 to monitor the parameters of the subject. In some embodiments, different parameters of the subject may be monitored at different times, for example, sequentially.

If, in stage 430, the control unit 120 or control unit 310 determines a cardiac event is occurring or that there is a high likelihood of an impending cardiac event, the control unit 120 or control unit 310 determines in stage 440 whether the cardiac event is treatable, for example, whether an intervention may be effective to treat the cardiac event or to reduce the chance or severity of the impending cardiac event. If it is determined by the control unit 120 or control unit 310 in stage 440 that the type of cardiac event the subject is experiencing cannot currently be treated by any intervention available to the medical device or by a first responder or if no intervention available to the medical device or to a first responder is currently capable of reducing the chance or severity of the impending cardiac event, the device may advise in stage 450 that the subject be transported to a facility, for example, a hospital for treatment and/or monitoring, and the device returns to stage 410 to monitor the parameters of the subject. The parameters of the subject may be recorded so that if the subject reaches a hospital or another source of treatment which may have capabilities beyond that of the medical device, the history of the subject may be reviewed to determine an appropriate treatment.

If, in stage 440, the control unit 120 or control unit 310 determines that the cardiac event that is occurring may be treated by an intervention available to the medical device or a first responder or that an intervention available to the medical device or first responder is capable of reducing the chance or severity of an impending cardiac event, the device, in stage 460, makes a determination of an available action (e.g., intervention) to provide to the subject. In some implementations, the device considers multiple potential interventions, but may provide the best type of available intervention to the subject.

In stage 470, the device performs or indicates the determined intervention, for example, by administering automated chest compressions, defibrillation, and/or automated drug delivery. If the selected intervention is one that the device cannot perform on its own, the device may provide an indication to a first responder, for example, through a display or a speaker of what intervention to administer to the subject or communicate the recommended treatment to another type of life support device that is capable of performing the recommended intervention.

Systems and method according to some embodiments that provide an event estimation of risk score are now discussed in more detail.

Systems and methods according to some embodiments provide software analytic tools that automatically analyze subject physiological parameter data, e.g., ECG data, to detect and predict pending conditions by calculating an event estimation of risk score for a medical event that is occurring or may occur within a time period. An event estimation of risk score may be calculated for more imminent medical premonitory events and longer-term medical premonitory events. Event estimation of risk scores may be calculated for medical events for a plurality of different time periods. In order to provide risk levels for various different time periods, multiple (e.g., different) event estimation of risk scores can be calculated for different time periods, (e.g., less than about 10 minutes, less than about 1 hour, less than about three hours, less than about 1 day, less than about 1 week, less than about 1 month, less than about 3 months, etc.), to provide a likelihood or probability of a medical event occurring within the respective time period.

The various event estimation of risk scores for each of the time periods may be compared to stored event estimation of risk thresholds associated with the time periods to determine a plan of action or a response that varies based on the event estimation of risk scores for each of the estimated time periods. Different time periods may be associated with different thresholds, and different medical events may be associated with different thresholds. For example, a threshold for applying defibrillation in response to a cardiac arrest for a more immediate time period may be different, e.g., and may be easier to satisfy, than a threshold for applying defibrillation in response to a cardiac arrest for a longer-term time period.

A plurality of different event estimation of risk scores for a plurality of different medical events may be calculated for a single time period. For example, an event estimation of risk score for a cardiac arrest and an event estimation of risk score for a non-sustained ventricular tachycardia may be calculated for the same time period.

In some implementations, an event estimation of risk score can be calculated for a single time period. For example, a single event estimation of risk score can be calculated for one of a time period of less than about 10 minutes, less than about 1 hour, less than about three hours, less than about 1 day, less than about 1 week, less than about 1 month, less than about 3 months, etc., to provide a likelihood or probability of a medical event occurring within the time period. The event estimation of risk score may be continuously updated over time (e.g., for the particular time period). For example, an event estimation of risk score may initially be determined for a time period of within one hour, and as time passes, the event estimation of risk score for the time period of within one hour is continuously updated.

An event estimation of risk score includes a criticality measure and a confidence measure. The criticality measure can provide an estimated measure of the risk, severity or significance of a potential medical premonitory event. For example, a medical event, such as a cardiac arrest, may be associated with a relatively high criticality measure while a medical event, such as an ectopic beat or a non-sustained ventricular tachycardia, may be associated with a relatively lower criticality measure. The criticality measure may be a quantitative score or a qualitative assessment. The confidence measure can provide a likelihood or probability that a particular medical event may occur for the associated time period. For example, the confidence measure may be a percent chance of event occurrence for the associated time period. The combination of the criticality measure and the confidence measure of an event estimation of risk score may be used to determine an appropriate response to the medical premonitory event, such as an appropriate action to take. For example, some treatments, such as defibrillation, may require a relatively higher confidence value prior to implementation. Other treatments, such as instructing the subject to sit down, may require a relatively lower confidence prior to implementation. Defibrillation may require a relatively higher criticality measure, e.g., a risk of cardiac arrest, than other treatments, such as instructing the subject to sit down, which may be satisfied by a relatively lower criticality measure, e.g., an increased heart rate.

Figure 5:
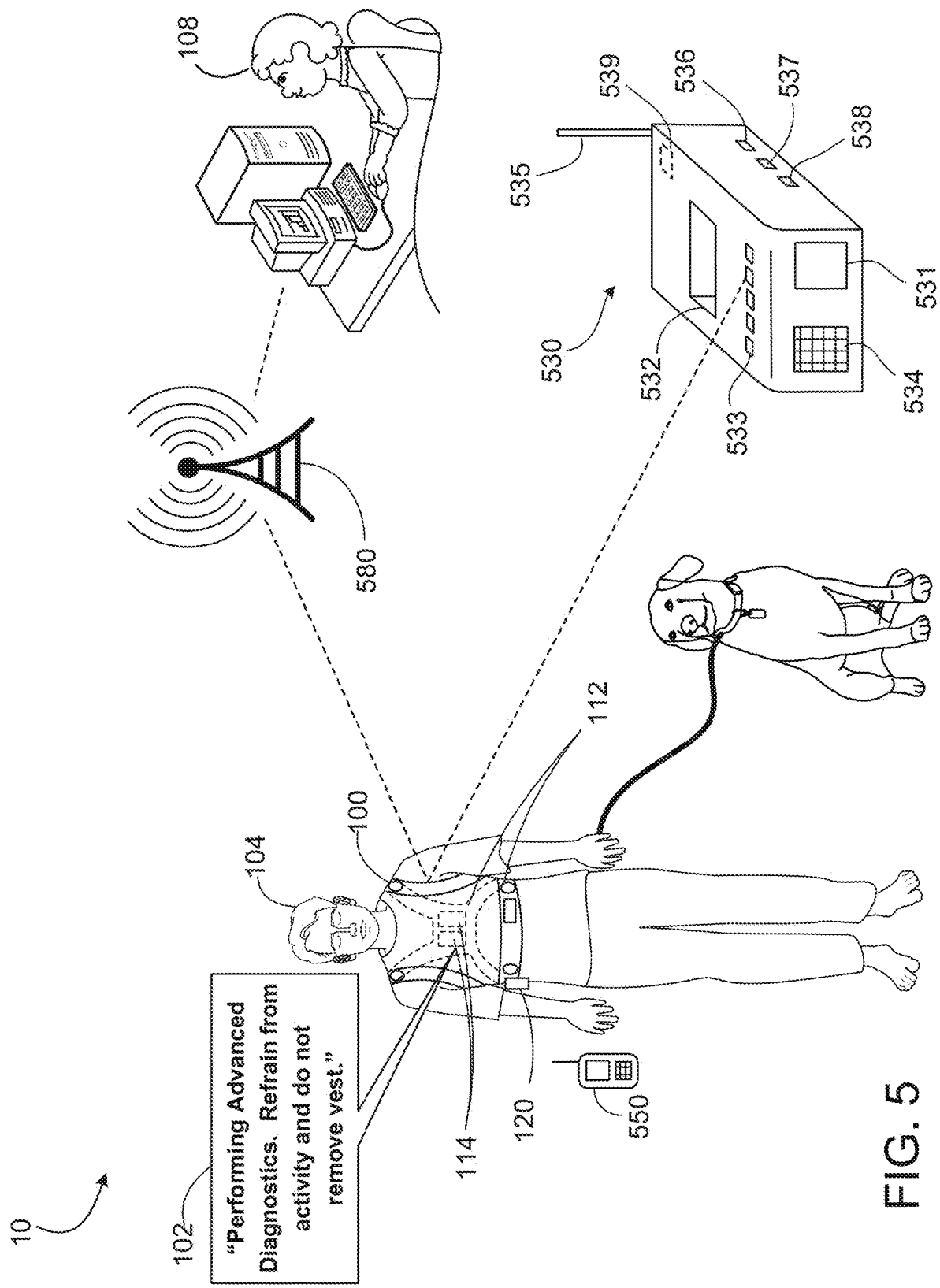
FIG. 5 shows a system for responding to a medical condition.

FIG. 5 shows a system for responding to a medical event. An early warning system 10 monitors the physical status of a subject 104 and uses the information to estimate the risk of medical events occurring. The early warning system 10 may include the wearable medical device 100 that is worn by subject 104. FIG. 5 is discussed with respect to the wearable medical device 100; however, disclosed embodiments are not limited thereto and the early warning system 10 may include another wearable device, the medical support device 305, an implantable medical device, a portable medical device, or other monitor of physiological parameters of a subject.

The wearable medical device 100 can measure data, such as ECG data of the subject 104, and can use the data to estimate the risk of medical events occurring in various time periods. The control unit 120 may calculate the event estimation of risk score by estimating the likelihood or probability of the subject 104 experiencing a future medical event if treatment efforts are not taken or not successful and/or determining that a cascade of events that will likely lead to a medical event without emergency response has already begun. An event estimation of risk score may sometimes be referred to, and used interchangeably with, "event prediction" or an "event prediction score", though the term event estimation of risk is typically more comprehensive in that, unlike the weather, which cannot be altered substantially, one of the goals of using an event estimation of risk is to alter the potential course of a subject's status. An event estimation of risk enables a device or medical personnel to do more than just "carry an umbrella" to deal with events as they occur. An event estimation of risk enables a device or medical personnel to prevent a medical event or reduce its effects. For example, the wearable medical device 100 may provide feedback and treatment options to the subject 104 to help prevent the occurrence of the medical event and/or mitigate the effects of the event. The wearable medical device 100 may additionally communicate information to an external entity, such as one or more medical professionals 108, to allow the medical professional to determine a plan of action, or course of treatment, for the subject 104.

The early warning system 10 according to non-limiting embodiments can predict medical events, e.g., adverse cardiac events, within seconds of the event to within years of the event with various degrees of sensitivity and specificity. Various actions or responses may be suggested to the subject 104 based on a time for a predicted medical event. For example, if an adverse cardiac event is predicted within a 10 minute timeframe from the present, the medical device 100 may alert the subject 104 to refrain from strenuous activity (e.g., walking a dog) and to not remove the medical device 100, e.g., so that the medical device is available to provide a defibrillation shock if needed. In contrast, if the medical device 100 determines that the subject 104 is exhibiting an elevated level of risk of an adverse cardiac event occurring in a one-week time frame from the present, the medical device 100 may alert the medical professional 108 or request that the subject 104 carefully follow the instructions of the medical professional 108. Further details of exemplary warnings, suggested feedback, and recommended activities are described herein for various time periods.

As noted above, the medical device 100 can predict the likelihood or probability of an adverse cardiac event occurring during multiple, different periods of time. The medical device 100 may calculate multiple different event estimation of risk scores associated with the potential of an adverse cardiac event for the subject 104, with each of the different event estimation of risk scores being associated with a different time period, e.g., each event estimation of risk score indicating the probability of an event occurring within a respective time period. The medical device 100 can calculate different event estimation of risk scores for short term and long term likelihoods of an adverse cardiac event, such as the likelihood that an adverse cardiac event will occur within one minute, ten minutes, one hour, three hours, one day, one week, one month, three months, etc. Providing multiple event estimation of risk scores associated with different time periods can allow for different treatments and alarms to be triggered or suggested based on the likelihood of an adverse event happening within a particular time period.

The control unit 120 of the wearable medical device 100 can monitor ECG signals provided by the plurality of ECG electrodes 112 and, where provided, some or all of the signals provided by other sensors. The control unit 120 can calculate event estimation of risk scores associated with the potential of an adverse cardiac event for a subject 104 during associated time periods based on the signals provided from the ECG electrodes 112 and, where provided, some or all of the signals provided by other sensors. The wearable medical device 100 can provide feedback to the subject 104 based on the calculated event estimation of risk scores. The feedback may be provided directly from the wearable medical device 100 and/or through a remote computing device 550, such as a mobile telephone, computer, or other computing device, in wired or wireless communication with the wearable medical device 100.

As shown in FIG. 5, the wearable medical device 100 may be associated with a base unit 530. For example, with the LifeVest™ wearable cardioverter defibrillator, a base unit 530 can be provided that is capable of performing a number of different functions. One of the functions that can be performed by the base unit 530 is to store and/or communicate information received from the wearable medical device 100 over a wired or wireless communication network 580. For example, information relating to the subject's medical condition over a period of time may be communicated by the base unit 530 to the medical professional 108, such as a doctor, so that the doctor may remotely monitor the subject's medical condition. The information received by the base unit 530 may be communicated over the communication network 580 shortly after it is received by the base unit 530, or alternatively, may be stored in a memory of the base unit 530 and communicated over the communication network 580 at a later time. The information that is communicated by the base unit 530 may be retained in a memory of the base unit.

In some embodiments, the base unit 530 or the remote computing device 550 may receive the measured data, such as the ECG data of the subject, from the wearable medical device 100 and use the data to estimate the risk of medical events occurring in various time periods. For example, because some algorithms for medical premonitory event estimation and detection may be computationally intensive, some or all of the processing for determining event estimation of risk scores and/or actions in response thereto, such as operations performed by the machine learning classification system described below, may be performed on server hardware that is separate from the wearable medical device 100 itself that is either being worn or is nearby the subject 104.

The base unit 530 may include a visual display 531 that communicates visual messages to the subject 104 or a bystander, an audio output device 534, such as a loudspeaker, that communicates audible messages to the subject or a bystander, and a plurality of buttons 533 by which the subject or a bystander may communicate with the base unit 530. The visual display 531 may include a touch screen display, such that the subject 104 or a bystander may also communicate with the base unit 530 via the visual display 531. The visual display 531 may display information about the predicted risk for the subject 104. The information may be displayed graphically to allow the subject 104 and/or a caregiver to assess both the current risk and future risk of an adverse cardiac event. For example, briefly referring to FIG. 6A, a bar graph can provide a visual representation of example cardiac event estimation of risk scores for multiple time periods. The visual representations of the event estimation of risk scores for the various time periods may include information related to a reliability of the event estimate of risk score, e.g., a confidence value, associated with the corresponding event estimation of risk score. For example, a visual representation 602*a*-*h* of the confidence value may be superimposed on each bar of the bar graph. The visual representations 602*a*-*h* of the confidence values can indicate a likelihood that an event may occur for the associated time period, such that the visual representations that span a relatively greater distance (e.g., the visual representations 602*g* and 602*h*) indicate a relatively lower confidence in the event estimation of risk score than the visual representations that span a relatively lesser distance (e.g., the visual representations 602*a* and 602*b*). In some implementations, the ranges of the visual representations 602*a*-*h* of the confidence values may indicate possible error ranges of the corresponding event estimation of risk score. In some examples, confidence values for event estimation of risk scores that correspond to relatively longer time periods (e.g., within one month, within three months) are lower than confidence values for event estimation of risk scores that correspond to relatively shorter time periods (e.g., within ten minutes, within one hour). This may be due to the difficulty involved in making predictions relatively far into the future, for example.

Figure 6A:
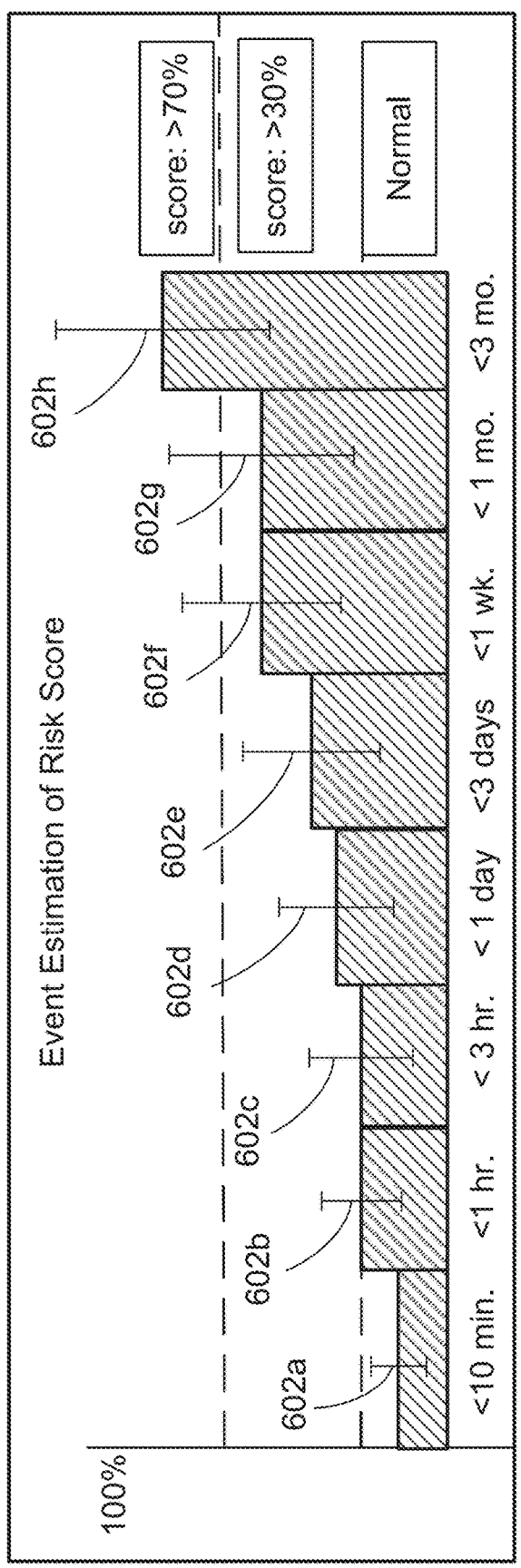
FIGS. 6A and 6B are graphs of example estimation of risk scores.
Figure 6B:
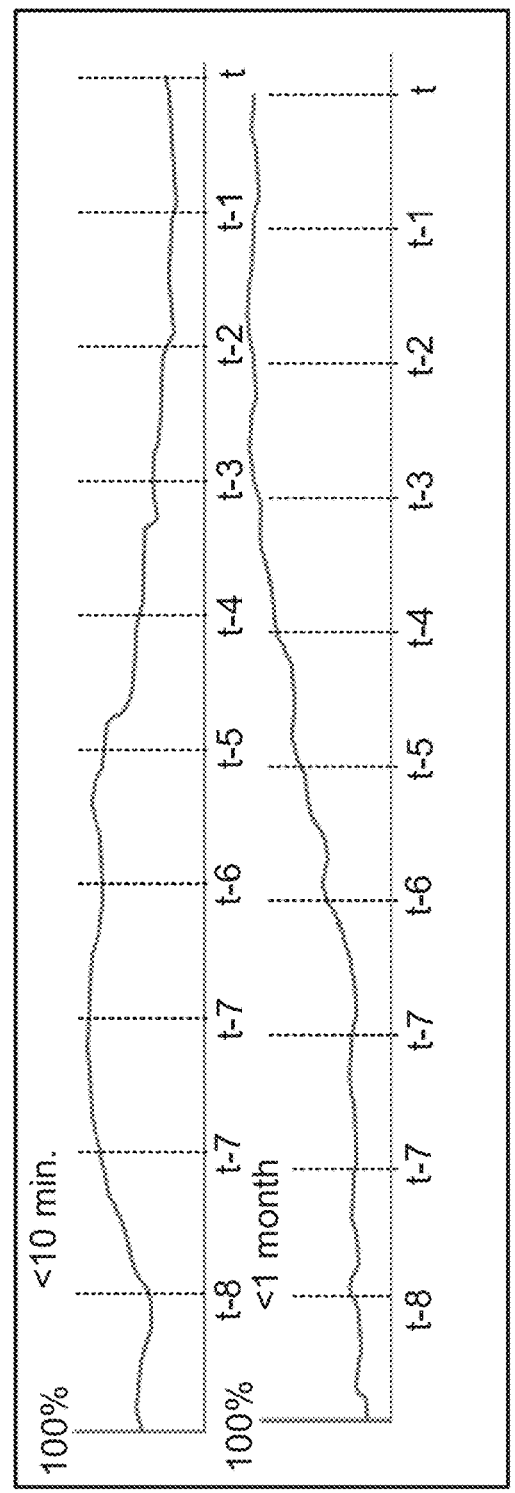

In some examples, historical information about the progression or change in event estimation of risk scores may be provided, examples of which are shown in FIG. 6B. FIG. 6B includes multiple trend lines representing previously calculated event estimation of risk scores over a period of time. The event estimation of risk scores and other information related thereto may be transferred from the medical device 100 and/or the base unit 530 to the remote computing device 550, which may comprise a smartphone, a personal digital assistant (PDA), a laptop, a tablet personal computer (PC), a desktop PC, a set-top box, an interactive television and/or combinations thereof or any other type of medical device for display and/or processing thereon.

The base unit 530 may include at least one charging bay 532 to receive a rechargeable auxiliary battery (e.g., a battery of the control unit 120). The base unit 530 may include one or more different communication interfaces, for example, a device communication interface 538 configured to receive information from the control unit 120 of the wearable medical device 100, a telephone network interface 536 to communicate, via a telephone network, the information received from the wearable medical device 100, and a network interface 537 to communicate, via a wired or wireless network connection, the information received from the wearable medical device 100. The base unit 530 may include an antenna 535 and (optionally) a wireless transceiver 539 configured to wirelessly communicate the information received from the wearable medical device 100 via a cellular (e.g., 2G, 3G, and 4G) or another wireless network. The base unit 530 may send the calculated event estimation of risk scores to the medical professional 108 (e.g., to allow the medical professional 108 to determine a plan of action or course of treatment for the subject 104).

Figure 7:
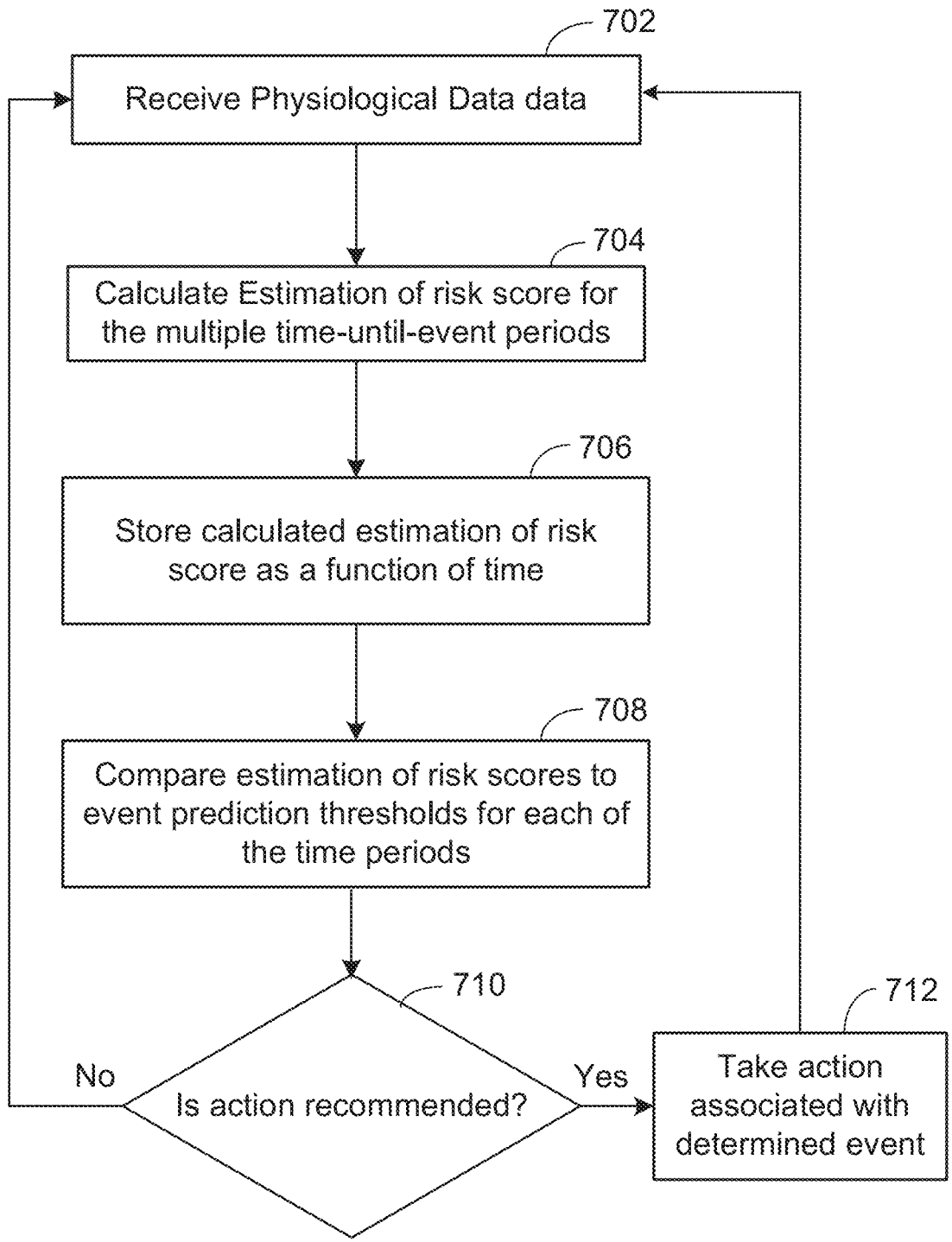
FIG. 7 is a flow chart of another medical premonitory event estimation method.

Referring now to FIG. 7, a flow chart illustrating an example method for determining a cardiac risk indicator, such as an event estimation of risk score, is shown. The event estimation of risk score may be determined by the wearable medical device 100 (FIGS. 1 and 5) described herein; however, example embodiments are not limited thereto and the event estimation of risk score may be determined by another device, such as the base unit 530, the remote computing device 550, and/or by a computing device of the medical professional 108 in communication with the medical device 100 and/or the base unit 530.

At stage 702, a subject is monitored by the wearable medical device 100, by receiving, measuring, and/or recording one or more types of physiological data, for example, a signal including ECG data. The ECG data may be received from any appropriate source of subject ECG data. For example, ECG data may be received in real-time from the ECG electrodes 112 attached to the subject. The ECG data may be of any appropriate type. The ECG data may be recorded from a plurality of lead sites on the surface of the subject's body. The ECG data may be received together with additional subject data including subject statistics and/or other physiological data recordings. The subject statistics may be used in conjunction with subject-specific ECG data for data processing and display.

At stage 704, event estimation of risk scores, e.g., estimated quantitative risk values, are calculated (e.g., by the control unit 120) for multiple time periods (e.g., multiple time-until-event periods).

At stage 706, the calculated event estimation of risk scores as a function of time are stored (e.g., by the control unit 120). Event estimation of risk scores (e.g., which can include both criticality and confidence measures) are stored for each of the time periods and each of the medical events for which the score is calculated. For example, separate scores may be calculated and stored for time periods of before ten minutes, before one hour, before two hours, before four hours, before eight hours, before twelve hours, before twenty-four hours, before forty-eight hours, and before seventy-two hours, and scores for multiple different medical events may be calculated and stored for each of the time periods.

At stage 708, the event estimation of risk scores for each of the calculated time periods are compared to event thresholds, such as stored event estimation of risk threshold values (e.g., by the control unit 120). Based on the comparison, a treatment plan or course of action is determined.

If event estimation of risk scores for multiple different time periods are calculated, for example, if the control unit 120 calculates an event estimation of risk score for a first period and an event estimation of risk score for a second period, the control unit 120 may prioritize one of the event estimation of risk scores over the remainder. For example, the event estimation of risk scores may be prioritized based on the criticality of each score. The control unit 120 may compare event estimation of risk scores having relatively higher criticality measures to stored event estimation of risk threshold values for corresponding time periods, and determine, based on the comparison, a treatment plan or course of action before doing the same for the event estimation of risk scores having relatively lower criticality measures. In some embodiments, the prioritization of the event estimation of risk scores may be based on a weighting scheme that may be calculated based on one or more of the criticality measure, the confidence measure, and the risk associated with each event estimation of risk score. In some embodiments, the control unit 120 may prioritize event estimation of risk scores for relatively more immediate time periods above event estimation of risk scores for relatively distant time periods. Similarly, if the control unit 120 calculates event estimation of risk scores for multiple different medical premonitory events in the same time period, the multiple event estimation of risk scores for the same time period may be prioritized based on the criticality of each score or the weighting scheme that is calculated based on one or more of the criticality measure, the confidence measure, and the risk associated with each event estimation of risk score.

Figure 12:
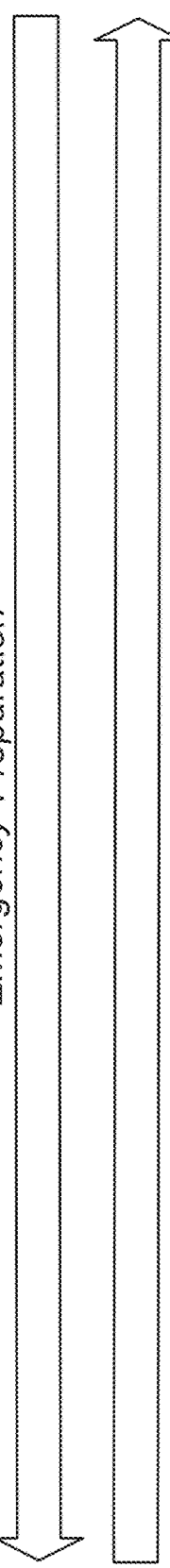
FIG. 12 is a chart of example actions for time periods.

At stage 710, based on the results of the comparison of the event estimation of risk scores to the event estimation of risk thresholds, a determination is made (e.g., by the control unit 120) as to whether an action is recommended. For example, if an event estimation of risk score for a particular time period satisfies a stored threshold value for the particular period, an associated action can be performed by the wearable medical device 100 and/or recommended to the subject by the wearable medical device 100. Exemplary actions may range from requesting that the subject keep on the wearable medical device 100, to suggesting that the subject lessen physical activity, to administration of a medication, to defibrillation. Various exemplary actions are shown in FIG. 12 and described in more detail herein for different time periods.

If an action is recommended at stage 710, at stage 712, an action associated with the determined event is taken (e.g., the action is performed by the wearable medical device 100). The method then returns to stage 702 to receive the physiological data. If action is not recommended at stage 710, the method returns to stage 702 to receive the physiological data.

In some embodiments, the wearable medical device 100 may display the calculated event estimation of risk scores on the interface pod 140, the remote computing device 550, the visual display 531 of the base unit 530, and/or the computing device of the medical professional 108. The event estimation of risk scores may be displayed, for example, as a bar graph, a list, or as a curve on the display, for example, as shown by FIGS. 6A and 6B. A time window for which prior event estimation of risk scores are displayed may be selected by the subject or another user, for example, to display a shorter or longer time range for the scores. A time-dependent event estimation of risk calculation and evolution may thus be generated and displayed to the subject and/or the medical professional.

Event estimation of risk scores may be calculated using various processes, algorithms, scoring models, mathematical models, statistical analysis, etc. A method for calculating the event estimation of risk scores may depend on a type of the medical event to be predicted. For example, the control unit 120 may be configured to use a first process or algorithm to calculate an event estimation of risk score for a cardiac arrest and a second, different process or algorithm to calculate an event estimation of risk score for a ventricular fibrillation. A risk of impending acute degeneration of a subject's medical condition into cardiac arrest or other severe cardiopulmonary conditions may thus be calculated by a variety of methods. Different methods and algorithms may be used to calculate the event estimation of risk scores for different time periods. For example, the control unit 120 may be configured to use a first process or algorithm to calculate an event estimation of risk score for a cardiac arrest in a first time period and a second, different process or algorithm to calculate an event estimation of risk score for a cardiac arrest in a second, different time period.

In some implementations, a machine learning classifier as described in further detail below can be trained on a large population, for example, a population that can range from several thousand to tens of thousands of patient records comprising electrophysiology, demographic and medical history information. The machine learning tool can include but is not limited to classification and regression tree decision models, such as random forest and gradient boosting, (e.g., implemented using R or any other statistical/mathematical programming language). Any other classification based machine learning tool can be used, including neural networks (as described in more detail below) and support vector machines. Because the machine learning tool may be computationally intensive, some or all of the processing for the machine learning tool may be performed on a server that is separate from the medical device.

An overview of how a random forest tool may be applied to a given dataset can illustrate how a classification tool may work in interpreting given parameters or metrics. A random forest is a collection of decision trees. A decision tree is a flow chart-like structure in which each node represents a test on a metric and each branch represents the outcome of the test. The tree culminates in a classification label, e.g., a decision taken at the end after computing each of the metrics. Each tree in a random forest tool gets a "vote" in classifying a given set of metrics. There are two components of randomness involved in the building of a random forest. First, at the creation of each tree, a random subsample of the total data set is selected to grow the tree. Second, at each node of the tree, a "splitter variable" is selected and the underlying patients are separated into two classes. For example, patients in one class (e.g., Response or occurrence of sudden cardiac arrest) can be separated from those in another class (e.g., Non-Response). The tree is grown with additional splitter variables until all terminal nodes (leaves) of the tree are purely one class or the other. The tree is "tested" against patient records that have been previously set aside. Each patient testing record traverses the tree, going down one branch or another depending on the metrics included in the record for each splitter variable. The patient testing record is assigned a predicted outcome based on where the record lands in the tree (a vote). The entire process may be repeated with new random divisions of the underlying dataset to produce additional trees and ultimately a "forest". In each case, a different subset of patients can be used to build the tree and test its performance.

In developing the results described in the below example implementation, a predetermined number of model variations are trained. For example, each model variation is labeled sequentially, (e.g., for 100 runs, labeled from 1-100). In each run of the model, the software randomly sampled a predetermined portion (e.g. an 80% portion) of the population as the training set and set aside the remainder (e.g., 20%) as the testing set. The ratio of no shocked "Non-Response" to shocked "Response" patients observed in the underlying data was predetermined to be 2.5:1, however, any other ratio of Response to Non-Response or proportion of training and testing sets can be selected.

In the example implementation described below, example inputs into the model may include the following:

a) ECG metrics; and b) non-ECG metrics, as described in greater detail below.

The possible model outcomes for training in the example implementation are as follows:

i) Appropriate shock (1=yes; 0=no);

ii) Asystole (1=yes; 0=no); and iii) Ejection Fraction (EF) improved (e.g., above 35%) (1=yes; 0=no).

In some embodiments, risk of other endpoints (end of device use points), such as inappropriate shock, compliance with device use, hospitalization, medication changes, and death (non-sudden or total mortality) can be estimated. In some embodiments, prior to running the models, metrics that are highly correlated to each other can be removed and/or replaced with a representative set of metrics.

As noted above, the machine learning tool can train the classifier on a first portion of the underlying dataset, and test the classifier on a second portion of the dataset or on another separate dataset. When evaluating the performance of each classifier, the performance of the underlying decisions within the decision trees in the random forest can be evaluated based on specificity and sensitivity parameters. For example, the sensitivity parameter can be based on a measure of the classifier's ability to correctly predict whether a patient is at risk of requiring treatment. For example, the sensitivity parameter may be based on a proportion of patients who are appropriately treated that the model correctly predicts are at risk of being treated. The specificity parameter can be based on the proportion of patients who are not treated through the device end of use, and who are predicted by the relevant classifier as not at risk of requiring treatment. It may be advantageous to optimally balance individual performance variables such as sensitivity and specificity at a high level. For example, by setting the specificity at a relatively high value, e.g., 95%, the underlying thresholds within the classifier model may be adjusted to minimize false positives. After the specificity is defined, the measure of sensitivity can be treated as a type of performance measure, e.g., generally in the range of 15-35% for a given model, however, smaller or larger values of sensitivity are also possible.

A validation protocol, for example, as described below, can be employed to validate the predictive performance of trained models. In an implementation, the validation phase can be used to ascertain appropriate threshold scores for classifying future patients (where an outcome is currently unknown and a prediction of the outcome is desired) and to determine the predictive performance of each classifier model generated by the machine learning tool. For validating the various classifiers and associated threshold scores, a second group of individuals, e.g., a validation population (or cohort), can be used. For example, the validation population used can be a new validation population. The outcome for the patients in the validation cohort is eventually learned as these patients progress to the device end of use. In an embodiment, the patients in the validation population can be different from the group of training and test patients described above for training the classifier. For example, a validation population of patients and their associated metrics (validation metrics) can be independent from a training population of patients and associated metrics (training metrics). In some implementations, there may be an overlap between the validation metrics and the training metrics.

The validation data can be obtained as shown in Table 1 below. In some example, at the start of wear, a baseline ECG recording can be obtained from an underlying patient. The baseline recording is typically about 45-60 seconds long, however, longer or shorter ECG recordings are possible. Each subsequent week, a new 45-60 second ECG recording can be obtained from the patient, however, the frequency of ECG recordings can be increased or decreased, for example, the frequency of ECG recordings can be increased in order to obtain more finely timed event estimation of risk scores on individual patients.

TABLE 1

Test Performance Summary for Shocked Patients

| | Baseline recording | Subsequent recordings |
|---|---|---|
| When | Start of device use | Weekly recording |
| What | Snapshot | Snapshot |
| Example frequency | 1 (initial recording) | 8 recordings [range 4 to 12] |
| Example specificity, fixed | 95 | 95 |
| Example sensitivity observed | 18 | 22 |

For each patient in the validation population, an event estimation of risk score can be generated from each machine learning classifier model. For example, the "Predict" command in a statistical computing language such as R (available from the R Foundation) can be called for each classifier. In R, the "Predict" command takes a patient's metrics as input and a corresponding classifier model including the machine learning algorithm against which the patient's metrics are to be run. For random forest classifier models, the output can be a probability score with a range of values from 0 to 1. Accordingly, because the underlying model is based on appropriate shock "Response" and no shock "Non-Response", the example output score is in a range of 0 (risk of shock equivalent to the majority of patients) to 1 (risk of shock is defined as immediate since it is elevated relative to the majority of patients). In this manner, the patient's metrics can be used against each of the pre-built models in order to identify the best performing machine learning classifier. As noted above, when using the validation population, the patient's outcome is ultimately known. As such, during post-hoc analysis how well each classifier model performed can be assessed. This process may be repeated for each patient in the validation population.

In some implementations, the validation population can be updated by at least one of 1) adjusting one or more of the metrics in the validation metrics, and 2) expanding the validation metrics based on appending additional one or more subjects to population of subjects that make up the validation population. The thresholds for classifying future patients can be refined based on the updated validation metrics. For example, metrics of a patient that is currently being treated or monitored or has otherwise not progressed through the device end of use can be used to adjust the one or more metrics in the validation metrics or the patient's metrics can be added to the validation population as metrics from a new subject. The validation metrics can be adjusted as new metrics for the patient are determined during the monitoring or treatment of the patient. In some examples, as a monitored patient progresses through the device end of use, the patient's metrics can be added to the validation population and/or used to adjust the metrics in the validation metrics after the patient has progressed through the device end of use.

In some implementations, the training population can be updated by at least one of 1) adjusting one or more of the metrics in the training metrics, and 2) expanding the training metrics based on appending additional one or more subjects to the first plurality of subjects. The machine learning classifier models can be retrained based on the updated training metrics. For example, as additional patient metrics are determined from current patients and/or metrics from new patients are determined, the machine learning classifier can be retrained, e.g., on the increased number of metrics or on new, different metrics, to provide updated classifier models. The training population can be updated as new metrics for current patients and/or metrics for new patients are determined or after patients have progressed through a device end of use.

Figure 8A:
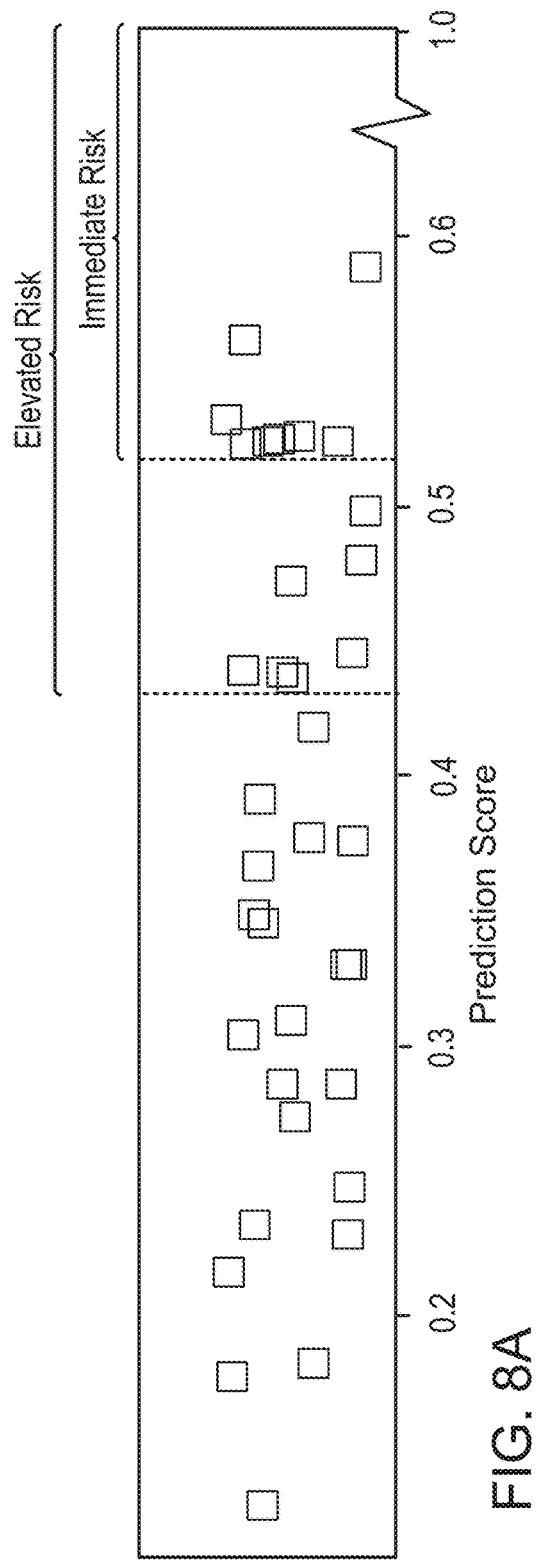
FIG. 8A illustrates a spread of event estimation of risk scores for patients.

Referring to FIG. 8A with respect to an example model called "model 80", the scores for patients that do get appropriately shocked are shown by the x-axis of the graph. The y-axis of the graph need not represent any value, and the plotted values are separated along the y-axis for ease of viewing. As shown, for this example model, a threshold may be set such that an event estimation of risk score above 0.425 can be considered as classifying the patient as being at elevated risk of being shocked when compared with other patients (e.g., patients who have event estimation of risk scores below 0.425). For example, a patient who has an event estimation of risk score that classifies the patient as being at elevated risk may have a relatively higher likelihood of experiencing a medical event as compared to patients who are not classified as being at elevated risk.

For this example model, another threshold may be set such that an event estimation of risk score above 0.52 can be considered as classifying the patient as being at immediate risk of being shocked when compared with other patients (e.g., patients who have event estimation of risk scores below 0.52). For example, a patient who has an event estimation of risk score that classifies the patient as being at immediate risk may have a relatively higher likelihood of experiencing a medical event as compared to patients who are not classified as being at immediate risk, and thus there may be an immediate concern for the patient that requires an action to be taken. In response, one or more actions may be taken and/or the patient may be instructed to perform one or more actions that are intended to reduce the patient's risk of experiencing a medical event. For example, one or more operational parameters of the medical device and/or one or more threshold values for determining whether a medical event has occurred may be adjusted to accommodate the immediate risk patient, as explained in more detail below. In this way, patients who are classified as being at immediate risk may have their risk reduced, whereas patients who are not classified as being at immediate risk may not be required to take steps to reduce their risk, e.g., steps which may be inconvenient for the patient and thus be counterproductive. While one of more actions may be taken for a patient who is classified as being at immediate risk, such actions need not necessarily be taken immediately.

It is appreciated that while the above example implementation describes two thresholds, there may be more (e.g., three or more) thresholds or only a single threshold. Each threshold may correspond to patient populations on which differing actions may be taken. For example, in some implementations, instead of having both elevated and immediate risk thresholds, there may be only a single threshold, e.g., an immediate risk threshold. Patients that have a risk score that places them at or above such immediate risk threshold may have one or more immediate actions taken relative to those patients that are not at or above the threshold.

For example, patients that are classified as having elevated risk but where no immediate action may be taken (e.g., patients with risk scores at or above 0.425 but below 0.52 in the example above) may have their physiological parameters monitored on a more regular basis than patients who are not classified as being at elevated risk. For example, a physician and/or a technician may cause the medical device (e.g., the wearable defibrillator) to stream the patient's ECG data in substantially real time for analysis. Alternatively or additionally, the physician and/or technician may request additional monitoring of the patient at least for the period during which the patient remains as being an elevated risk. Further, with respect to patients for whom an immediate action is deemed necessary (e.g., patients with risk scores at or above 0.52), a physician may deem it necessary to instruct the patient to perform more frequent device checks (e.g., ensure battery charge is at optimal levels), minimize certain activities, minimize times when the medical device is not actively monitoring the patient, etc.

In some examples, the scores from each of the models can be combined in a predetermined manner to generate a single event estimation of risk score for a patient. In some examples, clustering techniques can be implemented during validation to select the most predictive set of classifier models. For example, the most predictive, validated set of classifiers can be identified based on sensitivity values occurring in a predetermined range, (e.g., exceeding 0.25 or any other predefined threshold). In some examples, a single model, such as example model 80, as shown above, may be selected and used for determining an event estimation of risk score for a given patient. Any other implementation can be used in selecting the appropriate classifier model(s) and/or combining the scores from the various models.

More than one summary measure, e.g., more than one event estimation of risk or more than one combination of multiple event estimation or risk scores from multiple models, may be considered so that different aspects of time series risk scores can be investigated. The different summary measures can be combined into a single result to characterize the patient's overall state, e.g., whether the patient's risk profile is getting better or worse. For example, the time series of risk scores can be analyzed using techniques described in J N S Matthews, Douglas G Altman, M J Campbell, Patrick Royston, "Analysis of serial measurements in medical research," which contents are incorporated herein in its entirety.

In some examples, a single event estimation of risk score is determined from the above process to characterize a patient's risk. From the validation process described above, the appropriate threshold is selected to achieve the predefined performance level of specificity. When incorporating time series measurement it may be found that over a period of time, the patient's score may increase or decrease. As a result, observing changes in the patient's score over a period of time until eventual device end of use enables various information to be determined as described below.

The time series data for each patient can be evaluated using a number of techniques to assess whether the patient's risk is increasing or decreasing over time. For example, the time series values may be plotted and an area under the curve can be calculated as a measure of weighted average. In some examples, a mean of the observations may be taken.

If the intervals between the observations are kept the same, (e.g., hourly or weekly), the mean can be closely related to the weighted average. In implementations, either the mean or the weighted average can be compared against its respective threshold. In some examples, an amount by which the mean/average transgresses the corresponding threshold may be considered in determining how the patient's condition is changing.

In some examples, a number of times the risk scores transgress the threshold may be noted and a trend of such transgressions can be extracted from such data. For a gradient boosting model, the resulting prediction score trend ranges in values given by the logit transformation of the underlying probability score, (e.g., values typically fall within the range of −4.5 to 4.5, where a logit value of 0 corresponds to a probability value of 0.5).

For example, the following metrics were found to be highly predictive of eventual outcomes (e.g., appropriate shock versus no shock). Hypothetical values are shown below for the metrics to indicate that the patient might be classified as elevated or immediate risk.

Gender: Male (1)—more likely than female (0)

Age 56—generally higher risk range

Acute myocardial infraction (MI) diagnosis. (Alternatively, added patient metrics and/or time series measurements may improve the prediction of congestive heart failure patients (MI with heart failure, etc.).

Ejection Fraction (EF) below e.g., 35% (e.g., an actual EF value of 25%)

Other morbidities, such as diabetic, kidney failure, tobacco use, etc.

For a baseline ECG, e.g., 60 seconds, that is fed into the machine-learning classifier model, the following morphological parameters may be predictive of the patient's eventual outcome: QRS Morphology and variability features, QRS width, QRS height, Single Lead QRS Morphology, and Dual Lead QRS Morphology. For example, for a classifier that has been previously trained as described above, at the end of the analysis, the model (e.g., a model similar to model 80 above) may produce a score of 0.6 for the above example hypothetical patient. Over time, this patient's score may change, for example, as: 0.65, 0.5, 0.55, 0.45, 0.6. The time series analysis described above can be used to recommend the nature of the action to be taken as described herein, for example, with respect to FIGS. 11 and 12.

In various implementations, the parameters or metrics used for calculation of event estimation of risk scores may be grouped into three main categories, e.g., A) Heart Rate, Heart Rate Variability, and Heart Rate Irregularities; B) QRS morphology and Variability; and C) ST segment and T-Wave Morphology and Variability. The main categories can be organized by tables or sub-categories of metrics therein. An ECG may be obtained over a time period of between 45 and 60 seconds; however, example embodiments are not limited thereto and a length of the ECG can be longer or shorter. Example metrics that can be determined based on the ECG are listed below, however, example embodiments are not limited to these metrics and various other metrics can be used to calculate and classify event estimation of risk scores.

In an example based on a wearable monitoring and/or treatment device, each of the metrics are evaluated independently on side-to-side (SS) and front-to-back (FB) channels. For example, the SS and FB channels represent locations of the corresponding ECG sensors about the patient's body during use of the wearable monitoring and/or treatment device. In various examples, an equal number metrics for SS and FB channels can be used. For example, in some implementations, heart rate related measurements may be similar between SS and FB. Conversely, in some implementations, morphology measurements may be different between SS and FB. In an example, measurements from the SS channel are employed for prediction and both measurements (SS and FB) can be employed in other scenarios, such as those discussed below.

Heart rate, heart rate variability, and heart rate irregularities metrics include metrics that are derived from estimation of RR (R-wave to R-wave) intervals as detected by a QRS detector. In some implementations, evaluation of these metrics includes discriminating between normal beats (N) and ectopic beats (e.g. PVC). For example, a PVC detector can be used to identify PVCs. Intervals between two normal beats are called NN intervals. Metric tables or sub-categories of metrics that are included to this category can include:

1) Heart Rate metrics;
2) Heart Rate Variability (time domain) metrics;
3) Non Sustained VT episodes count metrics; and
4) PVC count metrics.

QRS morphology and variability metrics include metrics that describe shape and variation over time of QRS complexes as detected by a QRS detector. In some implementations, evaluation of these metrics includes discriminating between normal beats (N) and ectopic beats (e.g. PVC). For example, a PVC detector can be used to identify PVCs. Metric tables or subcategories that are included in this category can include:

1) QRS Width metrics;
2) QRS Height metrics;
3) Single Lead QRS Morphology metrics (e.g., similarity scores with respect to a normal template); and
4) Dual Lead QRS Morphology metrics (e.g., descriptors that describe the vector cardiogram).

ST segment and T-Wave morphology and variability metrics include metrics that describe shape and variation over time of ST segment and T-Wave as delineated by a T-Wave detector. In some implementations, evaluation of these metrics include discriminating between normal beats and ectopic beats. For example, a PVC detector can be used to identify PVCs. As such, the metrics can include an indication of a presence or absence of ectopic beats in an underlying one or more metrics. For example, T-wave metrics are evaluated on normal beats and ectopic beats are excluded from T-wave analysis because T-wave cannot be clearly identified or defined on ectopic beats. Metric tables or sub-categories that are included in this category can include:

1) QT variability metrics;
2) ST depression/elevation, slope metrics;
3) T-wave alternant metrics;
4) T-wave variability metrics; and
5) Dual lead T-wave Morphology (e.g. cosine RT) metrics.

In an example, single lead QRS morphology metrics can include SS and FB channel similarity scores. For example, these similar scores can include metrics that indicate score averages over time on the SS and FB channels. In implementations, similarity scores are obtained by comparing QRS complexes to a normal template, e.g., (one for SS and one for FB). For example, such similarity score metrics may or may not include ectopic beats.

Figure 8B:
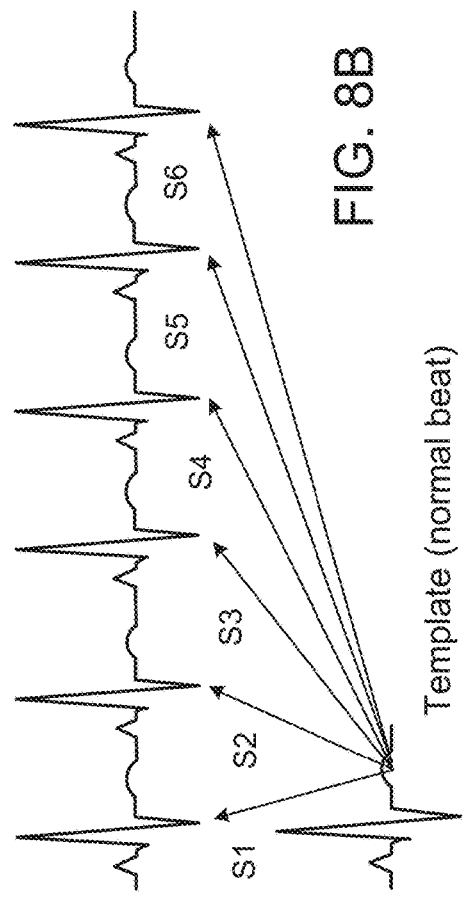
FIG. 8B illustrates an example ECG signal for determining a single lead QRS morphology metric.

For example, as shown in FIG. 8B, the main normal template is compared (arrows in the plot) with QRS complexes of the ECG signal. The obtained similarity scores are averaged to obtain a unique morphology score. In this example, ectopic beats may not be included in the calculation. The score can describe a variability in shape as compared to the normal beat. For example, if one of the compared QRS morphology departs from the normal template, the similarity score may assume a smaller value. A lower average score indicates a higher variability of QRS morphology in the normal ECG rhythm.

In another example, heart rate variability (HRV) metrics can include SDNN, which indicates the standard deviation over time of NN intervals. In some implementations, the SDNN calculation may not include ectopic beats. FIG. 8C is a graph of an example ECG signal for determining a heart rate variability metric. As shown in FIG. 8C, five Normal to Normal intervals 801a-e are employed to calculate SDNN. The intervals before and after the PVC may be excluded from the SDNN evaluation. SDNN is thus calculated as the standard deviation of (NN1, NN2, NN3, NN4, NN5).

In an example, QRS width metrics can be based on any one of a standard deviation, a mean, or other average over time for corresponding estimated widths of QRS complexes. In some implementations, the QRS width metrics may not include ectopic beats such as PVCs. In some implementations, the QRS width metrics may include an indication of the presence or absence of ectopic beats. FIG. 8D is a graph showing an example ECG signal that illustrates an example of QRS width.

In an example, QRS height metrics can be based on any one of a standard deviation, a mean, or other average over time of the estimated height of QRS complexes. In some implementations, the QRS height metrics may not include ectopic beats such as PVCs. In some implementations, the QRS width metrics may include an indication of the presence or absence of ectopic beats. FIG. 8E is a graph showing an example ECG signal that illustrates an example of QRS height.

An external medical device can monitor and collect a subject's physiological information, e.g., cardiac electrophysiologic information, and, along with known risk factors associated with sudden cardiac death, such as but not limited to low left ventricular ejection fraction, classify the patient by risk category based on the above-described machine learning classifier models. The device can include an external defibrillator to apply treatment, such as defibrillation to the subject when necessary, for example, after detection of sustained ventricular tachyarrhythmia or fibrillation.

Technical principles of risk classification methods involve development of algorithms using machine learning applications as described above. The machine learning methods include but are not limited to random forest, gradient boosting, neural networks as well as classification and regression trees. The classification method uses any combination of input from demographic, medical, and electrophysiologic information obtained from subjects with known outcomes for sudden cardiac death in order to train and test classification algorithms. Validation of the risk prediction algorithm can be achieved via prospective studies of independent cohorts of subjects; however, retrospective study of a registry of subjects can also be used. Cardiac electrophysiologic information in the form of electrocardiogram recordings can be obtained once per subject to develop a baseline risk score and/or at time intervals in order to develop a time series in which changes in risk score can be monitored. Electrophysiologic information can be collected at regular, predefined time intervals or in response to external events, such as physician request, and are also viable for use in determining the risk score and classification.

The electrophysiologic data can include electrocardiogram recordings of varying time length. For example, recordings of 45 to 60 seconds in length can be obtained once per subject and/or at time intervals. Recordings of shorter or longer length may also be used and, for example, can range in time from 1 minute to 2 weeks of continuous cardiac electrophysiology monitoring. Use of electrocardiogram data can include application of software algorithms to process cardiac signals into cardiac associated metrics, such as but not limited to heart rate, heart rate variability, S-T segment elevation, premature ventricular contractions, heart rhythm morphology, early repolarization, etc.

Non-electrophysiologic data can include subject demographic information and medical history information. The subject demographic information and medical history information can include but is not limited to gender, age, body mass index, family history of heart disease, cardiac diagnosis, co-morbidity, and left ventricular ejection fraction.

Event estimation of risk scores for individual subjects can be obtained by applying machine learning algorithms to electrophysiologic data or to electrophysiologic and non-electrophysiologic data. Interpretation of the risk scores is dependent upon threshold settings, enabling classification of risk scores by clinically meaningful gradation of risk. Unique to each model algorithm, the threshold is determined and can be continuously refined using an available registry of subject data.

In some examples, thresholds for the classifier models can be determined by applying previously developed machine learning algorithms to historical data available in a registry of subject data with known outcomes for sudden cardiac death, including sudden cardiac arrest and asystole. Subjects can be chosen by any number of criteria, such as consecutive entry into the registry, cardiac diagnosis, gender, etc. The determination of a threshold can be based upon predetermined performance criteria, such as 95% specificity or other diagnostic test performance criteria. For example, in the case of 95% specificity, the risk scores from a group of subjects with negative outcome for the test criteria can be ordered by value and the cutoff for the 95th percentile determined using standard methods. Moreover, thresholds for other performance criteria such as sensitivity, positive predictive value, number needed to diagnosis, etc. can be predetermined in a similar manner.

Thresholds can be chosen to achieve any clinically meaningful level of specificity, sensitivity, positive predictive value, number needed to diagnose or other diagnostic performance characteristic. In an example, the threshold for interpretation of event estimation of risk scores is predefined in order to achieve performance at 95% specificity. This decision determines the levels of the other performance characteristics. For example, when 10,000 subjects are examined and the prevalence of sudden cardiac arrest is 1.4%, the corresponding threshold classifies 493 subjects as false positive and 9,367 subjects as true negative. If the sensitivity performance of the models is 20%, 28 subjects are classified as true positive and 112 are classified as false negative. In a similar fashion, additional performance characteristics, such as positive predictive value, negative predictive value, number need to diagnose, etc., can be specified in advance in order to achieve individual performance measures of predetermined clinical significance.

In some examples, an event estimation of risk score can be evaluated by incorporating electrophysiologic information collected at different times. The time series data can provide renewed risk scores at intervals that range from a few seconds or minutes to days. Use of multiple risk scores can be optimized to follow any number of approaches to determine the subject's overall risk for sudden cardiac death.

For example, any risk score occurring above the threshold can be used to classify a subject as presenting elevated risk. Moreover, other variables can be used to evaluate risk, such as but not limited to changes in risk values (whether increasing or decreasing), the length of time a subject remains above the risk threshold, or an area under the curve based approach.

Identification of event estimation of risk scores associated with true positive subjects can lead to actionable outcomes that impact the subject's health. The performance of the risk score can be valid for a range of times spanning from seconds or minutes to days leading to different recommended actions. In the event of a subject's risk score being above the threshold, possible actions that can be taken include but are not limited to shorter time interval between detection of tachyarrhythmia and defibrillation or disabling of the medical device's response buttons in order to ensure timely delivery of treatment.

In some examples, a subject's event estimation of risk score being above the threshold can lead to a direct notification to the subject, the subject's medical team or responsible third party such as a close family member. For example, a notification of the subject's elevated risk status can take the form of text message, email, or contact by telephone. Additional subject notification schemes can include use of the wearable medical device's audio and vibration alarm systems to prompt the patient to increase his or her adherence to wearing the device. Notification of elevated risk can also be sent to the subject's medical team, including a primary care physician and a cardiology specialist with recommendations that they contact their patient to evaluate the subject's adherence to optimized medical therapy.

Figure 8F:
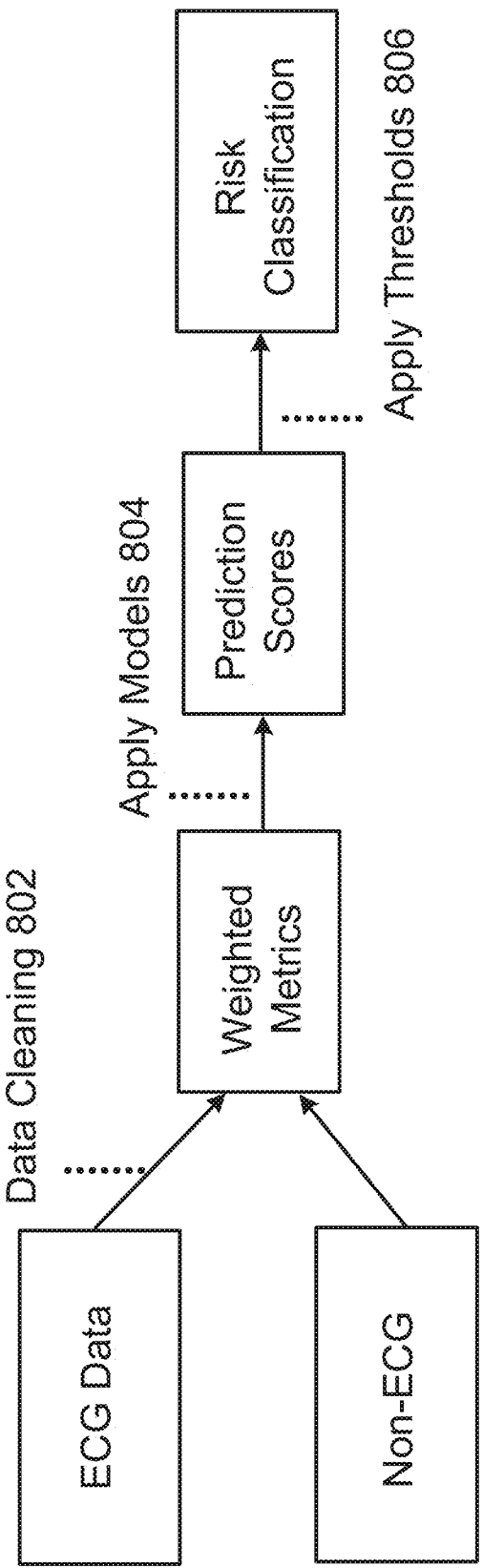
FIG. 8F is a flow chart of a process for determining event estimation of risk scores and corresponding classifications.

FIG. 8F is a flow chart of a process for determining event estimation of risk scores and corresponding classifications according to some embodiments. Input data from ECG and Non-ECG data sources are gathered and cleaned at stage 802 to provide a set of weighted metrics for each subject. Metrics can include but are not limited to measurement of heart rate, count of premature ventricular contractions, gender and age. At stage 804, models such as the predictive machine learning algorithms or classifiers are applied and event estimation of risk scores are generated. At stage 806, thresholds (e.g., predetermined thresholds) based upon performance criteria, such as sensitivity and specificity as described herein, are used to interpret a subject's event estimation of risk score by gradation of risk to classify the risk score.

Figure 8G:
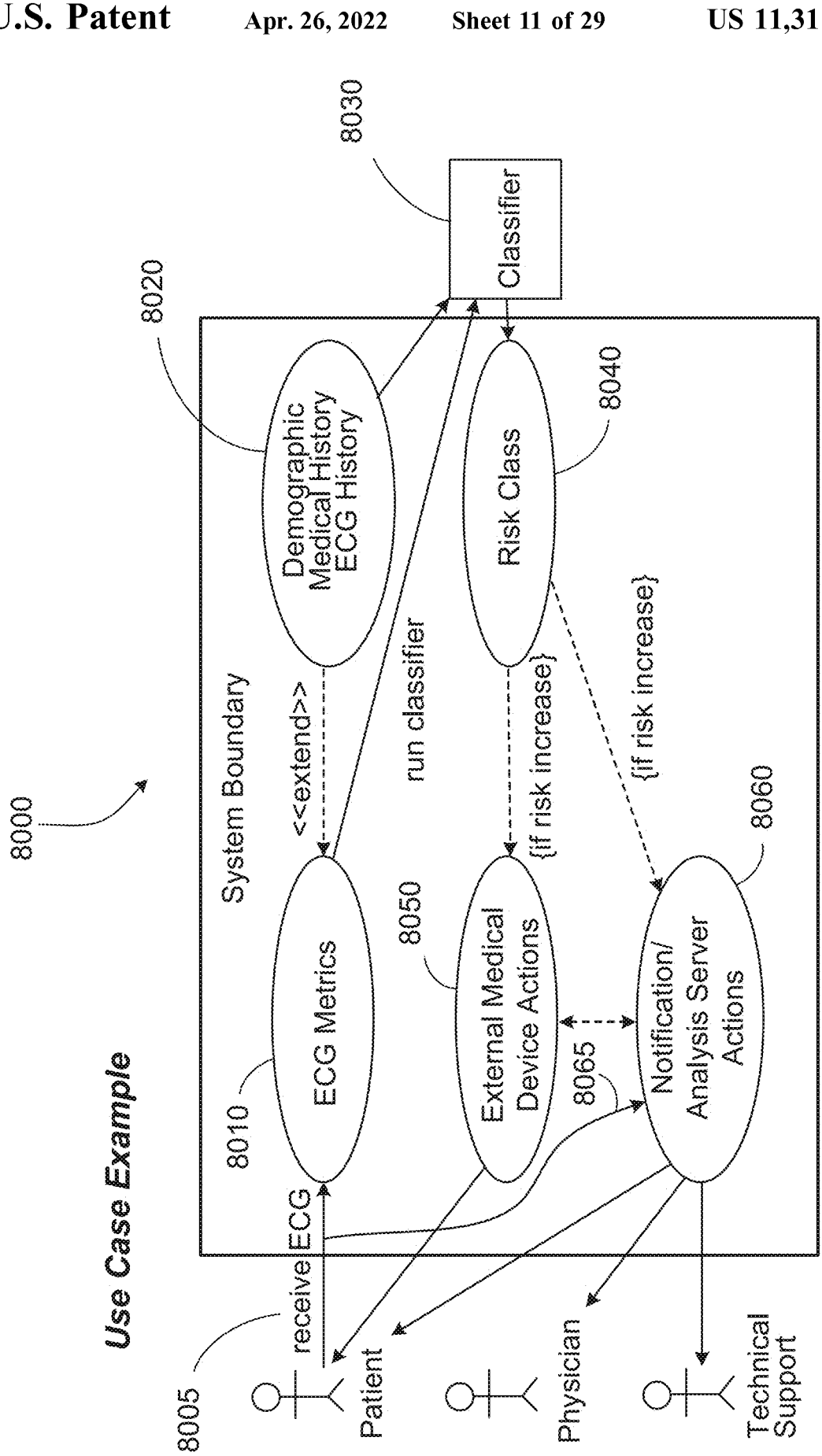
FIG. 8G is a block diagram of a system for determining, classifying, and notifying event estimation of risk scores.

FIG. 8G is a block diagram of a risk prediction system 8000 for determining, classifying, and notifying event estimation of risk scores according to some embodiments. In an example, a patient's electrocardiographic data (ECG) 8005 is received by the risk prediction system 8000, e.g., by an external medical device. Input of data across the system boundary, e.g., by the device monitoring the physiological parameters of the subject, results in development of ECG based metrics 8010, such as but not limited to heart rate, heart rate variability, S-T segment elevation, premature ventricular contractions, heart rhythm morphology, etc. When available, ECG metrics may be extended with demographic, medical history, and previously obtained ECG metrics 8020. The complete dataset of metrics are delivered to the classifier 8030, which calculates a risk score and returns a risk classification 8040 for that patient. In the event that the risk classification of the patient is elevated above that of the typical patient, e.g., above a threshold set for the classifier model (e.g., at thresholds set for elevated risk or elevated and immediate risk as described above), the system can prompt certain actions. For example, actions 8050 may be directed at the external medical device (e.g., the wearable defibrillator), such as but not limited to triggering changes in the controller so that a time from detection of sudden cardiac arrest to treatment is decreased. Moreover, detection of an increased risk class may prompt the system to notify 8060 the patient, a physician, a responsible third party, a medical team, and/or technical support of the change in risk. In this way, a patient in an increased risk class can be flagged for more frequent future observation. For example, in some implementations, depending on the risk classification, a caregiver and/or technical support may cause the external medical device to perform certain additional actions.

In some implementations, if the patient is classified as being at elevated risk, including the higher immediate risk classification, (e.g., at or above 0.425), the caregiver and/or technical support person may cause the external medical device to initiate real-time or substantially real-time streaming of the patient's ECG data 8005 (and/or other physiological data) to a remote server (e.g., arrow 8065) for additional monitoring and analysis. In some examples, a period of reporting and/or metric measurement and analysis for such a patient may be increased (e.g., from once every few or more hours, to once every hour). In some examples, additional monitoring and/or reporting of the patient's condition and various physiological parameters may be initiated for the duration of the period during which the patient remains in the elevated risk classification.

In some implementations, if the patient is classified as being at elevated risk but no immediate action is deemed necessary (e.g., at or above 0.425 but below 0.52 in the example above), the physician or technical support person may initiate more frequent reporting of the patient's physiological status (e.g., medical reporting of the patient's condition) or initiate streaming ECG data. Further, if the patient is placed in the immediate risk classification (e.g., at or above 0.52), the physician or technical support person may perform additional actions, e.g., including instructing more frequent checks of the external medical device and/or ensuring that downtime of the continuous monitoring is kept to a minimum.

Figure 11:
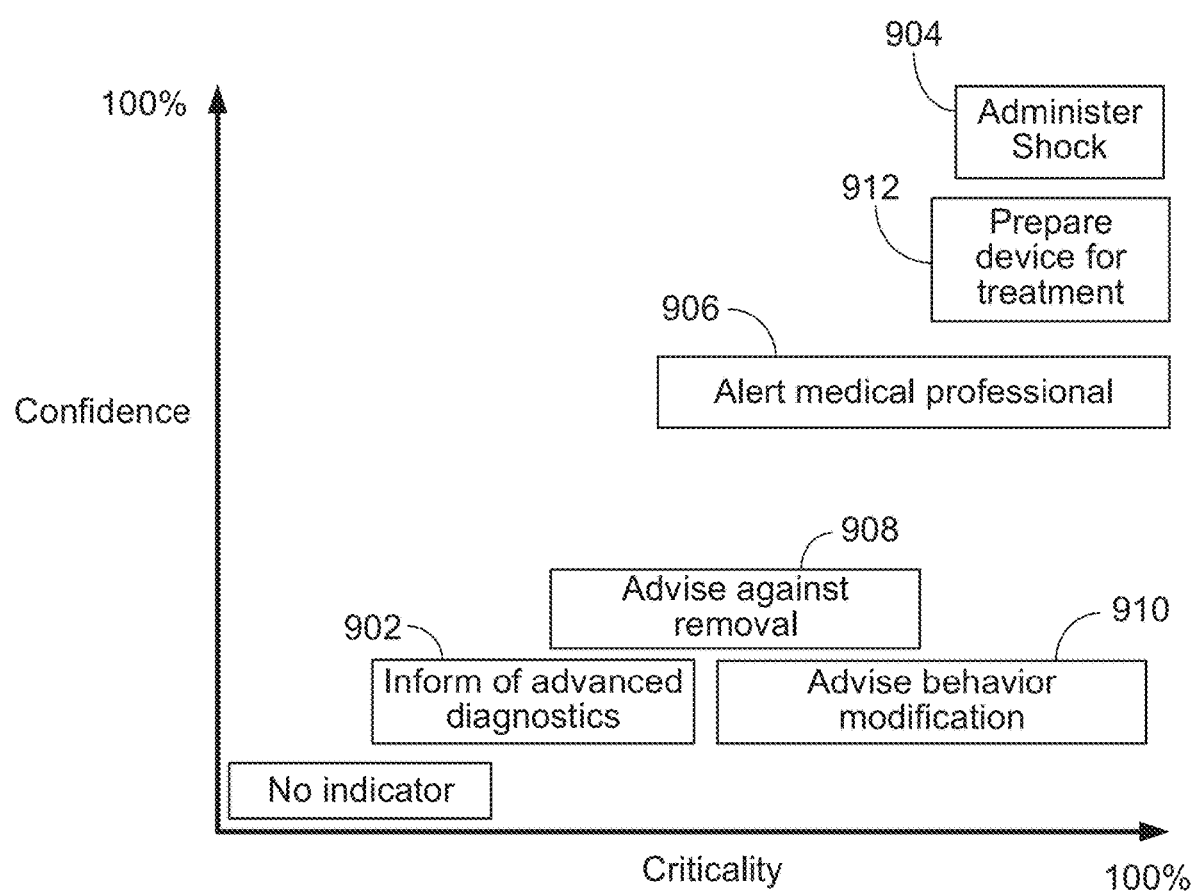
FIG. 11 is a chart graphing example actions based on criticality (risk) and confidence measures.

In the event of prediction for asystole, actions that may be taken are, but are not limited to, notification to the patient and a responsible third party to seek medical attention and notification to the responsible medical team of that patient's risk status. Other actions that can be taken are shown in FIGS. 11 and 12 and discussed in connection therewith herein.

Figure 8H:
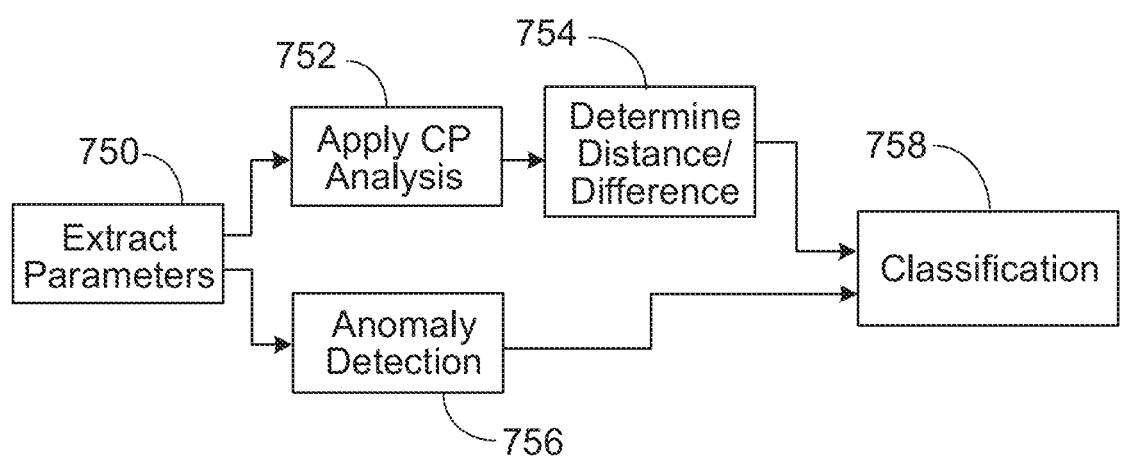
FIG. 8H is a flow chart of a state change analysis method for medical premonitory event estimation.

In some embodiments, the control unit 120 may calculate event estimation of risk scores by monitoring one or more physiological measurements or parameters of a subject to detect sudden changes in one or more states of the subject. Such changes may indicate instability in the underlying state of the subject and/or a change in statistics of a series of data on the subject. A state change may occur days, hours, minutes, or seconds before a medical event, including sudden cardiac arrest, respiratory arrest, asystole, non-sudden death, or other medical events. Referring to FIG. 8H, at stage 750, a plurality of physiological measurements or parameters may be extracted from an ECG signal of a subject (e.g., by the control unit 120). The control unit 120 may store the extracted physiological measurements and use the physiological measurements to analyze the ECG of the subject in real-time or through a post-hoc analysis. The control unit 120 may combine all or a portion of the extracted measurements or parameters into a multivariate parameter signal and process or analyze the multivariate parameter signal as described in more detail below.

The one or more physiological measurements extracted from the ECG signal may include one or more of heart rate, heart rate variability, PVC burden or counts, activity, noise quantifications, atrial fibrillation, momentary pauses, heart rate turbulence, QRS height, QRS width, changes in the size or shape of the morphology, cosine R-T, artificial pacing, corrected QT interval, QT variability, T wave width, T wave alternans, T-wave variability, ST segment changes, early repolarization, late potentials, fractionated QRS/HF content, and fractionated T wave/HF content.

The control unit 120 can detect fiducial points, e.g., points corresponding to P, Q, R, S, and T waves, in the ECG signal to extract individual measurements, e.g., QRS, PVC, etc., from the physiological parameter data. For example, a QT interval may provide a measure of heart failure of a subject, and the distance between the Q point and the T point may be determined and extracted from the physiological parameter signal.

Figure 8I:
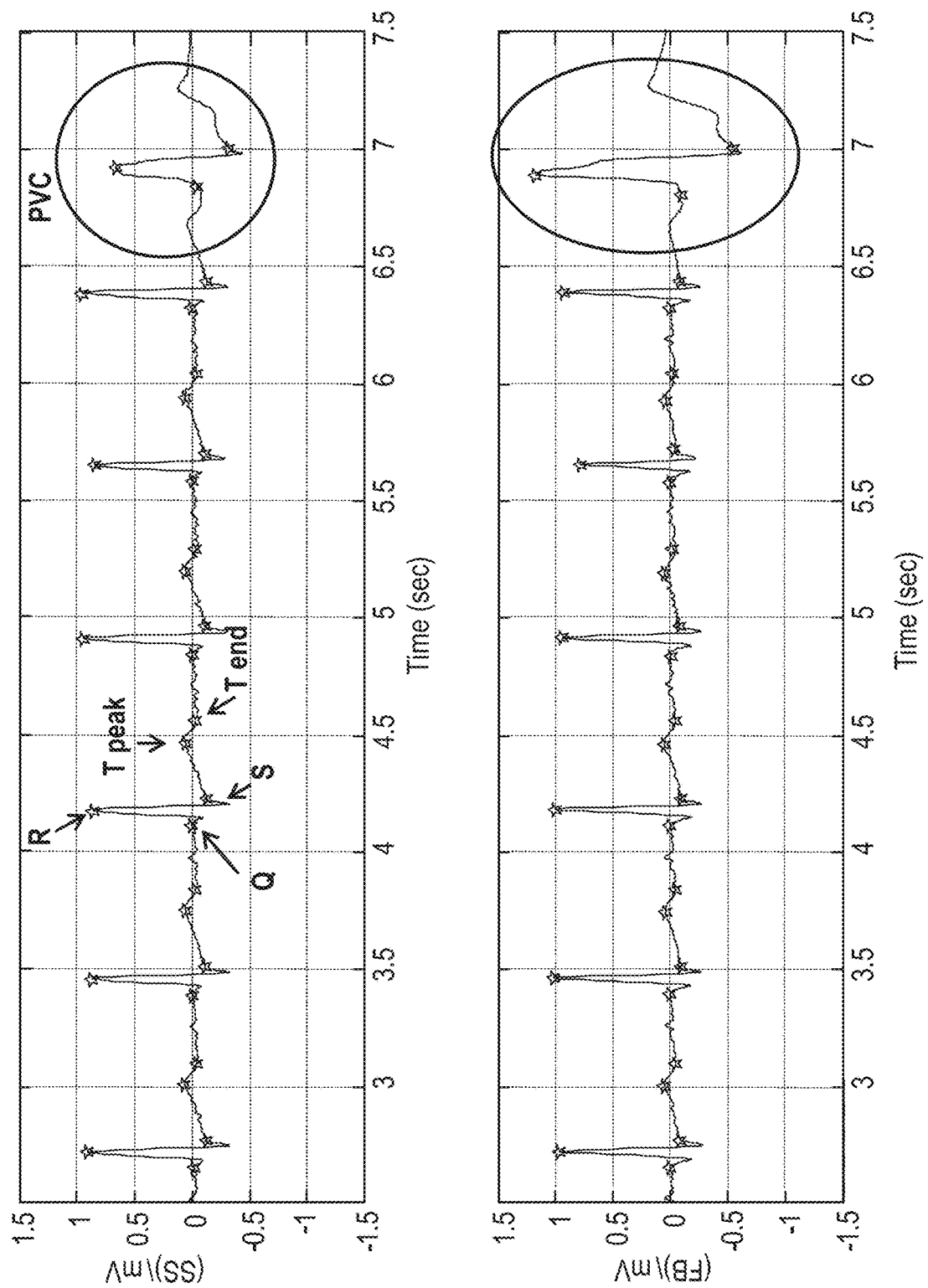
FIG. 8I shows a dual-lead ECG signal in a PVC parameter in the ECG signal is identified for extraction.

FIG. 8I shows a dual-lead ECG signal in which the control unit 120 has identified a PVC parameter in the ECG signal for extraction. For example, the control unit 120 may apply a QRS detector and a PVC detector to the ECG signal to extract QRS and PVC measurements. The extracted QRS and PVC measurements and/or the fiducial points determined by the QRS detector and the PVC detector may be used by the control unit 120 to identify and extract various other measurements or parameters in the ECG signal, e.g., HRV, RR intervals, etc. For example, output from the QRS detector and the PVC detector may be used by an AFIB detector, a pause detector, a pace detector, a morphology detector, a T wave detector, and/or any other detector in the control unit 120 that extracts measurements or parameters from the ECG signal. QRS, PVC, and other detectors are well-known in the art, for example, as described in (Kohler, Hennig, et al.), *The Principles of Software QRS Detection*, IEEE ENGINEERING IN MEDICINE AND BIOLOGY, (January/February 2002), the entire contents of which are incorporated by reference.

An accelerometer data stream may be received from an accelerometer located in the wearable medical device 100 or the medical support device 305 or elsewhere on the subject's body to detect if the subject is vertical or horizontal, or other activity and/or movement by the subject. For example, data regarding movement of the subject due to chest compressions or other movement of the subject may be utilized to remove ECG signal artifacts due to the movement of the subject from the ECG signal of the subject. The accelerometer may be a 3-axis accelerometer, which may be used to correlate orientation, for example, a degree of tilt of a supine subject with changes in the ECG of the subject.

In some implementations, a patient being identified as belonging to an increased risk class (e.g., a patient who is classified as being at "immediate risk" or "elevated risk") may cause one or more actions to occur. For example, the medical device may adjust one or more operational parameters in response to the patient being identified as belonging to an increased risk class. In some implementations, the medical device can adjust one or more threshold values for determining whether a medical event has occurred or is likely to occur. For example, if the patient is prone to a particular cardiac condition, the medical device may relax one or more threshold requirements for physiological parameters used to diagnose the particular cardiac condition (e.g., to minimize false negatives).

In some implementations, one or more non-essential functions of the medical device can be disabled, or the frequency of execution of non-essential functions may be minimized, in response to a patient being identified as belonging to an increased risk class. For example, the medical device may enter a power conservation mode in which only essential medical operations continue to run. In some implementations, the medical device may refrain from checking for and installing automatic updates (e.g., to the software and/or firmware). In some implementations, the medical device may reduce the timeout of display devices and other visual devices that may consumer a relatively large amount of battery power. In some implementations, the medical device may refrain from or reduce the frequency of performing self-checks.

Referring again to FIG. 8H, at stage 752, the control unit 120 may apply a change point (CP) analysis to the extracted measurements or parameters, which may be represented as the multivariate parameter signal, to determine one or more change points. Mathematical techniques may be used to analyze a data stream of the multivariate parameter signal to determine if a change has occurred, a nature of the change, a significance level of the change, and/or a degree of confidence that the change has occurred. Each of these factors may be used to determine what, if any, action is appropriate in response to a detected change. Generally, methods for detecting changes in the parameters or characteristics of a subject may include determining initial statistical characteristics of a signal, and analyzing the signal for any significant, sustained changes. For example, known techniques for change point analysis are described by (M. Basseville & I. Nikiforov, (1993). *Detection of Abrupt Changes: Theory and Application*. Prentice Hall, Englewood Cliffs, N.J.) and (Pettitt A. N., (1980). *A simple cumulative sum type statistic for the change point problem with zero-one observations*. Biometrika, 67:79-84), the contents of which are hereby incorporated by reference in their entirety. Other known methods for change point analysis, such as Shewhart control charts, may be employed for detecting changes in the characteristics and assessing whether a detected change is of a sufficient magnitude.

Figure 8J:
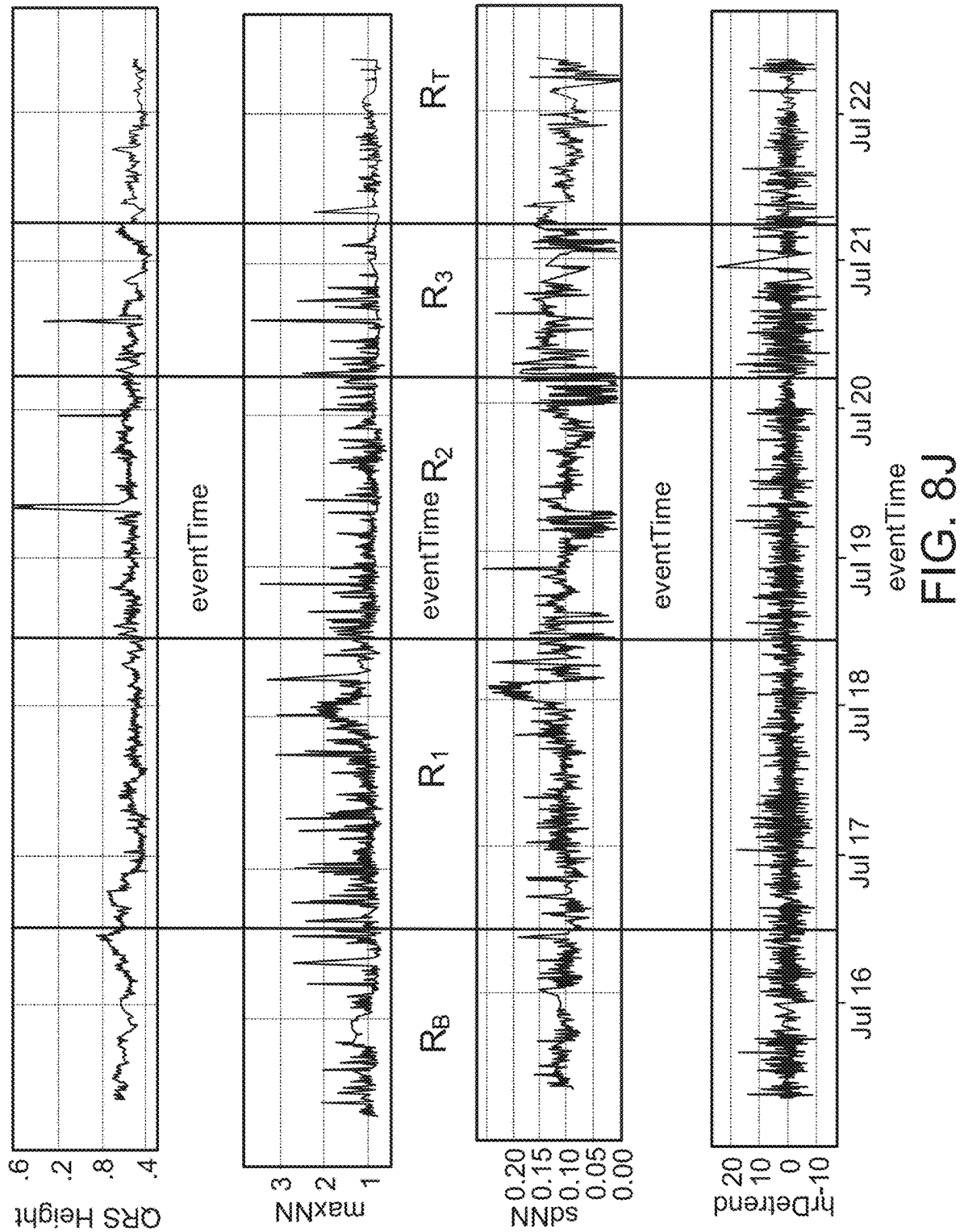
FIG. 8J shows an example multivariate parameter signal including a change point.

The control unit 120 may determine a baseline of the multivariate parameter signal on an interval from the start of the signal to the first or any subsequent change point or on an interval from the start of the signal to a desired timepoint. The control unit 120 may apply a distance analysis at stage 754 at various time intervals to the extracted parameters of the multivariate parameter signal with respect to the baseline or any other period. The detected change points or other arbitrary points in time may be used to determine the time intervals. For example, the time intervals may be situated about corresponding change points in the multivariate parameter signal. As shown in FIG. 8J, example extracted parameter signals, e.g., QRS height, maxNN, sdNN, and detrended heart rate, which form a multivariate parameter signal, may be broken into time intervals. For example, time interval $R_2$, e.g., eventTime, may be associated with a change point of the multivariate parameter signal. The control unit 120 can calculate a variant, a mean, a median, a standard deviation, or other statistical value of the multivariate parameter signal for each time interval and determine whether a distance of the statistical value for the individual time interval from the baseline satisfies one or more thresholds. For example, a mean calculated for a given time interval $R_i$, which is associated with a change point in the multivariate parameter signal, can be compared to a baseline $R_B$, which is determined based on a time interval from the start the multivariate parameter signal to a first change point detected therein, to determine a distance between the two scores, i.e., $D_i = R_i - R_B$, where $R_B$ is the baseline score, $R_i$ is the score for an interval i, and $D_i$ is the distance between the two scores for the interval i.

Figure 8K:
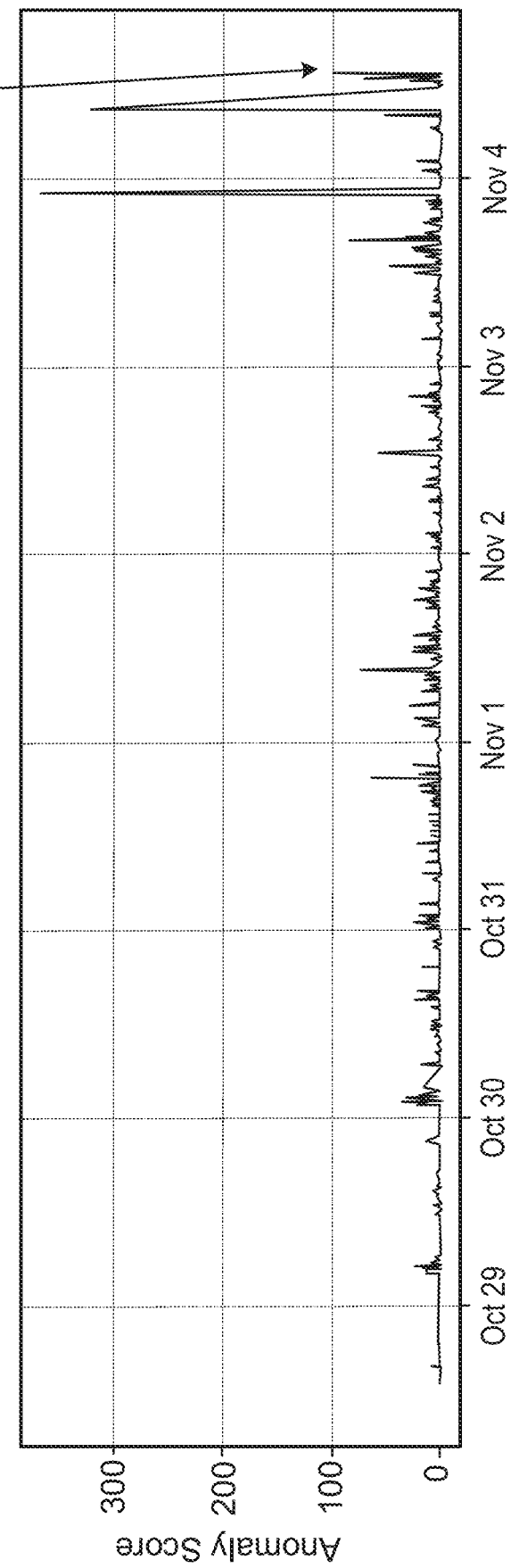
FIG. 8K shows a multivariate summation of example anomaly scores for a treated subject.

The determined distance can be used in combination with an anomaly score output from an anomaly detection, e.g., a neural network, a density based technique, a support vector machine, a cluster analysis, an ensemble technique, or any other known process for anomaly detection, and applied to the multivariate parameter signal by a classifier in the control unit 120 to determine the event estimation of risk score of the subject. The control unit 120 may determine the anomaly score on a continuous basis or at a set interval, e.g., at set time intervals or at time intervals corresponding to each change point. FIG. 8K shows a multivariate summation of example anomaly scores for a treated subject. For example, in parallel with the change point analysis at stage 752 and the distance analysis at stage 754 of FIG. 8H, the control unit 120 may apply an anomaly detection to the multivariate parameter signal at stage 756. For example, the control unit 120 may train a neural network on the baseline period of the multivariate parameter signal and apply the trained neural network to the multivariate parameter signal to determine the anomaly score of the subject. Accordingly, metrics or parameters for determining the event estimation of risk score are generated by both the change point analysis and the neural network. The control unit 120 may execute three separate analyses of the multivariate parameter signal including the baseline parameter difference measurement, the combined anomaly detection magnitude value, and raw single-parameter outputs from the anomaly detection algorithm. These three analyses, which can have multiple parameters as an output, can each be fed into a classifier or other decision logic that may take the form of, logistic regression, fuzzy logic, traditional "if then else", or "thresholding" logic, to determine the event estimation of risk score. FIG. 8L shows state change results including sensitivity and specificity percentages for predicting medical premonitory events from an example testing set of two hundred patients.

At stage 758, the classifier in the control unit 120 receives the distances and anomaly scores corresponding to each time interval and determines the event estimation of risk score based thereon. The classifier in the control unit 120 classifies the distances and corresponding anomaly scores for the time intervals using one or more machine learning processes.

Decision thresholds of the classifier may be trained using machine learning. For example, the classifier may be a random forest classifier that uses a number of decision trees, in order to improve the classification rate. Decision tree learning is a method commonly used in data mining to create a model that predicts the value of a target variable based on several input variables. Each interior node in a decision tree corresponds to one of the input variables and each leaf represents a value of the target variable given the values of the input variables represented by the path from the root to the leaf. A decision tree thus provides a simple representation for classifying examples and is one of the most successful techniques for supervised classification learning.

Figure 8M:
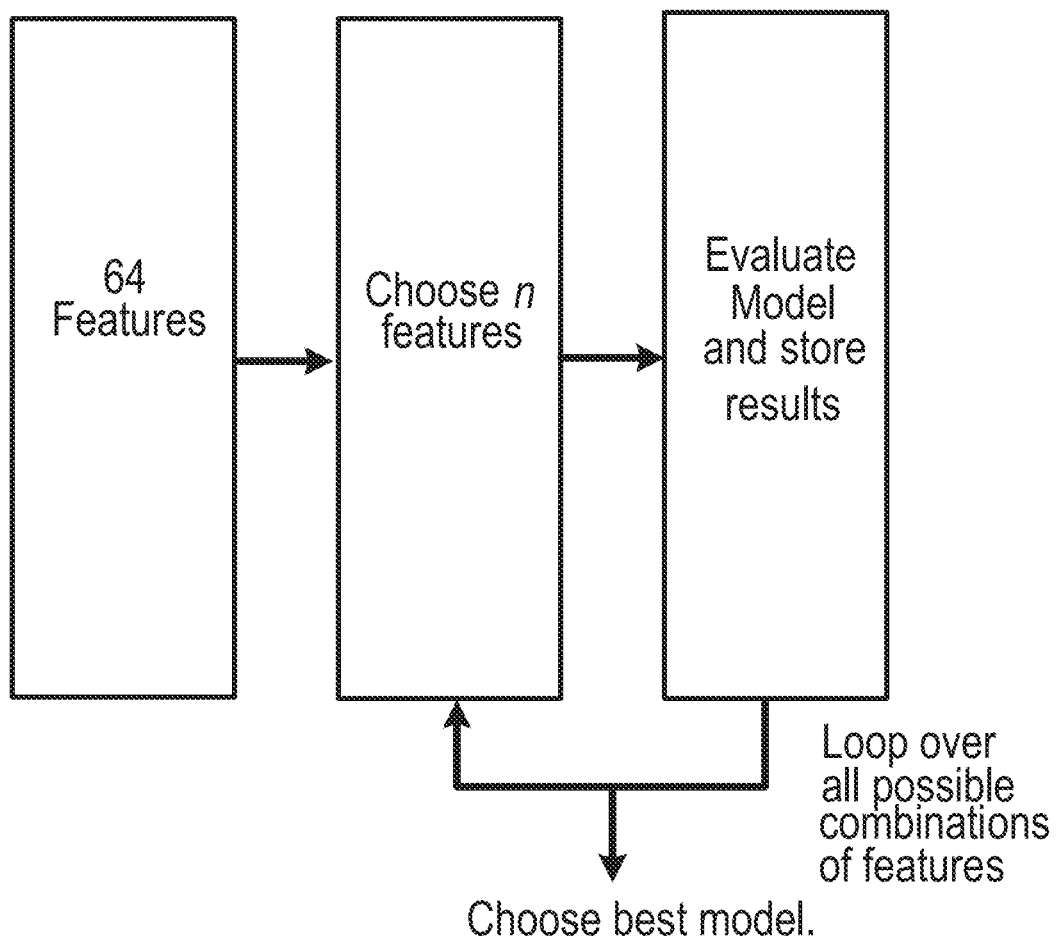
FIG. 8M shows a multivariate feature selection process.

A process for calculating event estimation of risk scores as described in FIG. 8H may be defined by various models. FIG. 8M shows a multivariate feature selection process for determining which metrics of a plurality of metrics extracted from the multivariate parameter signal to use to in a model to determine the event estimation of risk score. The multivariate feature selection processes can evaluate models for all possible combinations of the extracted parameters to determine the best parameters to use for the model.

A real time predictive model defining the process as described in FIG. 8H may optimize the area under the multivariate parameter curve for the optimized parameters to determine a receiver operator curve.

Including additional clinical history variables may further enhance the real-time model presented in FIG. 8H. The medical history variables may include one or more of age, BMI, sex, etc. In some embodiments, the patients may be clustered according to the medical history variables. Different real-time models may be developed for each of the clusters generated from the medical history analysis.

A baseline model defining the process as described in FIG. 8H may evaluate only a first time interval against the baseline period. For example, the baseline model may evaluate only the first 12 hours of the physiological parameter data for the subject, e.g., compare the first six hours of baseline to the second six hours of the first time interval, to predict risk within a future time period, e.g., the next week or two.

The event estimation of risk scores may be calculated using a scoring model or a mathematical model, such as a model based on logistic regression. Exemplary logistic regression models that may be used to calculate the event estimation of risk scores include univariate analysis and multivariate non-linear regression.

The control unit 120 may apply a logistic regression mathematical model to data from samples of cardiovascular and non-cardiovascular subjects. The logistic regression mathematical model may be fitted separately with a combination of demographic parameters, (e.g., age), vital signs, and other ECG parameters for the cardiovascular and non-cardiovascular subjects. Estimation of risk may be analyzed through Receiver Operating Characteristic (ROC) analysis, Sensitivity analysis, Specificity analysis, Positive Predictive Value (PPV) analysis, and/or Negative Predictive Value (NPV) analysis. Based on the logistic model, an event estimation of risk score, which may include a score from 0-100%, is generated at regular intervals, for example, on the order of every 10 seconds. Alternatively, the intervals at which the event estimation of risk score is calculated may be a function of the perceived risk. For example, the frequency of the calculation of an event estimation of risk score may be increased as the estimation of risk score of previous intervals increases, e.g., upon a determination that the event estimation of risk score for a previous interval satisfies a threshold level for increasing the frequency of the calculation.

The log-logistic distribution, also known as the Fisk distribution, which is a versatile function, provides a parametric model for survival analysis. Unlike the more commonly used Weibull distribution, the log-logistic distribution may have a non-monotonic hazard function: when a shape parameter $\beta > 1$, the hazard function is unimodal (when the shape parameter $\beta \leq 1$, the hazard decreases monotonically). The cumulative distribution function may be written in closed form, which is particularly useful for analysis of survival data with censoring. The loglogistic distribution may be used as a basis of an accelerated failure time model by allowing a scale parameter $\alpha$, which may also be the median of the distribution, to differ between groups, or more generally by introducing covariates that affect the scale parameter $\alpha$ but not the shape parameter $\beta$ by modeling log(a) as a linear function of the covariates.

The survival function is represented by the following Equation (4):

$$S(t)=1-F(t)=[1+(t/\alpha)^\beta]^{-1} \quad (4)$$

wherein S(t) is the survivability of the subject as a function of time, e.g., S(t) may a property of any random variable that maps a set of events, usually associated with mortality or failure of some system, e.g., medical premonitory events, onto time, the survivability function S(t) captures the probability that the system, e.g., subject, will survive, e.g., not experience a medical premonitory event, beyond a specified time t; F(t) is the failure distribution as a function of time t, which is a cumulative distribution function that describes the probability of failure (at least) up to and including time t; t is time; α is the scale parameter; and β is the shape parameter.

The hazard function is thus represented by the following Equation (5):

$$h(t) = \frac{f(t)}{S(t)} = \frac{(\beta/\alpha)(t/\alpha)^{\beta-1}}{1+(t/\alpha)^\beta} \quad (5)$$

where h(t) is hazard rate or hazard function as a function of time, which becomes the instantaneous failure rate as Δt tends to zero; f(t) is a density function as a function of time t, which is a density of a continuous random variable, i.e., a function that describes the relative likelihood for the random variable to take on a given value, S(t) is the survival function of Equation (4), t is time, α is the scale parameter, and β is the shape parameter. Confidence intervals and confidence bands may be calculated for the survival function S(t) and/or the hazard function h(t).

Separate event estimation of risk scores are calculated for different time periods. The time intervals may be more finely spaced, such as on a minute, a second or a millisecond basis, to provide estimation of risk scores that are effectively continuous, for example, as shown in FIG. 6B. The wearable medical device 100 may display the event estimation of risk scores as a list, may display one or more scores from the list based on user input selection from the user, and/or may show the risk displayed as a curve on the display. The wearable medical device 100 may thus perform time-dependent event estimation of risk calculation and evolution and display the results to the subject or medical professional.

Figure 9:
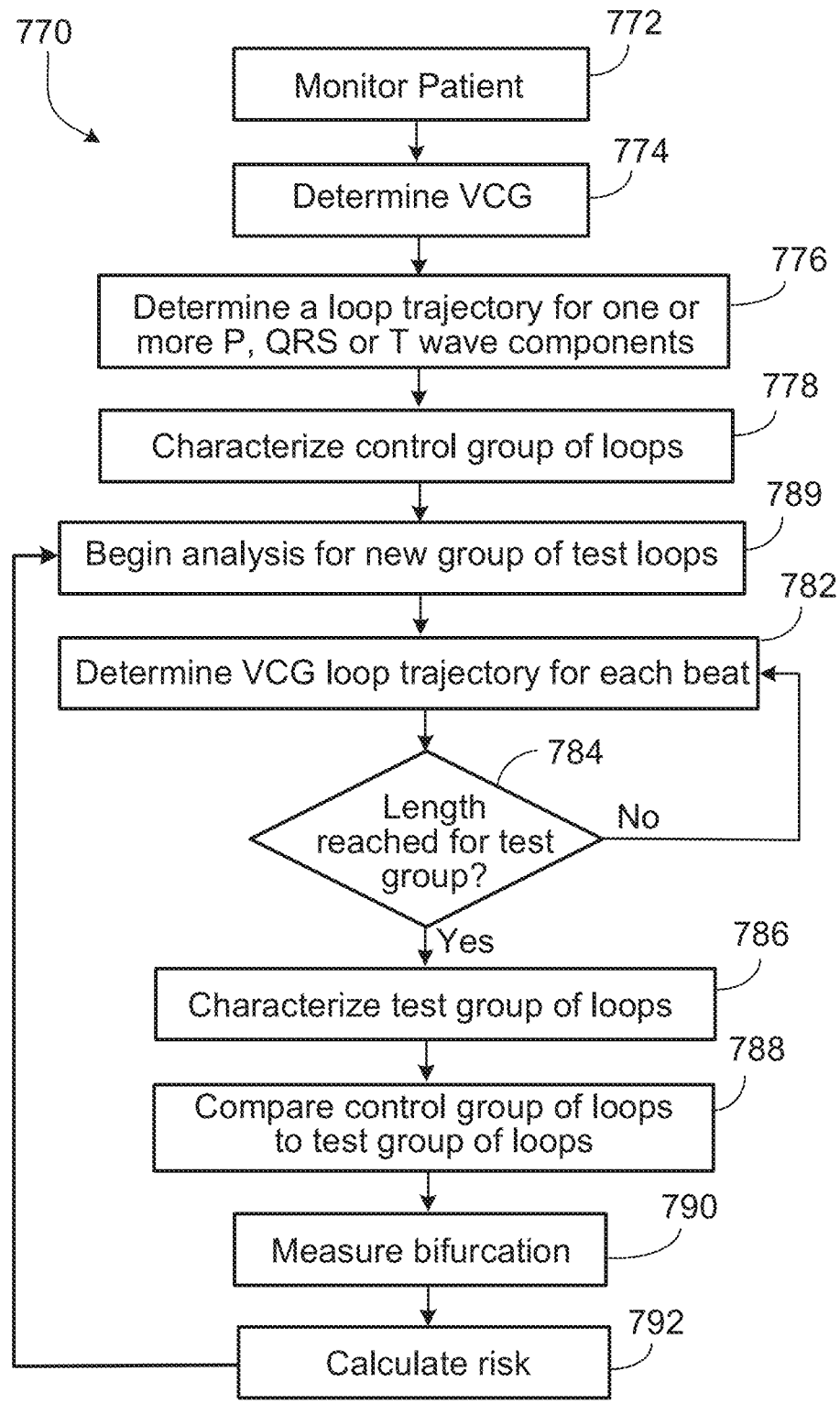
FIG. 9 is a flow chart of a vectorcardiographic vector loop bifurcation.

The control unit 120 may perform vectorcardiographic vector loop bifurcation as described in U.S. Provisional Patent Application No. 61/945,424 incorporated by reference herein in its entirety. Referring now to FIG. 9, an example method 770 is shown for determining a cardiac risk indicator based on identification of T wave bifurcations. In one embodiment, the method 770 is implemented by the wearable medical device 100 or medical support device 305. However, other embodiments are possible.

At a stage 772, a patient is monitored, by recording one or more types of physiological data, including an ECG signal. The ECG signal may be received from any appropriate source of patient ECG data. For example, ECG data may be received real time from two or more or three or more ECG electrodes attached to a patient or previously recorded data can be received from a storage device. ECG data can be of any appropriate type. ECG data can be recorded from a plurality of lead sites on the surface of the patient's body. In some implementations, standard 12-lead ECG recordings (e.g., leads I, II, III, aVR, aVF, aVL, V1, V2, V3, V4, V5 and V6) can be derived based on signals retrieved with ten ECG electrodes. Any appropriate number of ECG electrodes, attached to appropriate body sites, can be used. Examples of other ECG lead systems include the "Frank" electrode lead system (e.g., six electrodes), the McFee-Parungao Lead System, the SVEC III Lead System, Fischmann Barber-Weiss Lead System, and the Nelson Lead System. Other examples include the addition of rightsided precordial leads, posterior leads, leads placed in higher or lower intercostal spaces, and the like.

In some implementations, information about the source of the ECG data can be provided to the wearable medical device 100 or the medical support device 305. For example, the wearable medical device 100 or the medical support device 305 may adapt the configuration of the display and/or analysis tools based on the source of the ECG data, such as the position of the ECG leads with respect to the heart, the body, and/or to other leads. In some implementations, the patient monitoring device can perform real time ECG signal preprocessing. Real time ECG signal pre-processing may include removing the DC component with a high-pass filter, amplifying the ECG signal, limiting the signal bandwidth with a low-pass filter and digitally sampling the ECG signal. In some implementations, the ECG signal is received together with additional patient data, including patient statistics, other physiological data recordings, medical history, physical exam findings and other medical information that might be requested by a user. Patient data may be used in conjunction with patient-specific ECG data for data processing and display, or it may be used to correlate information extracted from the ECG data. At stage 774, a VCG signal is determined (e.g., generated) based on the received ECG signal. ECG data provides a time-dependent voltage that describes the electrical activity of the heart, which is treated like a dipole having an origin at the center of the patient's heart. Multiple ECG lead sites provide different time dependent voltage waveforms that reflect the overall cardiac electrical activity. A time-dependent heart vector that represents the size and orientation of the timevarying electrical dipole may be calculated by approximating the electrical activity of the heart.

Additionally, at stage 774, three or more ECG leads can be used to generate the vectorcardiograph, typically using the X, Y, Z orthogonal components for the representation of the VCG vector. A conversion matrix can be used to convert a particular set of leads to the Vx, Vy, Vz orthogonal components of the VCG vector. In some implementations, a VCG heart vector may be derived from the ECG using an inverse transform (e.g., an inverse Dower matrix, Levkov matrix). Any conversion method can be used to generate the VCG heart vector based on the ECG data.

At stage 776, a loop trajectory including a portion of ECG cycle is determined. The portion of ECG cycle can be a P, QRS or T wave. Determining a portion of the ECG cycle can include detecting an onset of the portion of the ECG cycle and an end of the portion of the ECG cycle, isolating the portion of the ECG cycle based on detecting the onset of the portion of the ECG cycle and the end of the portion of the ECG cycle and filtering the isolated portion of the ECG cycle. The portion of ECG cycle can be determined for each cardiac cycle of the received ECG.

In some implementations, the information about the plurality of cardiac cycles is used to calculate a characterization of a plurality of cardiac cycles to generate the control loop trajectory; and to store the control loop trajectory. In some implementations, the characterization may include a spline estimation of the loop trajectories corresponding to a plurality of cardiac cycles.

Statistical shape analysis may be used to characterize the loop or groups of loops. For example, a control group of loop trajectories may be generated automatically at the beginning of the monitoring session. There may be a user input on the wearable medical device 100 or the medical support device 305 to allow for the user to manually initiate a new acquisition of the control group of loop trajectories. The control group may be composed of two or more ECG cycles, though more commonly will consist of 30 seconds up to 5 minutes of ECG data. The time period can be configured in the non-volatile storage memory of the patient monitoring device.

At stage 778, the control group of loops is characterized. An analysis (in some examples a statistical analysis) is performed on the loop trajectories for the different cardiac cycles. As such, the shape of the control loop represents a statistical representation, oftentimes in the form of a mean, of the shapes of observed loop trajectories during the control window.

In some examples, only odd beats or even beats are used to generate the control or test loop trajectories. In this way, the analysis may analyze for the effects of T-wave alternans. Thus, the control group may be every odd element in a time period, and the test group may be every even element in the same time period, or vice versa. This will provide a more accurate measure of T-wave alternans. In some implementations, the shape characteristics of the control and/or test groups may be determined using every kth loop, $L_k$, of the group under analysis. For instance, for k equal to 3, the control group would be composed of the first, fourth, seventh, tenth, etc. of the original control group. The test group may be composed of the 2nd, 5th, 8th, etc. following the end of the control group acquisition period. The test group may be updated every loop, e.g. 3rd, 6th, 9th, etc., then 4th, 7th, 10th, etc.

In some implementations, for any particular value of k, multiple subgroups of the control period interval may be created, for instance, for k=4, a subgroup can start at loop 1, 2, 3 or 4, to create 4 distinct groups of loops for characterization of the shape using such methods as statistical shape analysis. A single group from within these subgroups can be chosen as the control group by analyzing the statistical variance of the shape of the subgroups and choosing the subgroup that is the most self-consistent with the lowest variation in shape. Thus, for each interval up to about 8 or 10, or whatever is computationally practically given the state of the art with microprocessors, a control group can be created for each value of k, and at regular intervals, even as rapidly as every new loop, the test group may also be decomposed into the k subgroups and compared to the control subgroups for degree of trajectory bifurcation.

In some implementations, the characterization may be based on an average or median of loop trajectories corresponding to the plurality of cardiac cycles. At stages 780-786, the test group of loop trajectories is generated.

At stage 780, the analysis for a new group of test loops begins. This analysis of a new group of test loops may be based on a time threshold (e.g., a new set of 15 loops is analyzed every 10 minutes or every 30 minutes) or may be based on a physiological trigger such as an increased risk score or another factor indicative of a change in the status of the patient. At step 782, a VCG loop trajectory is determined for a particular beat that will be included in the set of test loops. For example, two or more ECG leads can be used to generate the vectorcardiograph, typically using the X, Y, Z orthogonal components for the representation of the VCG vector. At step 784, the system determines if the length for the test group has been reached. For example, the size of the test group may be based on a threshold number of loops and/or on a time based threshold. If the length has not been reached, the system continues to determine loop trajectories to add to the test group. If the length has been reached, at stage 786, the system characterizes the test group of loops.

The loop trajectories determined at stages 776 (control loops) and 782 (test loops) may be at least three dimensional. For example, a first dimension can include a first spatial component of the loop trajectory, a second dimension can include a second spatial component of the loop trajectory orthogonal to the first dimension and a third dimension can include a third spatial component of the loop trajectory orthogonal to the first dimension and the second dimension. In some implementations, the loop trajectory may include more than three dimensions. For example, a fourth dimension may include an additional physiological signal coregistered with the ECG signal.

At stage 788, the system compares the control group of loops to the test group of loops. At stage 790, the trajectory bifurcation is identified by comparing the test loop trajectory to a control loop trajectory. In some implementations, the trajectory bifurcation may be identified based on a statistical analysis. For example, a variation of the loop trajectory from the control loop trajectory that occurs for a portion of the ECG signal and exceeds the standard deviation of the control loop trajectory can be identified as a trajectory bifurcation. In some examples, the statistical analysis used for the identification of the trajectory bifurcation may be a non-Gaussian statistical analysis.

In some implementations, the action of trajectory bifurcation identification may include calculating an area of the loop trajectory and subtracting the area of the loop trajectory from an area of the control loop trajectory. In some implementations, the identification of the trajectory bifurcation leads to an automatic generation of a bifurcation.

In some implementations, stage 790 is repeated at least three times to compare the trajectory bifurcation of at least three consecutive cardiac cycles of the plurality of cardiac cycles to determine a trend of the trajectory bifurcation and based on the trend, to define an episodic trajectory bifurcation. The action of identifying the trajectory bifurcation can be repeated cyclically over multiple cardiac cycles. For example, the trajectory bifurcation may be identified for each recorded cardiac cycle, after the control loop trajectory is determined.

At stage 792, an event estimation of risk score may generated based on the identification of the trajectory bifurcation. In some implementations, the event estimation of risk score may include a cardiac risk score (e.g., a quantitative risk estimated value) based on the identification of the trajectory bifurcation.

The vector loop bifurcation measures may be combined with other subject health and demographic information to create a database of retrospective subject health and demographic information along with associated times and severities of medical degradation, such as cardiac arrest, prior to use of the system on real-time data with subjects. Utilizing modeling techniques well-known to those skilled in the art, such as either linear or non-linear regression analysis, the parameters for a survival function may be estimated, along with associated confidence intervals, such as the log-logistic function, also known as the Fisk distribution.

In some implementations, heart rate variability measures may be used in place of, or in addition to, vector loop bifurcation measures in combination with subject demographic and other information, such as described in U.S. Pat. No. 8,668,644, the content of which is hereby incorporated by reference in its entirety, where demographic parameters of age were used, along with vital signs parameters of temperature, pulse rate, respiratory rate, systolic blood pressure (SBP), diastolic blood pressure (DBP), SpO$_2$ and pain score, and HRV parameters of average RR interval, STD, average heart rate (avHR), standard deviation heart rate (sdHR), RMSS, nn50(count), pnn50(%), RR interval triangular index, TINN (ms), LS-VLF power (ms2), LS-LF power (ms2), LS-HF power (ms), LS-total power (ms2), LS-LF power (nu), LS-HF power (nu) and LS-LF/HF ratio.

In some embodiments, the control unit 120 applies a medical premonitory event estimation and detection class of algorithms that may be termed a "reverse maze" approach to calculate the event estimation of risk scores. A general concept is that mazes are sometimes easier to solve by going backwards from the maze destination point to the maze entrance. A reverse maze approach may use lesser intensity or less critical medical premonitory events to predict greater intensity or more critical medical premonitory events.

Medical premonitory events may be ordered in terms of level of intensity (or criticality) from less intense to more intense, as follows: 1) T-wave abnormalities; 2) ectopic beats; 3) runs of ectopic beats (scaled by quantity of ectopic beats); 4) runs of ventricular tachycardia (scaled by duration of run of tachycardia and/or number of ventricular beats); 5) ventricular fibrillation. A similar scale of medical premonitory event criticality may be used for bradycardia events and be ordered, as follows: 1) QRS duration increase; 2) decrease in heart rate (scaled by % decrease in heart rate); 3) intermittent heart block (scaled by duration of time in block); 4) complete heart block and ventricular escape (scaled by duration of block); 5) asystole.

There are some parameters that are continuous, such as T-wave measurements, heart rate, QRS width, pulse oximetry saturation, or other physiologic parameter measurements, as compared to parameters of events that are of discrete occurrences, such as ectopic beats. Therefore, in some embodiments, parameters that are measured on a more continuous basis may be used to increase the accuracy of the estimation of risk from the lesser criticality medical premonitory event to the next greater criticality medical premonitory event. A multidimensional parameter space may be an M-dimensional space, where M=J+K+L, where J is a number of elements of subject history and demographics; K is a number of physiologic parameters, such as vital sign measures, ECG, SpO$_2$, respiration rate, etc.; and L is a number of different event types. The 1×M dimensional vector traces a trajectory in space, where the rate of update of the individual parameters may be: 1) regular, such as with a machine-sampled sensor input, e.g., ECG; 2) semi-regular, such as with a vital signs parameter measured and input manually by a nurse or other caregiver; or 3) irregular events.

In some embodiments, thresholds for detecting a medical event of the "tangible", "intermediate level" or "higher order" type, may be defined during a training period of the reverse maze algorithm development, when working with databases of collected subject data and associated results. The thresholds may be set empirically to maximize detection performance, or alternatively, well-known statistical signal processing methods may be employed to automatically or semi-automatically set the thresholds to optimize detection performance and maximize performance measures, such as the Receiver Operator Characteristic (ROC). The training database may comprise substantially equal numbers of subjects who have experienced degradation of a medical condition—in the case of a cardiac event, a cardiac arrest—and subjects that have not experienced degradation of a medical condition.

The Reverse Maze methodology works backward from the degradation in the medical condition, in the case of subjects who have had a degradation, or from the end of a recorded file for subjects who have not had a degradation in a medical condition. The threshold levels are set, as described in this paragraph for the immediate precursor premonitory event to the cardiac arrest such that the sensitivity is maximized for detecting those immediate precursor premonitory events, and the specificity is maximized by not having those immediate precursor premonitory events appear anywhere in the files for the subjects that did not have cardiac arrests. It is preferable that the files for those subjects who did not have cardiac arrests be at least the length of the time period desired for the risk estimation. In files for which there are immediate precursor premonitory (IPP) events and where there are also cardiac arrests (IPPCA), probability of risk and time, and/or error bands may be calculated. For IPPCAs, thresholds can be set via the methods described above for the medical premonitory events that immediately precede the IPP. The process continues back in this manner and the thresholds are used to detect events of all types during application in real time with subjects.

During the training period of algorithm development, after the thresholds for event detection have been initially established, the database is divided into subjects who have had a degradation in a medical condition—in the case of a cardiac event, a cardiac arrest—and a separate set of subjects who have not had a degradation in a medical condition.

Using the M-dimensional parameter space, tracking algorithms used for such applications as missile and satellite tracking, for example, a Kalman filter or a particle filter, may be used for the estimation and prediction of the vector loop path. The location of the most recent event along with the estimation of the trajectory's direction and path are used to estimate the risk and degree of certainty (e.g. the confidence band) of a higher intensity medical premonitory event occurring at some point in the future. As more events of various types occur, the trajectory path and the estimation of the trajectory path into the future may be better estimated, and the confidence band on the estimation may be narrowed for more certainty in the estimation of risk.

A Kalman filter estimates a process by using a form of feedback control. The Kalman filter estimates the process state at some time and then obtains feedback in the form of (noisy) measurements. As such, the equations for the Kalman filter fall into two groups: time update equations and measurement update equations. The time update equations are responsible for projecting forward (in time) the current state and error covariance estimates to obtain the a priori estimates for the next time stage. The measurement update equations are responsible for the feedback, i.e., for incorporating a new measurement into the a priori estimate to obtain an improved a posteriori estimate. The time update equations may also be thought of as predictor equations, while the measurement update equations may be thought of as corrector equations. Indeed, the final estimation algorithm resembles that of a predictor-corrector algorithm for solving numerical problems.

In order to use the Kalman filter to estimate the internal state of a process given only a sequence of noisy observations, one must model the process in accordance with the framework of the Kalman filter. This means specifying the following matrices: $F_k$, the state-transition model; $H_k$, the observation model; $Q_k$, the covariance of the process noise; $R_k$, the covariance of the observation noise; and sometimes $B_k$, the control-input model, for each time-step, k. The Kalman filter model assumes the true state at time k is evolved from the state at (k−1) according to Equation (6):

$$x_k = F_k x_{k-1} + B_k u_k + w_k \tag{6}$$

wherein $F_k$ is the state transition model which is applied to the previous state $x_{k-1}$; $B_k$ is the control-input model which is applied to the control vector $u_k$; $w_k$ is the process noise which is assumed to be drawn from a zero mean multivariate normal distribution with covariance $Q_k$, i.e., $w_k \sim N(0, Q_k)$.

At time k an observation (or measurement) $z_k$ of the true state $x_k$ is made according to Equation (7):

$$z_k = H_k x_k + v_k \tag{7}$$

wherein $H_k$ is the observation model which maps the true state space into the observed space and $v_k$ is the observation noise which is assumed to be zero mean Gaussian white noise with covariance $R_k$, i.e., $v_k \sim N(0, R_k) v_k$. The initial state, and the noise vectors at each step $\{x_0, w_1, \ldots, w_k, v_1 \ldots v_k\}$ are all assumed to be mutually independent.

The Kalman filter is a recursive estimator. This means that only the estimated state from the previous time step and the current measurement are needed to compute the estimate for the current state. In contrast to batch estimation techniques, no history of observations and/or estimates is required. In what follows, the notation $\hat{x}_{n|m}$ represents the estimate of x at time n given observations up to, and including at time m n.

The state of the filter is represented by two variables: $\hat{x}_{k|k}$, the a posteriori state estimate at time k given observations up to and including at time k; $P_{k|k}$, the a posteriori error covariance matrix (a measure of the estimated accuracy of the state estimate).

The Kalman filter may be written as a single equation, however it is most often conceptualized as two distinct phases: "Predict" and "Update". The predict phase uses the state estimate from the previous time-step to produce an estimate of the state at the current time-step. This predicted state estimate is also known as the a priori state estimate because, although it is an estimate of the state at the current time-step, it does not include observation information from the current time-step. In the update phase, the current a priori prediction is combined with current observation information to refine the state estimate. This improved estimate is termed the a posteriori state estimate.

Typically, the two phases alternate, with the prediction advancing the state until the next scheduled observation, and the update incorporating the observation. However, this is not necessary; if an observation is unavailable for some reason, the update may be skipped and multiple prediction steps performed. Likewise, if multiple independent observations are available at the same time, multiple update steps may be performed (typically with different observation matrices $H_k$).

The Predicted (a priori) state estimate may be represented by the following Equation (8):

$$\hat{x}_{k|k-1} = F_k \hat{x}_{k-1|k-1} + B_k u_k \tag{8}$$

The Predicted (a priori) estimate covariance may be represented by the following Equation (9):

$$P_{k|k-1} = F_k P_{k-1|k-1} F_k^T + Q_k \tag{9}$$

The Innovation or measurement residual may be represented by the following Equation (10):

$$\tilde{y}_k = z_k - H_k \hat{x}_{k|k-1} \tag{10}$$

The Innovation (or residual) covariance may be represented by the following Equation (11):

The Optimal Kalman gain may be represented by the following Equation (12):

$$S_k = H_k P_{k|k-1} H_k^T + R_k \tag{12}$$

The Updated (a posteriori) state estimate may be represented by the following Equation (13):

$$\hat{x}_{k|k} = \hat{x}_{k|k-1} + K_k \tilde{y}_k \tag{13}$$

The Updated (a posteriori) estimate covariance may be represented by the following equation (14):

$$P_{k|k} = (I - K_k H_k) P_{k|k-1} \tag{14}$$

An initial task during the measurement update is to compute the Kalman gain $K_k$, and a next stage is to actually measure the process to obtain and generate an a posteriori state estimate by incorporating the measurement $Z_k$. A final stage is to obtain an a posteriori error covariance estimate $P_k$. After each time and measurement update pair, the process is repeated with the previous a posteriori estimates used to project or predict the new a priori estimates. This recursive nature is one of the very appealing features of the Kalman filter, and it makes practical implementations much more feasible than, for example, an implementation of a Wiener filter which is designed to operate on all of the data directly for each estimate. The Kalman filter instead recursively conditions the current estimate on all of the past measurements. Equation (13) is thus termed the predictor equation.

One primary limitation of the Kalman filter is that it models a linear system with Gaussian distribution, which is not often encountered in the physiological setting. An example of an algorithm to solve the problem of non-Gaussian, nonlinear filtering is the extended Kalman filter (EKF). The EKF is based upon the principle of linearizing the measurements and evolution models using Taylor series expansions. The series approximations in the EKF algorithm may, however, lead to poor representations of the nonlinear functions and probability distributions of interest. As a result, the EKF may diverge. Based on the hypothesis that it is easier to approximate a Gaussian distribution than it is to approximate arbitrary nonlinear functions, other researchers have developed a filter termed the unscented Kalman filter (UKF). It has been shown that the UKF leads to more accurate results than the EKF and that it generates much better estimates of the covariance of the states (the EKF often seems to underestimate this quantity). The UKF, however, has a limitation in that it does not apply to general non-Gaussian distributions, as is often the case with ECG spectral distributions. Sequential Monte Carlo methods, also known as particle filters overcome this limitation and allow for a complete representation of the posterior distribution of the states, so that any statistical estimates, such as the mean, modes, kurtosis and variance, may be easily computed. Particle filters may, therefore, deal with any nonlinearities or distributions. Particle filters rely on importance sampling and, as a result, require the design of proposal distributions that can approximate the posterior distribution reasonably well. In general, it is hard to design such proposals. The most common strategy is to sample from the probabilistic model of the state evolution (transition prior). This strategy, however, may fail if the new measurements appear in the tail of the prior or if the likelihood is too peaked in comparison to the prior.

Some other implementations use an estimator/predictor trajectory tracking technique known as the Unscented Particle Filter (UPF) as disclosed by Wan, Eric A. and van der Merwe, Rudolph, "The Unscented Kalman Filter for Nonlinear Estimation", (2000), the content of which is incorporated by reference in its entirety. For example, the following Table 2 provides Unscented Kalman Filter (UKF) equations that may be used to calculate an event estimation of risk score.

TABLE 2

Initialize with:

$$\hat{x}_o = E[x_o]$$

$$P_0 = E[(x_o - \hat{x}_o)(x_o - \hat{x}_o)_T]$$

$$\hat{x}_0^a = E[x^a] = [\hat{x}_o^T \ 0 \ 0]^T$$

$$P_0^a = E[(x_0^a - \hat{x}_0^a)(x_0^a - \hat{x}_0^a)_T] = \begin{bmatrix} P_0 & 0 & 0 \\ 0 & P_v & 0 \\ 0 & 0 & P_n \end{bmatrix}$$

For $k \in \{1, \ldots, \infty\}$,
Calculate sigma points:

$$X_{k-1}^a = \left[ \hat{x}_{k-1}^a \hat{x}_{k-1}^a \pm \sqrt{(L+\lambda)P_{k-1}^a} \right]$$

Time update:

$$X_{k|k-1}^x = F[\hat{x}_{k-1}^x, \hat{x}_{k-1}^v]$$

$$\hat{x}_k^- = \sum_{i=0}^{2L} W_i^{(m)} x_{i,k|k-1}^x$$

$$P_k^- = \sum_{i=0}^{2L} W_i^{(c)} [X_{i,k|k-1}^x - \hat{x}_k^-][X_{i,k|k-1}^x - \hat{x}_k^-]_T$$

$$y_{k|k-1} = H[x_{k|k-1}^x, x_{k-1}^n]$$

$$\hat{y}_k^- = \sum_{i=0}^{2L} W_{i(m)} y_{i,k|k-1}$$

Measurement update equations:

$$P_{\tilde{y}_k \tilde{y}_k} = \sum_{i=0}^{2L} W_{i(c)} [y_{i,k|k-1} - \hat{y}_k^-][y_{i,k|k-1} - \hat{y}_k^-]^T$$

$$P_{x_k y_k} = \sum_{i=0}^{2L} W_{i(c)} [X_{i,k|k-1} - \hat{x}_k^-][y_{i,k|k-1} - \hat{y}_k^-]^T$$

$$K = P_{x_k y_k} P_{\tilde{y}_k \tilde{y}_k}^{-1}$$

$$\hat{x}_k = \hat{x}_k^- + K(y_k - \hat{y}_k^-)$$

$$P_k = P_k^- - K P_{\tilde{y}_k \tilde{y}_k} K^T$$

where, $x^a = [x^T v^T n^T]$, $x^a = [(x^x) \ (x^v)^T (x^n)^T]^T$,
$\lambda$ = composite scaling parameter, L = dimension of augmented state,
$P_v$ = process noise cov., $P_v$ = measurement noise cov.,
$W_i$ = weights as calculated by a weighting equation.

For example, for an initialization: t=0, and for i=1, . . . N, draw states (particles) $x_0^{(i)}$ from the prior $p(x_0)$ and set, according to the following Equations (15), (16), (17), and (18):

$$\overline{x}_0^{(i)} = E[x_0^{(i)}] \qquad (15)$$

$$P_0^{(i)} = E[(x_0^{(i)} - \overline{x}_0^{(i)})(x_0^{(i)} - \overline{x}_0^{(i)})_T] \qquad (16)$$

$$\overline{x}_0^{(i)a} = E[x^{(i)a}] = [(\overline{x}_0^{(i)})_T \ 0 \ 0]^T \qquad (17)$$

$$P_0^{(i)a} = E[(x_0^{(i)a} - \overline{x}_0^{(i)a})(x_0^{(i)a} - \overline{x}_0^{(i)a})_T] = \begin{bmatrix} P_0^{(i)} & 0 & 0 \\ 0 & Q & 0 \\ 0 & 0 & R \end{bmatrix} \qquad (18)$$

For t=1,2, . . . , an importance sampling step: for i=1, . . . N: updates particles with the UKF according to the following Equations (19), (20), (21), (22), (23), (24), (25), (26), (27), (28), and (29):
Calculate sigma points:

$$x_{t-1}^{(i)\alpha} = [\overline{x}_{t-1}^{(i)\alpha} \overline{x}_{t-1}^{(i)\alpha} \pm \sqrt{(n_\alpha + \lambda P_{t-1}^{(i)\alpha}}] \qquad (19)$$

Predict future particle (time update)

$$x_{t|t-1}^{(i)x} = f(x_{t-1}^{(i)x}, x_{t-1}^{(i)v}) \overline{x}_{t|t-1}^{(i)} = \sum_{j=0}^{2n_\alpha} W_j^{(m)} X_{j,t|t-1}^{(i)x} \qquad (20)$$

$$P_{t|t-1}^{(i)} = \sum_{j=0}^{2n_\alpha} W_j^{(c)} [X_{j,t|t-1}^{(i)x} - \overline{x}_{t|t-1}^{(i)}][X_{j,t|t-1}^{(i)x} - \overline{x}_{t|t-1}^{(i)}]_T \qquad (21)$$

$$\gamma_{t|t-1}^{(i)} = h(x_{t-1}^{(i)x}, x_{t-1}^{(i)n}) \overline{y}_{t|t-1}^{(i)} = \sum_{j=0}^{2n_\alpha} W_j^{(m)} \gamma_{j,t|t-1}^{(i)} \qquad (22)$$

Incorporate new observation (measurement update)

$$P_{\tilde{y}_t \tilde{y}_t} = \sum_{j=0}^{2n_\alpha} W_j^{(c)} [y_{j,t|t-1}^{(i)} - \overline{y}_{t|t-1}^{(i)}][\gamma_{j,t|t-1}^{(i)} - \overline{y}_{t|t-1}^{(i)}]^T \qquad (23)$$

$$P_{x_t y_t} = \sum_{j=0}^{2n_\alpha} W_j^{(c)} [x_{j,t|t-1}^{(i)} - \overline{x}_{t|t-1}^{(i)}][\gamma_{j,t|t-1}^{(i)} - \overline{y}_{t|t-1}^{(i)}]^T \qquad (24)$$

$$K_t = P_{x_t y_t} P_{\overline{y}_t \overline{y}_t}^{-1} \overline{x}_t^{(i)} = \overline{x}_{t|t-1}^{(i)} + K_t(y_t - \overline{y}_{t|t-1}^{(i)}) \qquad (25)$$

$$\hat{P}_t^{(i)} = P_{t|t-1}^{(i)} - K_t P_{\overline{y}_t \overline{y}_t} K_t^T \qquad (26)$$

Sample $\hat{x}_t^{(i)} \sim q(\hat{x}_t^{(i)} | x_{0:t-1}^{(i)}, , y_{1:t}) = \mathcal{N}(\overline{x}_t^{(i)}, \hat{P}_t^{(i)})$ (27)

Set $\hat{x}_{0:t}^{(i)} \triangleq (x_{0:t-1}^{(i)}, \hat{x}_t^{(i)})$ and $\hat{P}_{0:t}^{(i)}(P_{0:t-1}^{(i)}, \hat{P}_t^{(i)})$ (28)

For i=1, . . . N, evaluate the importance weights up to a normalizing constant:

$$w_t^{(i)} \propto \frac{p(y_t | \hat{x}_t^{(i)}) p(\hat{x}_t^{(i)} | \hat{x}_{t-1}^{(i)})}{q(\hat{x}_t^{(i)} | x_{0:t-1}^{(i)}, y_{1:t})} \qquad (29)$$

For i=1, . . . N, normalize the importance weights.
A selection step is performed according to the following Equations (30), (31), (32), and (33):
Multiply/Suppress particles, $$(\hat{x}_{0:t}^{(i)}, \hat{P}_{0:t}^{(i)}) \qquad (30)$$

with high/low importance weights, $$\tilde{w}_t^{(i)} \qquad (31)$$

respectively, to obtain N random particles.
a) Output: The output of the algorithm is a set of samples that can be used to approximate the posterior distribution as follows:

$$p(x_{0:t} | y_{1:t}) \approx \hat{p}(x_{0:t} | y_{1:t}) = \frac{1}{N} \sum_{i=1}^{N} \delta_{(x_{0:t}^{(i)})}(dx_{0:t}) \qquad (32)$$

Resulting in the estimate of, $$E(g_t(x_{0:t})) = \int g_{t(x_{0:t})} p(x_{0:t} | y_{1:t}) dx_{0:t} \approx \frac{1}{N} \sum_{i=1}^{N} g_{t_{(x_{0:t}^{(i)})}} \quad (33)$$

for some function of interest, $g_t$, for instance the marginal conditional mean or the marginal conditional covariance or other moment.

After the occurrence of a lesser intensity medical premonitory event, multiple potential greater and lesser medical premonitory events "lurk" out in the future multi-parameter space. Based on the estimated vector trajectory using one or more of the methods described herein, the likelihood or probability of occurrence of any one of those future medical premonitory events may be calculated. The medical premonitory events may be viewed as sequentially oriented "landmarks" or letters, and decoding methods such as Viterbi or Hidden Markov Modeling (HMM) methods may also be employed to enhance estimation and detection accuracy. The uncertainty of the vector trajectory estimate as well as medical premonitory event estimate may be refined using one or more refinement methods, for example, ensemble forecasting.

Ensemble forecasting is a numerical prediction method that is used to attempt to generate a representative sample of the possible future states of a dynamical system. Ensemble forecasting is a form of Monte Carlo analysis: multiple numerical predictions are conducted using slightly different initial conditions that are all plausible given the past and current set of observations, or measurements. Sometimes the ensemble of forecasts may use different forecast models for different members, or different formulations of a forecast model. The multiple simulations are conducted to account for the two usual sources of uncertainty in forecast models: (1) the errors introduced by the use of imperfect initial conditions, amplified by the chaotic nature of the evolution equations of the dynamical system, which is often referred to as sensitive dependence on the initial conditions; and (2) errors introduced because of imperfections in the model formulation, such as the approximate mathematical methods to solve the equations. Ideally, the verified future dynamical system state should fall within the predicted ensemble spread, and the amount of spread should be related to the uncertainty (error) of the forecast.

Figure 10:
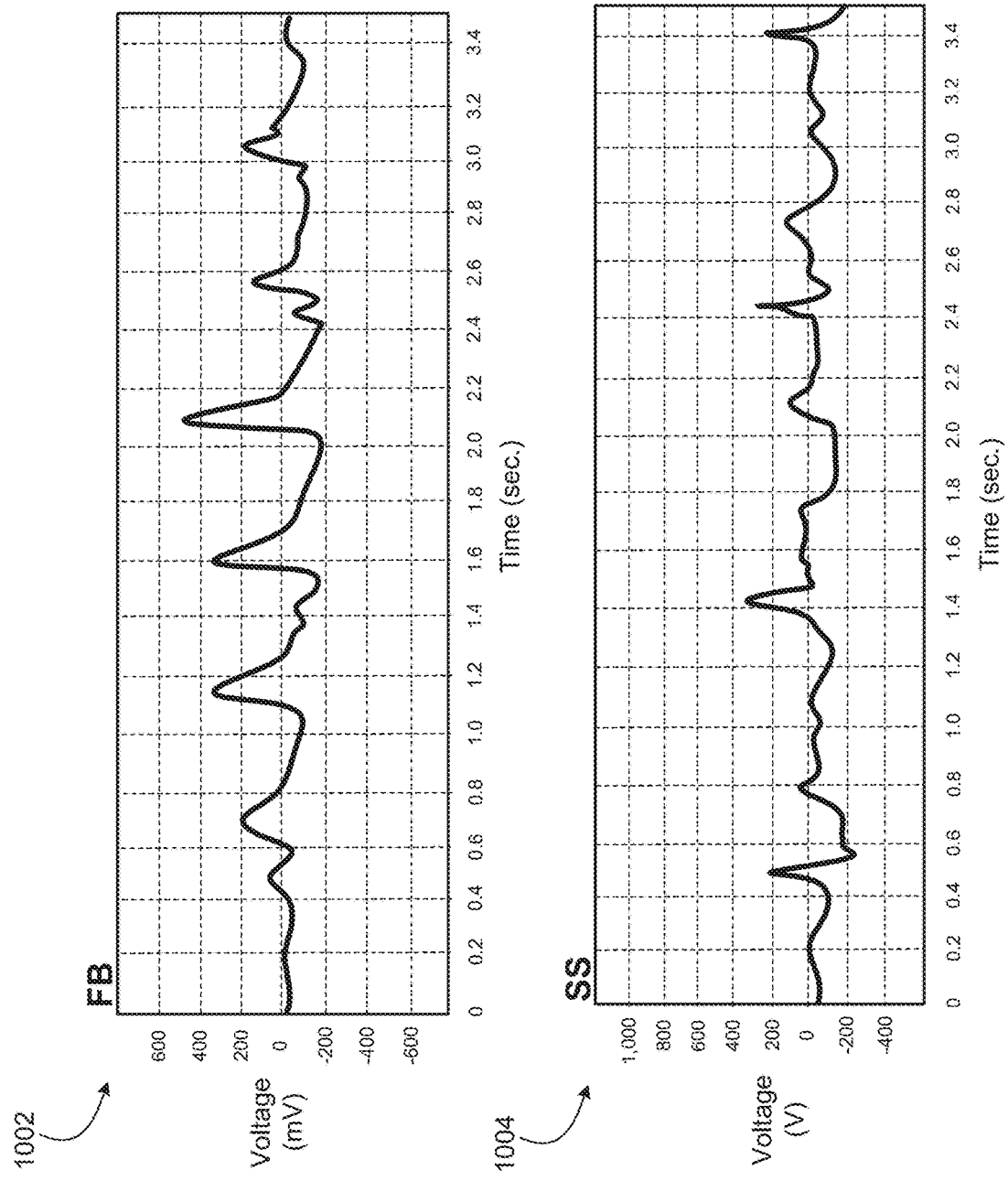
FIG. 10 is a graph of an ECG waveform of an example subject.

External defibrillators, such as AEDs, manual defibrillators with advisory algorithms, and wearable defibrillators categorize ECG data with regard to shocking into two groups: "shockable" or "non-shockable" rhythms. For certain time periods, for example, a time period of about one hour or less, at least a third category may be defined, in particular, for a wearable defibrillator. The third category may be described as a situation where the "subject should be unconscious, but surprisingly is still standing". More technically, the third category may be described as physiologic status dissonance, or just "Status Dissonance" (SD). Referring to FIG. 10, an upper ECG waveform 1002 shows a wide complex idioventricular rhythm with a rate of around 120 BPM for an example subject recorded by a front-to-back (FB) electrode configuration on the subject, and a lower ECG waveform 1004 shows a wide complex idioventricular rhythm with a rate of around 120 BPM for an example subject recorded by a side-to-side (SS) electrode configuration on the subject. Under many circumstances, a subject who exhibits the rhythm shown in the lower ECG waveform 1004 is not conscious. However, from the recorded file of the example subject, it is known that this subject remained conscious for at least thirty minutes following the arrhythmia. There was a significant period of delay from the time of the wide complex idioventricular rhythm until the wearable defibrillator initiated charging of the high voltage capacitor and performed the subject notification sequence. The wearable defibrillator did not initiate charging and perform the subject notification sequence because the detection thresholds in a conventional wearable defibrillator are set to generate a high level of specificity so that false shocks are not delivered to the conscious subject and the subject is not burdened or unnecessarily worried with false notifications and/or the defibrillator charging. The higher level of specificity comes at the expense of a lower sensitivity for the detection of potentially lethal arrhythmias; in this way, there is trade-off between sensitivity and specificity in a detection algorithm.

In some embodiments, to accomplish a short term (up to 4 hour) early warning, the control unit 120 may perform a second shockable rhythm detection algorithm that has been tuned for higher sensitivity on the ECG data (e.g., perhaps at the expense of specificity). For example, the second algorithm may be set to trigger detection of a Status Dissonance (SD) for wide complex ventricular tachycardia (VTACH) with a rate in excess of about 115 BPM, unlike existing algorithms that typically have the rate cutoff for VTACH at about 150 or about 180 BPM. The QRS width cutoff criteria for VTACH detection may be set for a narrower (less stringent) width than that typically used to detect SD. When the control unit detects SD using the second shockable rhythm detection algorithm, actions may be taken by the wearable medical device 100 to respond to the SD, such as the actions shown in FIG. 12.

Alternatively, the same algorithm that is used for the shockable rhythm detection may have at least two different sets of detection criteria thresholds. The control unit 120 may determine detection based on each of the more and less sensitive thresholds, and use the two or more determined responses for differing purposes, e.g., one response for early warning and the other response for defibrillation. Alternatively, the control unit 120 may analyze the ECG or other physiologic waveform data by applying different algorithms to different ECG or other physiologic waveform time segments, for example, alternating three second segments, alternating two second segments, etc. If the control unit 120 employs more than two thresholds, or more than two detection algorithms, the algorithms or decision thresholds may be used on a sequential, alternating basis, e.g., for algorithms 'A', 'B', and 'C', the algorithms may be run on the ECG in the sequence ABCABCABC.

Alternatively, the wearable medical device may detect SD by using the higher sensitivity shockable rhythm detection on the ECG data and detecting SD via one or more sensors in addition to the ECG waveform analysis. The second or tertiary sensors may comprise a pulse oximeter clipped onto the concha of the subject's ear that detects the subject's pulse, an accelerometer located in the wearable defibrillator or elsewhere on the subject's body to detect if the subject is vertical or horizontal, or if the subject is still moving, an acoustic sensor located on the subject's body in the vicinity of the subject's heart to detect the sound of heart beats, lung sounds, etc. When the more sensitive ECG rhythm detector detects a "shockable" rhythm, but the ancillary sensors detect viability, e.g. a pulse, a heart sound, subject activity or verticality, the medical device or system can determine that the subject is in the SD phase and perform the appropriate functions for the SD phase. If the ancillary sensors indicate non-viability, the wearable medical device 100 can proceed to the true shockable phase indicated by the higher sensitivity shockable rhythm detection.

As described herein, event estimation of risk scores may be used to determine a response or a plan of action, or to provide feedback to the subject and/or a medical provider based on the likelihood or probability of the subject experiencing a medical event, e.g., an adverse cardiac event or other degradation in medical condition. One category of event estimation of risk scores may be based on the likelihood of a subject experiencing an adverse cardiac event during a fairly short time period from a present time, such as within about five to about thirty minutes, e.g., within about five minutes, within about ten minutes, within about fifteen minutes, within about 20 minutes, and within about 30 minutes or more. If the subject and/or the medical professional are provided with about a five to thirty minute window of advance notice of a likely adverse cardiac event, various actions may be taken to mitigate the effects of such an event. These actions may range from providing alarms or information to the subject and/or a caregiver, alerting the medical professional, and/or preparing or triggering a defibrillation device. The time periods may be used to drive system, clinician, user and device activity via communication to the subject or clinicians who are either remote or local to the subject, or device activity that takes the form of therapeutic interventions such as pacing, defibrillation, neural stimulation, etc. Some embodiments may use any number of time periods, time periods of differing durations, and/or employ more continuous risk measures, such as those shown in FIG. 6B.

In some embodiments, if the event estimation of risk score satisfies an acceptable warning threshold, an early warning may be provided to the subject. For example, the wearable medical device 100 may provide an audio and/or visual alarm to the subject to reduce the likelihood of a secondary injury, e.g., falling, vehicle accidents, etc. The early warning system may enable the subject to plan near-term activities and/or avoid activities in which the subject is not protected, such as activities where a defibrillation device is removed, e.g., showering, garment changing, holding small children, etc. For example, the early warning may comprise a "quick screen" including an audio and/or video output that indicates to the subject wearing the device that the subject should not take off the wearable defibrillator to take a shower or change his or her clothes. The early warning may enable the subject to reattach defibrillation pads prior to the occurrence of an adverse cardiac event. For example, if a subject is in the shower and receives an early warning signal based on an elevated cardiac event estimation of risk score, the subject may reattach the defibrillation pads to be prepared if the adverse cardiac event occurs.

A type and manner of warning provided to the subject based on the cardiac event estimation of risk score may vary based on the criticality measure and confidence measure of the event estimation of risk score. For example, if the confidence measure does not satisfy a confidence threshold or the criticality measure does not satisfy a criticality threshold, the subject may be advised to not to take off the defibrillation device and to stop any current activities; however, if the predicted criticality measure and confidence measure each satisfy the respective thresholds, the warning may be more abrupt and warn the subject that a shock may be imminent, enabling the subject time to prepare for the event. In some implementations, if the confidence measure does not satisfy a confidence threshold, the device may refrain from performing an action (e.g., delivering a shock) or perform a different action than what would be performed if the confidence measure did satisfy the confidence threshold. In some implementations, if the confidence measure does not satisfy a confidence threshold, the device may take steps intended to improve the confidence measure. For example, the device may perform additional measurements on the subject, increase a frequency at which measurements are taken, etc. The system thus provides a systematic and varied response based on the criticality of the event and the probability that the event will occur.

If an estimation of time to a potential event is relatively short, for example, about 15 minutes or less, the subject may be instructed by the wearable medical device 100 to initiate a Valsalva maneuver. The subject may be instructed by a physician, who may have received an alert on a cellphone or computer via wired and wireless communication networks, or automatically via voice commands or other written or audio instructions from the wearable medical device 100, or via voice prompts or instructions from computing device 550 with which the wearable device communicates, to perform the Valsalva maneuver. A Valsalva maneuver includes the subject taking in a large breath, pinching his or her nose for a few seconds, and releasing the breath. The Valsalva maneuver stimulates the parasympathetic nervous system, which may result in the prevention of lethal ventricular arrhythmias. Other maneuvers may also be instructed to the subject such as bending over, or thumping their own chest with a precordial thump. Alternatively, the wearable medical device 100 may electrically pace the vagal nerve in response to an elevated event estimation of risk score through a transcutaneous electrical stimulation (TENS) waveform with electrodes placed in the wearable device shoulder strap near the subject's collarbone. The stimulation may be magnetic.

A type of feedback provided to the subject may be designed to limit the stress exhibited by the subject in response to the warning. For example, a warning advising that the subject is exhibiting an increased likelihood of an adverse cardiac event may induce other stress related adverse health effects. Accordingly, a more gentle warning, such as "performing advanced diagnostics; keep the vest on for ten minutes" or "check electrodes", may be conveyed to the subject by the wearable medical device 100 in addition to or in place of more other warnings. The more gentle warnings or other similar warnings may be generated randomly or at preset time intervals to condition the subject to their existence so that the subject does not associate them with an increased likelihood of an adverse cardiac event that may induce other stress related adverse health effects.

The wearable medical device 100 may selectively charge a capacitor of the defibrillation device based on the cardiac event estimation of risk score. The energy for shocking a subject in the defibrillation device needs to be built up, such as by charging the capacitor, and that build-up of energy may take an appreciable length of time. Because the cardiac event estimation of risk score provides an early indicator of a likely adverse cardiac event, when the cardiac event estimation of risk score satisfies a charging threshold, the system may begin charging the capacitor. For example, the system may analyze a subject's needs in advance and begin charging a capacitor or other appropriate energy delivery mechanism sufficiently in advance of the time that a shock is estimated to be needed, so that the shock may be delivered as soon as the shock is needed, e.g., when a shockable rhythm is detected. The cardiac event estimation of risk score may thus be used to initiate charging of a defibrillator, such as an AED. Advanced charging according to some embodiments enables defibrillation to be readily available, and may extend the battery life of the defibrillator. Exemplary methods of charging a defibrillator are described, for example, in U.S. Patent Application Publication No. 2011/0202101, entitled "DEFIBRILLATOR CHARGING", filed Feb. 11, 2011, the content of which is hereby incorporated by reference in its entirety. Providing early defibrillator charging based on the calculated cardiac event estimation of risk score may allow the size of the battery cells in the wearable medical device to be smaller, because the capacitor may be charged over a longer period of time due to the early warning provided by the event estimation of risk score.

If the wearable medical device 100 comprises a wearable defibrillator, such as a LifeVest™ wearable cardioverter defibrillator available from ZOLL Medical Corporation of Chelmsford, Mass., the cardiac event estimation of risk score may enable a reduction in the amount of hardware included in the Holter based wearable medical device. For example, the wearable medical device may include a plurality of therapy electrodes, e.g., therapy electrodes 114 shown in FIG. 2, that are electrically coupled to the control unit and capable of delivering one or more therapeutic defibrillating shocks to the body of the subject. In order to reduce the hardware, the electrodes provided in the wearable medical device may be dry electrodes which do not require a gel to be dispersed on the skin of the subject prior to use. For example, the dry electrodes may include barbs configured to stick into the skin of the subject when delivering the electric shock. The barb electrodes may provide defibrillation capability for unexpected events. However, it may be beneficial to use wet electrodes for providing a defibrillation shock and, therefore, the wearable medical device 100 may advise the subject to change the electrodes connected to the device from the dry electrodes, which are typically provided initially, to a pair of wet electrodes when the cardiac event estimation of risk score satisfying a threshold indicating that defibrillation is likely to be needed.

The cardiac event estimation of risk score may be used to alert medical professionals of a potential adverse cardiac event. For example, if the subject is in a hospital setting, the wearable medical device 100 may trigger an alarm based on the event estimation of risk score satisfying an alarm threshold to expedite emergency response, such as alerting a code team to respond to the subject. The alert may be transmitted to members of a Medical Emergency Response Team (MERT) or a Medical Emergency Team (MET), via the communication network 580, which may be a hospital communication network. The MERT or MET team can respond to subjects before an arrest occurs for the purpose of preventing the arrests.

As noted above, because some algorithms for medical premonitory event estimation and detection may be computationally intensive, some or all of the processing may be performed on server hardware that is separate from the wearable medical device itself that is either being worn or is nearby the subject. For example, in the hospital, the data from the subject may be streamed in real-time from the wearable medical device 100 to a server in the hospital network for processing. If the subject is outside of the hospital setting, the medical device may transmit physiological parameters of the subject, e.g., the ECG data, and/or responses to the physiological parameters determined by the wearable medical device 100 to the subject's doctor and/or transmit a message to the emergency room of a nearby hospital. Messages may be sent to other caretakers to alert them of the likelihood of an adverse cardiac event.

In some implementations, a portion of the processing of the algorithms for medical premonitory event estimation and detection is performed on the medical device, and a portion of the processing is performed on a server. For example, the processing of the algorithms may initially be performed by the medical device. If the processing becomes too computationally intensive for the medical device, the server can provide assistance. In this way, processing of the algorithms may be performed by the medical device alone when possible, and the server may be called upon for assisted processing only when necessary.

The cardiac event estimation of risk score may be used to initiate clinical treatment to reduce the likelihood of a cardiac event occurring and/or mitigate the adverse effects of a potential cardiac event. For example, the wearable medical device 100 or another medical device may provide automatic stimulation to the subject's heart in an attempt to prevent the onset of the adverse cardiac event, such as, for example, by pacing. When the cardiac event estimation of risk score satisfies a medication threshold for administering a medication, the wearable medical device may alert the user to administer an oral, injectable, or inhalable medication. For example, an inhalable medication, such as nitric oxide or sublingual nitroglycerin, which acts as a vasodilator, may be administered using an inhaler type device. An auto-injector, e.g., a medical device used to deliver a measured dose of medication, may be used to provide medication to the subject. The auto-injector may be in the form of a pen-based device in which a spring-loaded needle exits the tip of the device and penetrates the subject's skin to deliver the medication via a subcutaneous injection. Exemplary medications that may be included in the auto-injector include aspirin, vitamin E, an anti-inflammatory drug, a beta blocker, and/or a benzodiazepine drug, e.g., valium.

If an estimated time to a medical premonitory event exceeds about 30 minutes, the subject may be instructed by the wearable medical device 100 or a physician responding to a message from the wearable medical device 100 to take a pill containing a pharmaceutical agent that may protect the subject's heart and brain even if a cardiac arrest occurs. One such class of agents is KATP channel openers as described in O'Rourke, Brian, "Evidence for Mitochondrial K+ Channels and Their Role in Cardioprotection", *Circ Res.* 2004; 94:420-432, the content of which is hereby incorporated by reference in its entirety.

As shown in FIG. 11, the wearable medical device 100 may select various actions based on a combination of the criticality (risk) measure and confidence measure of the event estimation of risk score for a medical premonitory event. For example, the wearable medical device may perform or recommend one or more actions when each of the criticality measure and the confidence measure of the event estimation of risk score for a particular medical event satisfy the respective criticality and confidence thresholds for an associated time period. If one of the criticality measure or the confidence measure does not satisfy its respective threshold, an action may not be recommended or a different action may be recommended. The thresholds may differ based on the type of action to be recommended and the associated time period. For example, the criticality threshold and confidence threshold required to perform the action of informing the wearer that the medical device is performing advanced diagnostics (box 902) can be lower than the criticality threshold and confidence threshold required to perform an action of warning that a shock administration may be imminent (box 904) or preparing the device for treatment, e.g., charging, (box 912). As shown by FIG. 11, even if a criticality measure for a medical premonitory event satisfies a criticality threshold to alert a medical professional (box 906), if the confidence measure for the medical premonitory event does not satisfy the confidence threshold for alerting the medical professional for the associated time period, a different action or response for which the confidence threshold is satisfied may be selected by the wearable medical device 100, such as advising against removal of the device (box 908) or advising the subject to perform a behavior modification (box 910). The criticality and confidence thresholds may be higher for actions that are more invasive to the subject. By setting different thresholds for different actions, the wearable medical device 100 can provide a graded response to the subject's medical status. Similar sets of criticality and confidence thresholds may be associated with the time periods described herein.

In some embodiments, different actions or responses may be suggested to the subject or performed by the early warning system (e.g., the early warning system 10 of FIG. 5) based on various degrees of sensitivity and/or specificity of the event estimation of risk score. For example, a response determined based on an event estimation of risk scoring having a first sensitivity and a first specificity may be different than a response determined based on the event estimation of risk score having a different second sensitivity and/or a different second specificity. For example, a relatively high level of specificity may be required for charging a shocking mechanism or delivering a treatment so that false shocks or treatments are not delivered to the subject and the subject is not burdened or unnecessarily worried with false notifications and/or the defibrillator charging. A relatively lower level of specificity may be required for a response such as an instruction for behavior modification. A relatively higher sensitivity may be used to ensure detection of medical premonitory events; however, the higher level of sensitivity may result in a lower level of specificity and the detection of more false events. Accordingly, the determined response to the event estimation of risk score may vary based on the sensitivity and specificity of the event estimation of risk score.

The early warning system 10 may be modified based on a risk of the subject 104 having a medical event. For example, if a risk of the subject 104 having a medical event is relatively high, e.g., the risk of a cardiac arrest is relatively high, the sensitivity of an algorithm for determining the event estimation of risk score may be modified to be more sensitive to detecting the event. Sensitivity and specificity may be set on a patient-by-patient basis. A notification may be provided to a central monitoring station, e.g., a technical support center of a medical device manufacturer, when high-risk events are detected. The subject 104 may be instructed to charge a battery of the wearable medical device 100 more frequently than a typical charging frequency when the risk of a medical event is relatively high, e.g., above a risk threshold, to ensure that the device 100 is ready to respond to the medical event.

Various example time periods and associated actions that may be performed based on corresponding criticality and confidence thresholds are shown in FIG. 12 and described below.

Less than about One Hour Prior to Event

An event estimation of risk score may be used to alert medical professionals of a potential adverse cardiac or medical event that is likely to occur within about one hour. For example, if the subject is in a hospital setting, the wearable medical device 100 may trigger an alarm to inform a cardiologist or other medical professional to check on the subject. If the subject is outside of the hospital setting, the wearable medical device 100 may transmit the ECG of the subject to a cardiologist or other medical professional to enable the medical professional to follow-up with the subject. Messages may be sent to other caretakers to alert them of the likelihood of an adverse cardiac event.

The event estimation of risk score may be used to initiate clinical treatment to reduce the likelihood of the cardiac event occurring and/or to mitigate the adverse effects of the potential cardiac event. When the event estimation of risk score satisfies a threshold for administering medication, the wearable medical device may alert the user to administer an oral, injectable, or inhalable medication, for example, as described herein. The types of medications which may be administered at one hour prior to a predicted event may be different from those which are fast acting enough to have been administered within ten minutes of the predicted onset of the adverse cardiac event.

Less than about Three Hours Prior to Event

An event estimation of risk score may be used to alert a subject and/or a medical professional of a potential adverse cardiac event that is likely to occur within about three hours. When the event estimation of risk score indicates that an adverse cardiac event is likely to occur within about three hours, the wearable medical device 100 may perform actions to ensure that the battery has adequate charge to provide a defibrillation if one should become medically necessary. For example, if the cardiac event estimation of risk score satisfies a charging threshold, the wearable medical device may check the state of the battery and, if the battery has less than a predetermined percentage of its charge, the wearable medical device may suggest that the subject change the battery. However, it is not advisable to have the subject change the battery if there is a likelihood that the adverse cardiac event is going to occur in the immediate future. Accordingly, the wearable medical device may suggest changing the battery when the cardiac event estimation of risk score for a first time period does not satisfy a first threshold, (e.g., the likelihood of an adverse cardiac event within the time period is low), and the cardiac event estimation of risk score for a second time period with at a later time satisfies a second threshold, (e.g., the likelihood of an adverse cardiac event at a later time is moderate or high). By comparing the cardiac event estimation of risk scores from two time periods to the threshold, the subject reduces the risk of changing the battery during a time when an adverse cardiac event is likely to occur.

When a threshold has been satisfied by the event estimation of risk score, the wearable medical device 100 may notify a family member or caregiver of the subject by transmitting a message via the communications network 580. The family member or members to be notified are programmable in the medical device 100 and/or the base unit 530. A call center, e.g., a call center similar to the "On-Star"™ system of General Motors, may be automatically notified by the medical device 100 and/or the base unit 530, and live personnel at the call center may contact the subject via phone or other communication means, such as Skype or pager. The call center may contact the subject's physician to triage the event for the physician. The call center personnel may indicate to the subject to keep the device on, and if appropriate, to call the EMS system, e.g. 911.

In some embodiments, one or more of the warnings discussed above with respect to less than one hour to event may also be included.

Less than about One Day to about Three Days Prior to Event

A cardiac event estimation of risk score may be used to alert medical professionals of a potential adverse cardiac event that is likely to occur within about one to about three days. The medical event may comprise epileptic seizures, and hospital personnel may be warned in advance of the seizure, particularly for anesthetized epileptic subjects. If an event is predicted by the wearable medical device 100 and the subject is utilizing a wearable defibrillator with reduced or no therapy options, a three day warning may be used to trigger automatic shipment of a platform with more robust therapy features. Alternatively, the wearable medical device 100 may comprise a conventional defibrillator or other physiologic monitoring device, and may be used at the time of hospital admission to triage and assess the time-to-risk profile of the subject, and as a result of the testing a tiered therapeutic response may be provided. For example, if a risk is higher than 50% with a certainty of better than +/−10% of a potential cardiac arrest in the time period of the hospital stay, typically on the order of one through three days, the subject may be required to wear a wearable defibrillator such as the Lifevest™ type wearable defibrillator manufactured by ZOLL Medical during his or her stay in the hospital. If the risk is in the range of about 15 to about 50%, the subject may be required to wear a wearable monitor that does not incorporate a defibrillator for treating the subject should the subject experience a cardiac arrest. If the risk is less than 15%, the subject may merely be monitored at regular intervals by nursing staff, e.g. at 1 hour intervals. For each of the less acute cases of the wearable monitor and intermittent monitoring by nursing staff, medical premonitory event estimation and detection may be performed on an on-going basis, and if the subject's level of risk and certainty increases during his or her stay in the hospital, the subject may be switched from the wearable monitor to the combination wearable monitoring defibrillator, or from nurse monitoring to one of the wearable devices. Based on the triage time-to-risk profile of the subject, the subject may be admitted to a more appropriate acuity level of ward, or the subject may be moved to a lower acuity ward, or even discharged (e.g., while being protected by a wearable defibrillator). If the subject is outside of the hospital setting, the wearable medical device 100 may send the ECG of the subject to the subject's cardiologist or other medical professional via the communications network 580 to enable medical professionals to follow-up with the subject, if needed.

The subject may wear a wearable medical device 100 that has reduced or no therapy options, e.g., a device that does not include defibrillation capability. Based on a 1 to 3 day cardiac event estimation of risk score, the wearable medical device 100 may notify the subject of an increased likelihood of an adverse event and instruct the subject to switch to using a wearable medical device 100 that includes the therapy options. For example, if the event estimation of risk score satisfies a switching threshold, a warning may be issued to the subject to switch from the reduced or no therapy medical device to a wearable medical device that includes therapy options. If the event estimation of risk score satisfies a switching threshold and the subject does not possess a device with therapy options, a wearable medical device that includes the therapy options may be automatically shipped to the subject when the event estimation of risk score indicates an increased likelihood of an adverse event. For example, the wearable medical device 100 may automatically transmit an order for a wearable medical device that includes the therapy options via the communications interface 580 to a hospital or medical device provider that ships the medical device to the subject.

An event estimation of risk score for the one or three day time period may be used to aid medical professionals in determining and planning for discharges of subjects from a hospital setting. In some embodiments, three threshold levels may be used to facilitate discharge decisions. A first threshold may indicate a low likelihood of an adverse event and be associated with a recommendation to discharge the subject. A second, higher threshold may indicate a moderate likelihood of an adverse event and be associated with the recommendation to discharge the subject with a wearable medical device that includes a therapy/defibrillation capability. A third threshold that is higher than both the first and second thresholds may indicate an increased or higher likelihood of an adverse cardiac event and be associated with the recommendation to keep the subject in the hospital setting for further observation. The event estimation of risk score may thus provide a structured and systematic manner to plan discharges from a hospital setting.

In some embodiments, one or more of the warnings discussed above with respect to less than one hour and/or less than three hours to event may also be included.

Less than about One Week to about One Month Prior to Event

Event estimation of risk scores for longer-term time periods may be used to increase compliance with the use of the wearable medical device. For example, even with a low specificity or low event estimation of risk score, the wearable medical device 100 may provide feedback to the subject regarding the likelihood of an adverse cardiac event to motivate the subject to improve his or her compliance with wearing the wearable medical device 100 that includes the treatment capability.

Event estimation of risk scores for longer-term time periods may be used to determine extended care for the subject. For example, when an event estimation of risk score satisfies a threshold value, the medical professional may be prompted to extend the length of recommended use of the wearable medical device. For example, if the subject is nearing the end of the time during which he or she was requested to wear the wearable medical device, the physician or medical professional may extend the length of time during which the subject is requested to wear the wearable medical device if the criticality and likelihood of an adverse cardiac event satisfies associated thresholds.

For subjects having suffered a myocardial infarction, but whose ejection fraction is below criteria for receiving a wearable defibrillator in the waiting period prior to implantable defibrillator implantation, an elevated event estimation of risk score may be used to make a determination to provide a wearable defibrillator to the subject. For subjects presenting with syncope in the emergency department whose estimation of risk scores extend for durations in excess of their expected hospital stay, an elevated event estimation of risk score may be used to prescribe that the wearable subject receive a wearable defibrillator and be discharged with the use of the wearable defibrillator as protection.

Event estimation of risk scores for longer-term time periods may enable the subject to remain aware of potential warning signs which are indicative of event onset. For example, when an event estimation of risk score satisfies a threshold, the wearable medical device may ask the subject if he or she has noticed any warning signs and, if the subject has noticed the warning signs, prompt the subject to speak with their medical professional.

In some embodiments, one or more of the warnings discussed above with respect to less than one hour, less than three hours, less than one day, and/or less than three days to event may also be included.

About Three Months Prior to Event or More

Event estimation of risk scores for longer-term time periods, such as scores used to predict events likely to occur within a one and three month timeframe, or six month to one year timeframe, may be used to guide long-term treatment. For example, event estimation of risk scores may be used to guide long-term device planning. The event estimation of risk scores may be used to guide therapy based on risk trends, such as a continuously increasing event estimation of risk score. If the long-term event estimation of risk score continues to be elevated or is increasing, rehabilitation efforts to reduce risk, such as the administration of drug therapy, additional invasive testing, or prolonged use may be advised by the wearable medical device 100.

As noted herein, event estimation of risk scores may include a calculated criticality measure and a calculated confidence measure, and the combination of criticality and confidence may be used to determine an appropriate response to a medical premonitory event in an associated time period. For example, some treatments, such as defibrillation, may require a higher confidence value prior to implementation. Other treatments, such as instructing the subject to sit down, may require a lower confidence prior to implantation.

In some implementations, the early warning system described herein can be implemented and/or controlled at least in part by software executing on a computing device (e.g., the computing device 550 of FIG. 5). For example, an application configured to run on a mobile telephone and/or a tablet computer (e.g., a mobile application) can facilitate operation of the early warning system.

Figure 14A:
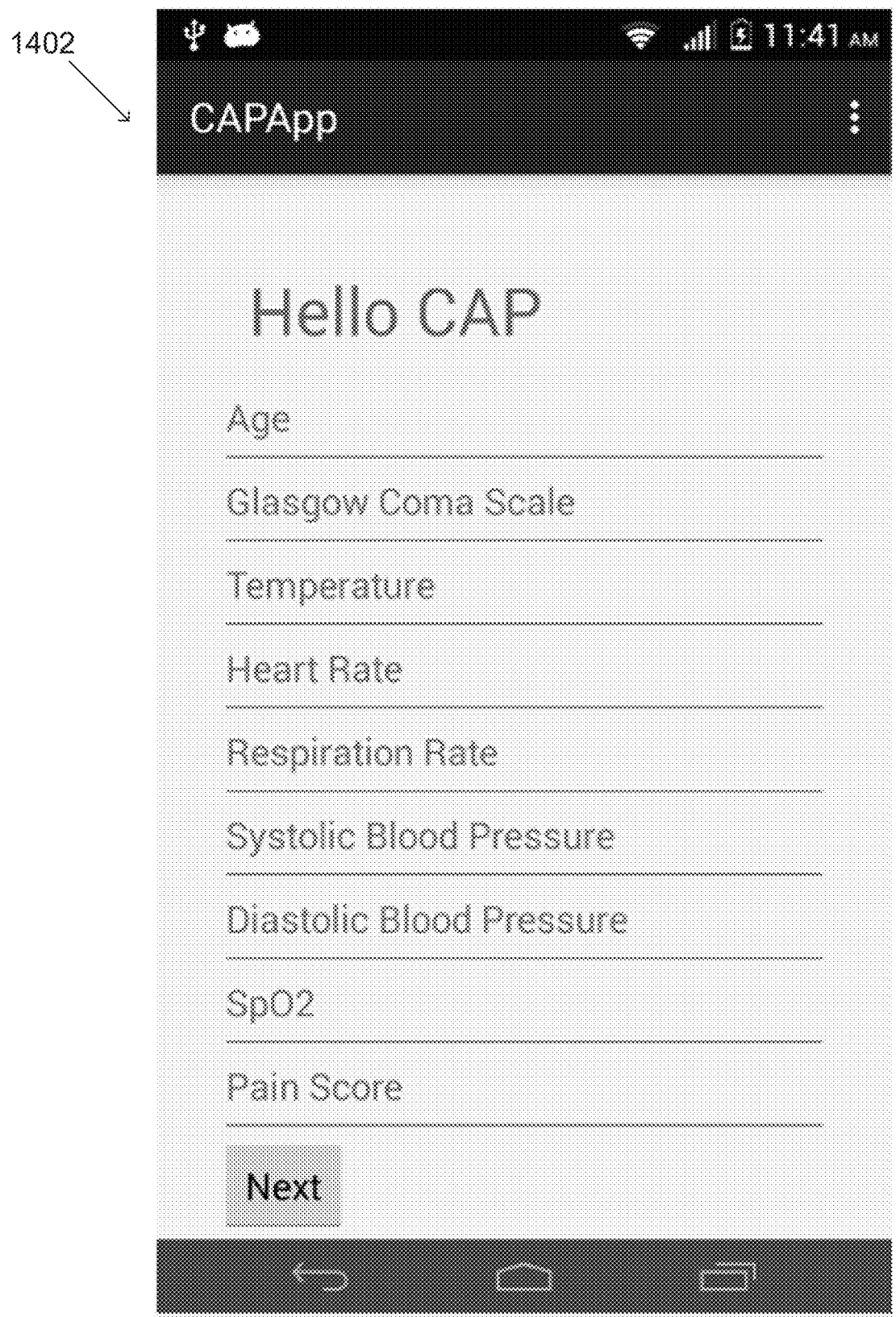
FIGS. 14A-D show example screenshots for an example cardiac arrest prediction (CAP) application.

FIG. 14A shows an example of a parameter input screen 1402 for an example of a cardiac arrest prediction (CAP) application (e.g., a mobile application). The parameter input screen 1402 may be presented when a clinician first uses the application. The patient, a medical professional, or both can enter patient information into the application. Some information, such as ECG data, entered into the application may be provided by the medical device (e.g., a defibrillator, a cardiac monitor, etc.). For example, some information may be provided over a wireless connection. The computing device can then use the entered patient information (and, e.g., data received by the medical device) to determine event estimation of risk scores and/or enhanced event estimation of risk scores. Information that can be entered via the application's user interface can include the patient's age, a Glasgow Coma Scale (GCS) score, a body temperature, a heart rate, a respiration rate, a systolic blood pressure, a diastolic blood pressure, a SpO2 measurement, and a pain score (e.g., on the scale of 1-10). One or more physiological parameters included in the patient information may be collected by the medical device and provided to the application, as described below (e.g., while the medical device is sending the ECG data). In some implementations, the parameter input screen 1402 can display values for physiological parameters that are automatically measured and sent by the medical device. The medical professional may be able to edit (e.g., override) the automatic measurements by manually entering values for physiological parameters. If one or more physiological parameters are missing values, the medical professional may be prompted to manually enter these values prior to any patient scores being computed. In some implementations, user-entered and/or clinician-entered data are not overridden by data automatically measured by the medical device.

The application and/or the medical device may check one or more of the physiological parameters to ensure that they fall within a permissible range. For example, the age parameter may require a value greater than or equal to 18, the body temperature parameter may require a value greater than or equal to 90° F. and less than or equal to 110° F., the heart rate, respiration rate, systolic blood pressure, diastolic blood pressure, and SpO2 parameters may require values greater than 0, and the systolic blood pressure may require a value greater than the diastolic blood pressure value.

Figure 14B:
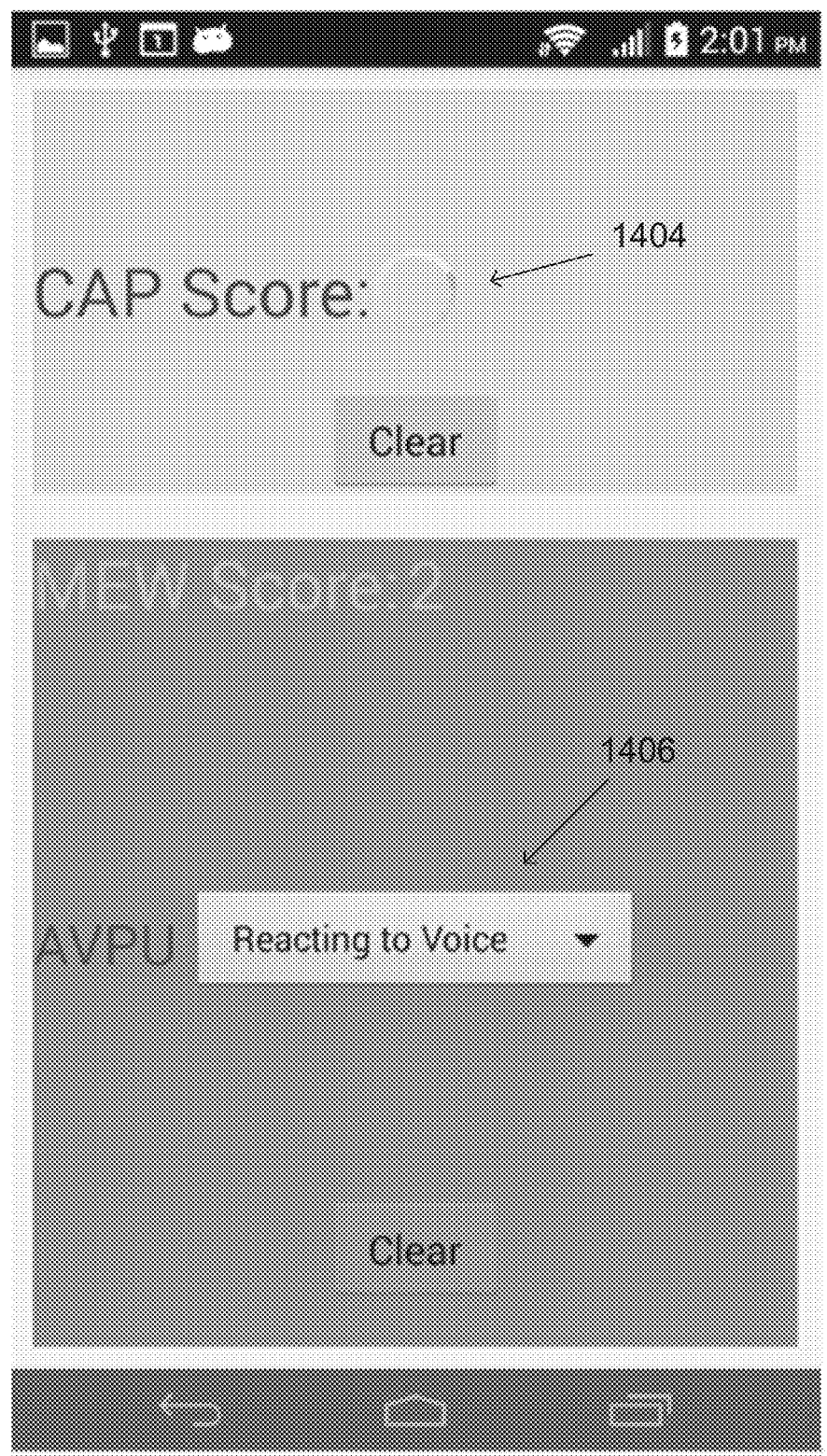

Before or after the initial patient information is provided, the medical device can monitor the patient by measuring and/or recording one or more types of physiological data, including receiving a signal comprising ECG data. As shown in the screenshot of FIG. 14B, the application displays a data collection indicator 1404 as the ECG data is received. In some implementations, five minutes of ECG samples are measured from the patient at 250 Hz. In some implementations, the five minutes of ECG data may be continuous or non-continuous. In some implementations, the five minutes of ECG data must have fewer than a predetermined number of interruptions in order to be considered an acceptable dataset. In some implementations, the ECG data must have an amount of noise that falls below a permissible threshold. An initial CAP score can be determined for the patient based on the received ECG data and entered vital sign data. The CAP score is sometimes referred to as the event estimation of risk score, or simply as the event risk score.

Figure 14C:
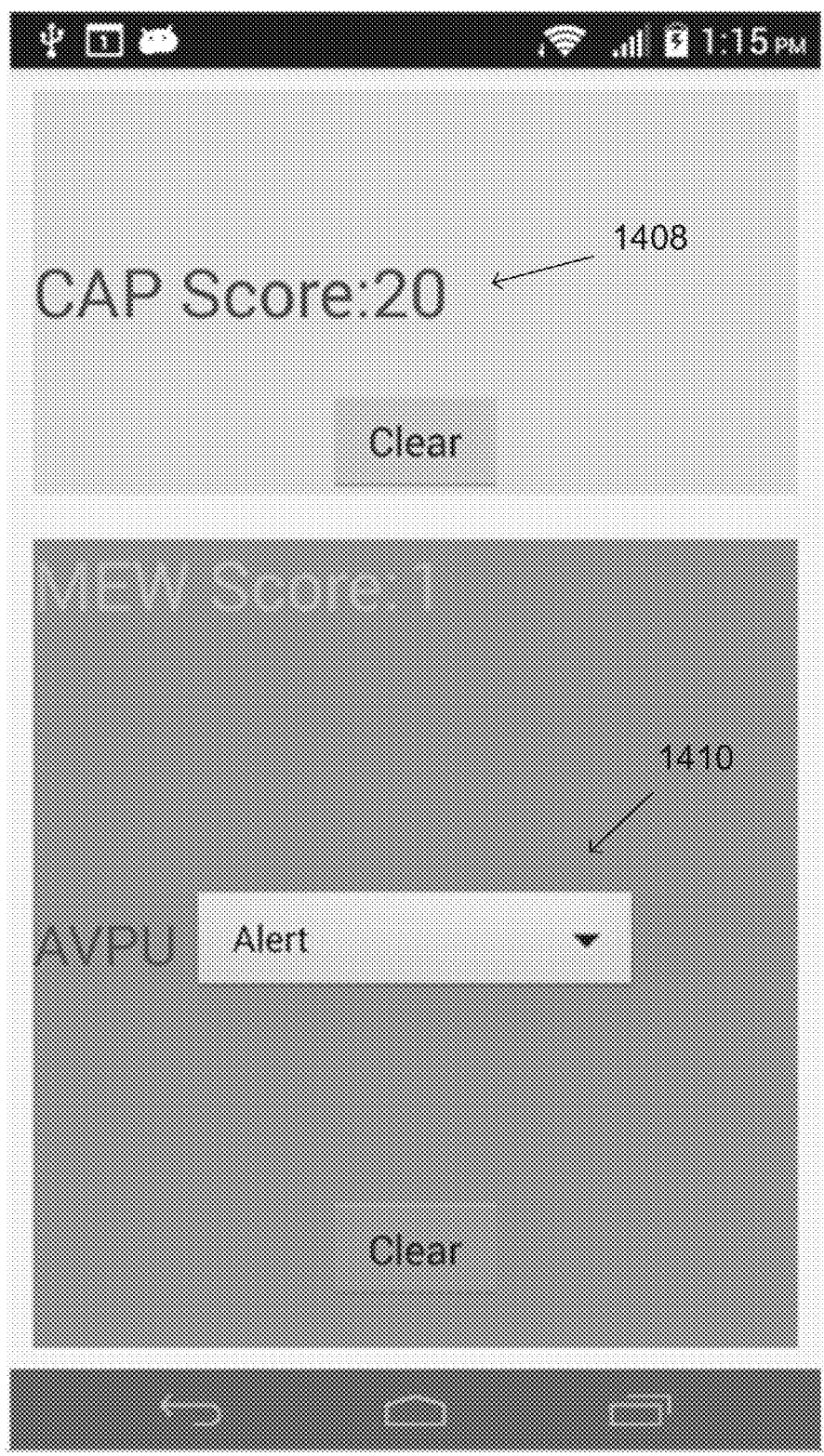

In some implementations, a Modified Early Warning (MEW) score is also determined for the patient. A relatively high MEW score can indicate that the patient may have a deteriorating condition and/or an acute illness. The MEW score may be determined separately and/or independently from the CAP score. In some implementations, the MEW score may be based on at least some different information than that used for determining the CAP score. An Alert, Voice, Pain, Unresponsive (AVPU) parameter may be required in order to computer the MEW score. The AVPU parameter is an indication of the responsiveness and or level of consciousness of the patient. The AVPU parameter may be a simplification of the GCS score. The AVPU parameter can have a value of "alert" indicating that the patient is fully awake (although not necessarily oriented). A patient with the "alert" parameter will have spontaneously open eyes, will respond to voice (although may be confused), and will have bodily motor function. The AVPU parameter can have a value of "voice" indicating that the patient can make some kind of response when spoken to. The response can be in any of three component measures of eyes, voice, or motor. For example, a patient who opens his eyes in response to being asked "Are you OK?" may be assigned an AVPU parameter of "voice." The response may be as little as a grunt, moan, or slight move of a limb when prompted by the voice of a rescuer. The AVPU parameter can have a value of "pain" indicating that the patient makes a response in any of three component measures of eyes, voice, or motor in response to application of a pain stimulus, such as a central pain stimulus like a sternal rub or a peripheral stimulus such as squeezing the patient's fingers. A patient with some level of consciousness (e.g., a fully conscious patient would not require a pain stimulus) may respond by using his voice, moving his eyes, or moving a part of his body (e.g., abnormal posturing). The AVPU parameter can have a value of "unresponsive" indicating that the patient does not give any eye, voice, or motor response to voice or pain stimulus. The appropriate parameter can be selected in the AVPU selection menu 1408. Referring to FIG. 14C, the initial CAP score 1408 and the MEW score 1410 is determined for the patient based on the received ECG data and the selected AVPU parameter 1406. The process for calculating the CAP score 1408 and the MEW score 1410 is described in more detail below with reference to FIG. 15.

Figure 14D:

FIG. 14D shows an example of a connection screen 1412 for creating a communication association between the mobile application and the medical device. The patient and/or the caregiver can enter an IP address of the medical device with which the application is to be associated, thereby allowing for the download of information from the medical device to the application (and, e.g., the computing device on which the application is running). The connection screen 1412 may be presented after the patient information is received via the parameter input screen 1402 of FIG. 14A. After a connection between the application and the medical device is established, the mobile application can begin receiving data and/or measuring data and/or recording the physiological data as described above. In some implementation, an identifier of the medical device other than the IP address may be provided instead of or in addition to the IP address. In some implementations, the application can be configured to automatically associate with the medical device without the aid of the connection screen 1412.

Once an association is established between the application and the medical device, the computing device on which the application is running may be configured to provide information related to the patient to another device, such as a device of an external entity and/or a remote server (e.g., a remote host server). For example, patient data may be streamed (e.g., in real-time) from the computing device to a server in a hospital network for processing. In some implementations, patient data may be streamed to a cloud hosted server for data storage and further detailed data analysis. If the patient is outside of the hospital setting, the computing device may transmit information related to the patient (e.g., physiological parameters of the patient, ECG data, responses to physiological parameters determined by the medical device, information related to the CAP score, information related to the MEW score, etc.) to the patient's doctor and/or transmit a message to the emergency room of a nearby hospital. Messages may also be sent to other caretakers to alert them of the likelihood of an adverse cardiac event.

As described above, processing of data may occur at various locations (e.g., on various devices) of the early warning system (10 of FIG. 5). For example, at least some of the data (e.g., ECG data received by the medical device, data input via the application, etc.) may be processed on any combination of the computing device (e.g., the mobile device), the medical device, the base unit, a server, the internet, a cloud hosted server, and/or a second medical device (e.g., a second medical device such as a defibrillator or a cardiac monitor that may be in communication with the medical device). In some implementations, patient data (e.g., ECG data) is transmitted to the mobile device, and at least some of the processing of the patient data is performed on the mobile device. In some examples, because some algorithms for medical premonitory event estimation and detection may be computationally intensive, at least some of the processing for determining event estimation of risk scores and/or actions in response thereto may be performed on server hardware that is separate from the mobile device and the medical device.

FIG. 15 shows an example of various physiological parameters that can be considered in computing the MEW score. The MEW score is the sum of the individual physiological parameter scores. For example, a patient with a systolic blood pressure of less than 70 mmHg may contribute 3 to the MEW score; a patient with a systolic blood pressure of between 71 and 80 mmHg, a heart rate under 40 beats per minute, a respiratory rate of less than 9 breaths per minute, a body temperature of less than 35° C., and an AVPU parameter of "voice" may have a MEW score of 9; a patient with a systolic blood pressure of between 81 and 100 mmHg, a heart rate of between 41 and 50 beats per minute, a respiratory rate between 9 and 14 breaths per minute, a body temperature between 35° C. and 38.4° C. (e.g., inclusive), and an AVPU parameter of "alert" may have a MEW score of 2; a patient with a systolic blood pressure of between 101 and 199 mmHg, a heart rate of between 51 and 100 beats per minute, a respiratory rate of between 9 and 14 breaths per minute, a body temperature of between 35° C. and 38.4° C. (e.g., inclusive), and an AVPU parameter of "alert" may have a MEW score of 0; a patient with a systolic blood pressure of between 101 and 199 mmHg, a heart rate between 101 and 110 beats per minute, a respiratory rate of between 15 and 20 breaths per minute, a temperature between 35° C. and 38.4° C. (e.g., inclusive), and an AVPU parameter of "voice" may have a MEW score of 3; a patient with a systolic blood pressure of greater than 200 mmHg, a heart rate of between 111 and 129 beats per minute, a respiratory rate of between 21 and 29 breaths per minute, a body temperature of greater than or equal to 38.5° C., and an AVPU parameter of "pain" may have a MEW score of 10; and a patient with a systolic blood pressure of greater than 200 mmHg, a heart rate of greater than or equal to 130 beats per minute, a respiratory rate of greater than or equal to 30 breaths per minute, a body temperature of greater than or equal to 38.5° C., and an AVPU parameter of "unresponsive" may have a MEW score of 13.

In some implementations, a patient who has a relatively high MEW score (e.g., a MEW score of 4 or 5) should be subject to more frequent observation by a medical professional. For example, it may be appropriate to observe the patient at least once every twelve hours, once every six hours, once every three hours, once per hour, once every thirty minutes, or even continuously depending on the particular MEW score. In some implementations, a patient with a MEW score of 1 may also require more frequent observation. In some implementations, a patient with a MEW score of 1 may be subject to more frequent observation if a subsequent MEW score is also 1 or higher.

FIG. 16 shows an example of various patient characteristics that can be considered in computing the Glasgow Coma Scale (GCS) score. The GCS score is composed of three tests based on the patient's eye functions, verbal functions, and motor functions. The patient is given a separate value for each of these functions, and the composite value is the GCS score. The patient can receive an eye function value of 1 (does not open eyes) to 4 (opens eyes spontaneously); the patient can receive a verbal function value of 1 (makes no sounds) to 5 (oriented, converses normally); the patient can receive a motor function score of 1 (makes no movements) to 6 (obeys commands). The lowest possible GCS score is 3, which can be indicative of the patient being in a deep coma or being dead, and the highest possible GCS score is 15, which can be indicative of the patient being fully awake and responsive.

Figure 17:
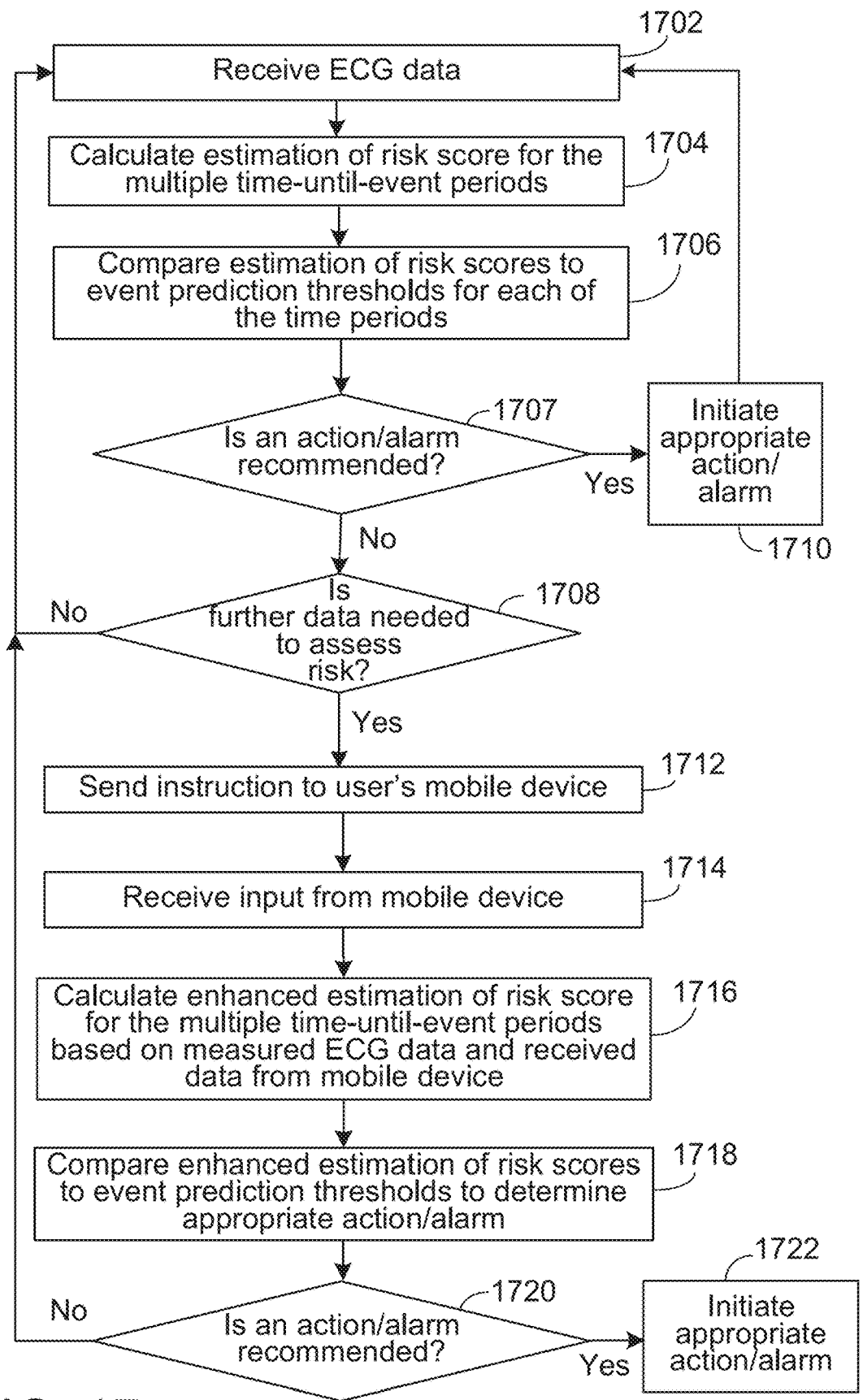
FIG. 17 is a flow chart of a medical premonitory event estimation method.

FIG. 17 shows a process for receiving additional data to calculate the Modified Early Warning Score (MEWS), sometimes referred to as an enhanced event estimation of risk score. At stage 1702, a wearable medical device 100 monitors a subject by measuring and/or recording one or more types of physiological data, including receiving a signal comprising ECG data. The ECG data may be received from any appropriate source of subject ECG data. For example, the ECG data may be received in real time from the ECG electrodes (112 of FIG. 2) attached to the subject or from previously recorded data received from a storage device. The signal including the ECG data may be received with additional subject data, including subject statistics, other physiological data recordings, medical history, physical exam findings, and other medical information that might be requested by a user. The additional subject data may be used in conjunction with subject specific ECG data for data processing and display.

At stage 1704, the control unit 120 calculates event estimation of risk scores for multiple time-until-event periods. Each of the event estimation of risk measures may include a calculated criticality measure and a calculated confidence measure.

At stage 1706, the control unit 120 compares the event estimation of risk scores for each of the calculated time-until-event periods to stored event estimation of risk thresholds. The comparison provides information which is used by the control unit 120 to determine a recommended treatment plan or course of action.

At stage 1707, the control unit 120 determines whether an action and/or alarm is recommended based on a comparison of the event estimation of risk scores to the event estimation of risk thresholds. If an action or alarm is recommended, the wearable medical device initiates the appropriate action and/or alarm at stage 1710 and processing returns to stage 1702 for the wearable medical device 100 to monitor the subject. For example, if a particular event estimation of risk measure for a particular time period satisfies the stored threshold value, an associated action is either performed by the system or recommended to the subject. Exemplary actions may include requesting that the subject keep on a medical device, suggesting to the subject to lessen physical activity, administration of medication, and/or defibrillation. If an action or alarm is not recommended, at stage 1708, based on the results of the comparison of the event estimation of risk measures to the event estimation of risk thresholds, the control unit 120 determines whether additional data is needed to assess the risk of the subject encountering an adverse cardiac event. Further information may be needed, for example, if the criticality measure is elevated, e.g., satisfies a criticality threshold, but the confidence value does not satisfy a confidence threshold.

If the control unit 120 determines that further information is not needed in stage 1708, the control unit 120 may return to receiving the ECG data at stage 1702. If further information is determined to be needed to assess the risk of the subject encountering an adverse cardiac event, the control unit 120 sends an instruction to a computing device associated with the subject, e.g., device 550, at stage 1712. In response to the communication to the subject's mobile device, at stage 1714, the control unit 120 receives an input or response from the subject (e.g., via the computing device 550). Examples of the request sent to the subject and the response from the subject may include requesting that the user indicate whether he or she is experiencing a particular symptom, such as tingling in the arm. The subject enters data on the computing device and the data is sent to the wearable medical device.

In some embodiments, the wearable medical device 100 may send a request to the subject to focus a camera on his or her face. The subject may position a camera, e.g., a smart phone camera included in computing device 550, such that an image of the subject's face is captured. The control unit 120 may perform facial recognition analysis on the image to analyze the emotional and/or physical status of the subject. The camera may be included in a wearable device, such as a pair of glasses which have a camera facing inwardly toward the subject. The facial analysis may be used by the wearable medical device to supplement the confidence score and analysis. In some embodiments, a galvanic skin response and/or a retinal response may be used to supplement the analysis.

Additionally, or alternatively, voice analysis may be used to provide data for assessing risk. For example, the wearable medical device 100 may request that a user respond to a series of one or more questions which may be captured by a microphone in the wearable medical device 100 or the computing device 550. The responses to the questions may be compared by the control unit 120 or the device 550 to previously acquired baseline responses to the same questions to determine if the subject's voice quality and/or response time differs. A determination of whether the subject's voice quality differs in a manner that is indicative of increased stress or anxiety may be provided to the wearable medical device 100 and used as a factor to assess the risk of an impending adverse cardiac event. In some embodiments, the wearable medical device 100 may include the hardware to perform the above-mentioned functions rather than sending a signal to a remote computing device.

At stage 1716, the control unit 120 calculates an enhanced event estimation of risk score for the multiple time-until-event periods based on the measured ECG data (and, e.g., the additional information received from the mobile device 550). At stage 1718, the system compares the enhanced event estimation of risk score to the event estimation of risk thresholds for each of the time periods to determine an appropriate action and/or alarm. For situations in which the event estimation of risk score is relatively high or low, additional information need not be requested from the user to determine the user's risk level for an adverse cardiac event, however, in a middle range, e.g., between two threshold values, where it is unclear whether further actions should be performed, rather than performing those actions or ignoring the moderately elevated risk level, further information can be gathered from the subject in order to determine the appropriate action.

At stage 1720, the control unit 120 determines whether an action and/or alarm is recommended based on a comparison of the enhanced event estimation of risk scores to the event estimation of risk thresholds. If an action or alarm is recommended, the system initiates the appropriate action and/or alarm at stage 1722. For example, if a particular enhanced event estimation of risk measure for a particular time period satisfies the stored threshold value, an associated action can be either performed by the system or recommended to the subject. Exemplary actions may range from requesting that the subject keep on a medical device to suggesting to the subject to lessen physical activity to administration of medication to defibrillation.

The thresholds used to perform various actions may be set by the prescriber of the wearable medical device, e.g., by a medical professional, and/or thresholds set by the various modeling algorithms discussed herein may be adjusted by the medical professional. Enabling the medical professional to set the thresholds may provide various advantages. For example, if the wearable medical device provides a high number of false positive indicators for a particular subject, e.g., indications of a high likelihood of an adverse cardiac event where the event does not subsequently occur, the medical professional may modify the thresholds, such that the rate of false positives is decreased. Enabling the medical professional to set threshold levels may allow the medical professional to be alerted to the status of a subject when the subject's status reaches a level where the medical professional desires to become involved, such that the medical professional is not flooded with notifications for which they do not wish to be involved.

Although the subject matter has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment may be combined with one or more features of any other embodiment.

What is claimed is:

1. A system for medical premonitory event estimation, the system comprising:
    a cardiac device configured to monitor physiological information of a subject;
    a non-transitory computer-readable storage medium in communication with one or more processors and having instructions stored thereon which, when executed by the one or more processors, cause the one or more processors to perform operations comprising:
        acquiring, from the cardiac device, a first set of the physiological information obtained by the cardiac device during a first period of time,
        acquiring, from the cardiac device, a second set of the physiological information obtained by the cardiac device during a second period of time subsequent to the first period of time;
        determining a first risk score based on applying the first set of the physiological information to one or more machine learning classifier models, the first risk score indicating a probability of a cardiac arrhythmia event occurring during a first future time period,
        wherein the one or more machine learning classifier models are trained on training metrics comprising i) cardiac electrophysiology metrics of a first plurality of subjects, and ii) demographic or medical history metrics of the first plurality of subjects,
        wherein the one or more machine learning classifier models is processed using a validation protocol comprising validation metrics of a second plurality of subjects, and
        wherein one or more thresholds of the one or more machine learning classifier models is set based on the validation protocol;
        determining a second risk score for the subject based on applying the second set of the physiological information to the one or more machine learning classifier models, the second risk score indicating a probability of a cardiac arrhythmia event occurring during a second future time period; and
        providing the first and second risk scores as time changing series of risk scores; and
        classifying the first and second risk scores associated with estimating a risk of a potential cardiac arrhythmia event for the subject based on the one or more thresholds.

2. The system of claim 1, wherein the one or more thresholds comprise at least an elevated risk threshold and an immediate risk threshold, and
    wherein classifying the first and second risk scores comprises, for each of the first and second risk scores:
        classifying a risk of the potential cardiac arrhythmia event for the subject as an elevated risk based on one or both of the first score and the second risk score transgressing the elevated risk threshold; and
        classifying the risk of the potential cardiac arrhythmia event for the subject as an immediate risk based on one or both of the first risk score and the second risk score transgressing the immediate risk threshold.

3. The system of claim 1, wherein classifying the first and second risk scores comprises performing a time changing classification of the risk of the potential cardiac arrhythmia event for the subject based on the time changing series of risk scores.

4. The system of claim 1, wherein classifying the first and second risk scores comprises adjusting an underlying specificity of the one or more machine learning classifier models to reduce false positives in an underlying classification of the risk of the potential cardiac arrhythmia event for the subject.

5. The system of claim 1, wherein the validation metrics comprise a plurality of one or more of cardiac electrophysiology metrics, demographic metrics, and medical history metrics of the second plurality of subjects.

6. The system of claim 1, the operations further comprising:
    updating the validation metrics by at least one of 1) adjusting one or more of the metrics in the validation metrics, and 2) expanding the validation metrics based on appending additional one or more subjects to the second plurality of subjects; and
    refining the one or more thresholds based on the updated validation metrics.

7. The system of claim 1, the operations further comprising:
    updating the training metrics by at least one of 1) adjusting one or more of the metrics in the training metrics, and 2) expanding the training metrics based on appending additional one or more subjects to the first plurality of subjects; and
    retraining the one or more machine learning classifier models based on the updated training metrics.

8. The system of claim 1, wherein the validation metrics of the second plurality of subjects is independent from the training metrics of the first plurality of subjects.

9. The system of claim 1, wherein the one or more machine learning classifier models are validated on the validation metrics, and wherein the validation metrics comprises an indication of a presence or an absence of ectopic beats in an underlying one or more of the validation metrics.

10. The system of claim 1, the operations further comprising:
    discriminating between normal and ectopic beats in the first set of the physiological information.

11. The system of claim 1, wherein at least one of the training metrics and the validation metrics comprises metrics based on at least one of heart rate, heart rate variability, non-sustained ventricular tachycardia (VT) episodes count, and premature ventricular contraction (PVC) count.

12. The system of claim 1, wherein at least one of the training metrics and the validation metrics comprises metrics based on heart rate variability, and wherein the metrics comprise a standard deviation over time of normal-to-normal intervals.

13. The system of claim 1, wherein at least one of the training metrics and the validation metrics comprises metrics based on at least one of QRS width, QRS height, single lead QRS morphology, and dual lead QRS morphology.

14. The system of claim 1, wherein at least one of the training metrics and the validation metrics comprises metrics based on single lead QRS morphology, and wherein the metrics comprise an average over time of similarity scores respectively on side-to-side (SS) and front-to-back (FB) channels.

15. The system of claim 1, wherein at least one of the training metrics and the validation metrics comprises metrics based on QRS width, and wherein the metrics comprise at least one of a standard deviation over time of an estimated width of QRS complexes and a mean over time of the estimated width of QRS complexes.

16. The system of claim 1, wherein at least one of the training metrics and the validation metrics comprises metrics based on QRS height, and wherein the metrics comprise a standard deviation over time of an estimated height of QRS complexes.

17. The system of claim 1, wherein at least one of the training metrics and the validation metrics comprises metrics based on at least one of a QT variability, a ST depression, a ST elevation, a ST slope, a T-wave alternant, a T-wave variability, and a dual lead T-wave morphology.

18. The system of claim 1, wherein at least one of the training metrics and the validation metrics comprises heart sounds metrics.

19. The system of claim 18, wherein the heart sounds metrics comprise heart sound metrics corresponding to one or both of a third QRS complex and a fourth QRS complex.

20. The system of claim 1, wherein at least one of the training metrics and the validation metrics comprises electromechanical activation time metrics describing an interval from a first predetermined fiducial time-point in a first ECG signal to a second predetermined fiducial time-point in a subsequent mechanical activity of a heart.

21. The system of claim 20, wherein the first predetermined fiducial time-point in the first ECG signal comprises an onset of P-wave and QRS complexes, wherein the onset of the P-wave and QRS complexes comprises time-points relating to at least one of a) a P-wave, b) a Q-wave, c) an R-wave, and d) an S-wave.

22. The system of claim 20, wherein the subsequent mechanical activity of the heart comprises left ventricular wall motion.

23. The system of claim 22, wherein the second predetermined fiducial time-point in the subsequent mechanical activity of the heart comprises at least one of a) a time-point of maximal left ventricular wall motion, and b) a state of a relaxation of the left ventricular wall motion.

24. The system of claim 20, wherein the second predetermined fiducial time-point in the subsequent mechanical activity of the heart comprises a time-point of peak intensity of a heart sound corresponding to a first QRS complex.

25. The system of claim 20, wherein the second predetermined fiducial time-point in the subsequent mechanical activity of the heart is based on ultrasound measurements of the heart.

26. The system of claim 20, wherein the electromechanical activation time metrics comprises a percent electromechanical activation time metric.

27. The system of claim 2, wherein classifying the first and second risk scores comprises calculating at least one of an area under a plotted curve of the time changing series of risk scores and a mean of the time changing series of risk scores.

28. The system of claim 2, wherein the first and second risk scores are classified based on an amount that the first and second risk scores transgress the one or more thresholds.

29. The system of claim 2, wherein the first and second risk scores are classified based on a number of times that the time changing series of risk scores transgress the one or more thresholds.

30. The system of claim 1, the operations further comprising:
notifying at least one of the subject and a third party based on classifying the first and second risk scores.

31. The system of claim 30, wherein classifying the first and second risk scores comprises indicating at least one of an elevated risk and an immediate risk.

32. The system of claim 30, wherein notifying comprises sending a notification to at least one member of a medical team of the subject.

33. The system of claim 1, the operations further comprising:
adjusting a time interval between detection of a cardiac event and a treatment for the cardiac event based on classifying the first and second risk scores.

34. An external medical device for premonitory event estimation, the device comprising:
a cardiac device configured to monitor physiological information of a subject;
a non-transitory computer-readable storage medium in communication with one or more processors and having instructions stored thereon which, when executed by the one or more processors, cause the one or more processors to perform operations comprising:
acquiring, from the cardiac device, a first set of the physiological information obtained by the cardiac device during a first period of time,
acquiring, from the cardiac device, a second set of the physiological information obtained by the cardiac device during a second period of time subsequent to the first period of time;
determining a first risk score based on applying the first set of the physiological information to one or more machine learning classifier models, the first risk score indicating a probability of a cardiac arrhythmia event occurring during a first future time period,
wherein the one or more machine learning classifier models are trained on training metrics comprising i) cardiac electrophysiology metrics of a first plurality of subjects, and ii) demographic or medical history metrics of the first plurality of subjects,
wherein the one or more machine learning classifier models is processed using a validation protocol comprising validation metrics of a second plurality of subjects, and
wherein one or more thresholds of the one or more machine learning classifier models is set based on the validation protocol; and
determining a second risk score for the subject based on applying the second set of the physiological information to the one or more machine learning classifier models, the second risk score indicating a probability of a cardiac arrhythmia event occurring during a second future time period.

35. The external medical device of claim 24, wherein the external medical device comprises a wearable medical device.

36. The external medical device of claim 24, processors perform the operations further comprising:
   classifying the first and second risk scores based on the one or more thresholds; and
   modifying one or more functions or features of a user interface of the external medical device based on classifying the first and second risk scores.

37. The external medical device of claim 36, wherein the one or more thresholds comprise at least an elevated risk threshold and an immediate risk threshold, and
   wherein classifying the first and second risk scores comprises, for each of the first and second risk scores:
      classifying a risk of a potential cardiac arrhythmia event for the subject as an elevated risk based on one or both of the first second and the second risk score transgressing the elevated risk threshold; and
      classifying the risk of the potential cardiac arrhythmia event for the subject as an immediate risk based on one or both of the first risk score and the second risk score transgressing the immediate risk threshold.

38. The external medical device of claim 36, the operations further comprising providing at least the first and second risk scores associated with the potential cardiac arrhythmia event as time changing series of risk scores
   wherein classifying the first and second risk scores comprises performing a time changing classification of the risk of the potential cardiac arrhythmia event for the subject based on a time changing series of risk scores or adjusting an underlying specificity of the one or more machine learning classifier models to reduce false positives in an underlying classification of the risk of the potential cardiac arrhythmia event for the subject.

39. A non-transitory computer-readable storage medium in communication with one or more processors and having instructions stored thereon which, when executed by the one or more processors, cause the one or more processors to perform operations comprising:
   acquiring, from a cardiac device, a first set of physiological information of a subject obtained by the cardiac device during a first period of time,
   acquiring, from the cardiac device, a second set of physiological information of the subject obtained by the cardiac device during a second period of time subsequent to the first period of time;
   determining a first risk score based on applying the first set of physiological information to one or more machine learning classifier models, the first risk score indicating a probability of a cardiac arrhythmia event occurring during a first future time period,
   wherein the one or more machine learning classifier models are trained on training metrics comprising i) cardiac electrophysiology metrics of a first plurality of subjects, and ii) demographic or medical history metrics of the first plurality of subjects,
   wherein the one or more machine learning classifier models is processed using a validation protocol comprising validation metrics of a second plurality of subjects, and
   wherein one or more thresholds of the one or more machine learning classifier models is set based on the validation protocol;
   determining a second risk score for the subject based on applying the second set of physiological information to the one or more machine learning classifier models, the second risk score indicating a probability of a cardiac arrhythmia event occurring during a second future time period; and
   providing the first and second risk scores as time changing series of risk scores.

40. The non-transitory computer-readable storage medium of claim 39, the operations further comprising:
   discriminating between normal and ectopic beats in the first set of physiological information.

41. The non-transitory computer-readable storage medium of claim 39, the operations further comprising:
   classifying the first and second risk scores based on the one or more thresholds; and
   modifying one or more functions or features of a user interface of a external medical device based on classifying the first and second risk scores.

42. The non-transitory computer-readable storage medium of claim 41, wherein the one or more thresholds comprise at least an elevated risk threshold and an immediate risk threshold, and
   wherein classifying comprises, for each of the first and second risk scores:
      classifying a risk of a potential cardiac arrhythmia event for the subject as an elevated risk based on one or both of the first risk score and the second risk score transgressing the elevated risk threshold; and
      classifying the risk of the potential cardiac arrhythmia event for the subject as an immediate risk based on one or both of the first risk score and the second risk score transgressing the immediate risk threshold.

43. The non-transitory computer-readable storage medium of claim 41, wherein classifying the first and second risk scores comprises performing a time changing classification of the risk of the potential cardiac arrhythmia event for the subject based on the time changing series of risk scores or adjusting an underlying specificity of the one or more machine learning classifier models to reduce false positives in an underlying classification of the risk of the potential cardiac arrhythmia event for the subject.

* * * * *